(12) United States Patent
Altreuter et al.

(10) Patent No.: US 10,933,129 B2
(45) Date of Patent: Mar. 2, 2021

(54) METHODS FOR ADMINISTERING SYNTHETIC NANOCARRIERS THAT GENERATE HUMORAL AND CYTOTOXIC T LYMPHOCYTE RESPONSES

(75) Inventors: David H. Altreuter, Wayland, MA (US); Conlin O'Neil, Andover, MA (US); Petr Ilyinskii, Cambridge, MA (US)

(73) Assignee: Selecta Biosciences, Inc., Watertown, MA (US)

(*) Notice: Subject to any disclaimer, the term of this patent is extended or adjusted under 35 U.S.C. 154(b) by 0 days.

(21) Appl. No.: 13/560,955

(22) Filed: Jul. 27, 2012

(65) Prior Publication Data
US 2013/0028941 A1 Jan. 31, 2013

Related U.S. Application Data

(60) Provisional application No. 61/513,496, filed on Jul. 29, 2011, provisional application No. 61/513,526, filed on Jul. 29, 2011, provisional application No. 61/513,527, filed on Jul. 29, 2011.

(51) Int. Cl.
| *A61K 39/395* | (2006.01) |
| *A61K 39/385* | (2006.01) |
| *A61K 39/39* | (2006.01) |
| *A61K 47/59* | (2017.01) |
| *A61K 47/64* | (2017.01) |
| *A61K 39/00* | (2006.01) |

(52) U.S. Cl.
CPC ............ *A61K 39/385* (2013.01); *A61K 39/39* (2013.01); *A61K 47/59* (2017.08); *A61K 47/593* (2017.08); *A61K 47/645* (2017.08); *A61K 2039/55555* (2013.01); *Y02A 50/30* (2018.01); *Y10T 428/2982* (2015.01)

(58) Field of Classification Search
None
See application file for complete search history.

(56) References Cited

U.S. PATENT DOCUMENTS

| 3,608,066 | A | 9/1971 | Illartein |
| 4,009,257 | A | 2/1977 | Thomas et al. |
| 4,021,364 | A | 5/1977 | Speiser et al. |
| 4,225,581 | A | 9/1980 | Kreuter et al. |
| 4,631,211 | A | 12/1986 | Houghten |
| 4,756,907 | A | 7/1988 | Beck et al. |
| 4,929,624 | A | 5/1990 | Gerster et al. |
| 4,994,281 | A | 2/1991 | Muranishi et al. |
| 5,114,703 | A | 5/1992 | Wolf et al. |
| 5,118,528 | A | 6/1992 | Fessi et al. |
| 5,175,296 | A | 12/1992 | Gerster |
| 5,213,812 | A | 5/1993 | Jean-Marc |
| 5,229,490 | A | 7/1993 | Tam |
| 5,389,640 | A | 2/1995 | Gerster et al. |
| 5,500,161 | A | 3/1996 | Andrianov et al. |
| 5,514,378 | A | 5/1996 | Mikos et al. |
| 5,543,158 | A | 8/1996 | Gref et al. |
| 5,565,215 | A | 10/1996 | Ruxandra et al. |
| 5,578,325 | A | 11/1996 | Domb et al. |
| 5,582,172 | A | 12/1996 | Papisov et al. |
| 5,620,708 | A | 4/1997 | Amkraut et al. |
| 5,656,298 | A | 8/1997 | Kitchell et al. |
| 5,663,153 | A | 9/1997 | Hutcherson et al. |
| 5,733,572 | A | 3/1998 | Unger et al. |
| 5,733,925 | A | 3/1998 | Kunz et al. |
| 5,750,110 | A | 5/1998 | Prieels et al. |
| 5,762,904 | A | 6/1998 | Okada et al. |
| 5,792,475 | A | 8/1998 | Davis et al. |
| 5,837,752 | A | 11/1998 | Shastri et al. |
| 5,869,103 | A | 2/1999 | Yeh et al. |
| 5,871,747 | A | 2/1999 | Gengoux-Sedlik |
| 5,876,727 | A | 3/1999 | Swain et al. |
| 5,912,017 | A | 6/1999 | Mathiowitz et al. |
| 5,916,539 | A | 6/1999 | Pilgrimm |
| 5,916,597 | A | 6/1999 | Lee et al. |
| 5,928,647 | A | 7/1999 | Rock |
| 5,977,089 | A | 11/1999 | Arimilli et al. |
| 6,007,845 | A | 12/1999 | Domb et al. |
| 6,039,969 | A | 3/2000 | Tomai et al. |
| 6,043,224 | A | 3/2000 | Lee et al. |
| 6,060,082 | A | 5/2000 | Chen et al. |
| 6,083,505 | A | 7/2000 | Miller et al. |
| 6,130,082 | A | 10/2000 | Majarian et al. |
| 6,132,723 | A | 10/2000 | Malcolm |
| 6,159,502 | A | 12/2000 | Russell-Jones et al. |
| 6,194,388 | B1 | 2/2001 | Krieg et al. |
| 6,197,229 | B1 | 3/2001 | Ando et al. |
| 6,207,646 | B1 | 3/2001 | Krieg et al. |

(Continued)

FOREIGN PATENT DOCUMENTS

| CN | 1377279 A | 10/2002 |
| CN | 1692943 A | 11/2005 |

(Continued)

OTHER PUBLICATIONS

International Search Report and Written Opinion for PCT/US2012/048670 dated Feb. 27, 2013.
International Preliminary Report on Patentability for PCT/US2012/048670 dated Feb. 13, 2014.
[No Author Listed] Nanoparticles as Drug Carriers. Ed, Vladimir Torchilin. Imperial College Press. 2006. 754 pages.
Ackerman et al., Cellular mechanisms governing cross-presentation of exogenous antigens. Nat Immunol. 2004;5(7):678-84.
Aime et al., Lanthanide(III) chelates for NMR biomedical applications. Chemical Society Reviews. 1998;27:19-29.
Akaishi et al., Targeting chemotherapy using antibody-combined liposome against human pancreatic cancer cell-line. The Tohoku Journal of Experimental Medicine. 1994;175(1):29-42.

(Continued)

*Primary Examiner* — Yunsoo Kim
(74) *Attorney, Agent, or Firm* — Wolf, Greenfield & Sacks, P.C.

(57) ABSTRACT

Disclosed are methods for generating humoral and cytotoxic T lymphocyte (CTL) immune responses in a subject and related compositions.

19 Claims, 9 Drawing Sheets

Specification includes a Sequence Listing.

(56) References Cited

U.S. PATENT DOCUMENTS

| | | |
|---|---|---|
| 6,218,371 B1 | 4/2001 | Krieg et al. |
| 6,225,460 B1 | 5/2001 | Bischofberger et al. |
| 6,232,082 B1 | 5/2001 | Ennifar et al. |
| 6,239,116 B1 | 5/2001 | Krieg et al. |
| 6,245,776 B1 | 6/2001 | Skwierczynski et al. |
| 6,254,890 B1 | 7/2001 | Hirosue et al. |
| 6,288,040 B1 | 9/2001 | Muller et al. |
| 6,306,640 B1 | 10/2001 | Nicolette |
| 6,309,669 B1 | 10/2001 | Setterstrom et al. |
| 6,329,381 B1 | 12/2001 | Kurimoto et al. |
| 6,348,462 B1 | 2/2002 | Gerster et al. |
| 6,365,187 B2 | 4/2002 | Mathiowitz et al. |
| 6,387,397 B1 | 5/2002 | Chen et al. |
| 6,444,192 B1 | 9/2002 | Mattrey |
| 6,544,518 B1 | 4/2003 | Friede et al. |
| 6,558,951 B1 | 5/2003 | Tomai et al. |
| 6,585,980 B1 | 7/2003 | Chan et al. |
| 6,608,201 B2 | 8/2003 | Gerster et al. |
| 6,610,319 B2 | 8/2003 | Tomai et al. |
| 6,610,713 B2 | 8/2003 | Tracey |
| 6,632,671 B2 | 10/2003 | Unger |
| 6,635,283 B2 | 10/2003 | Edwards et al. |
| 6,656,469 B1 | 12/2003 | Svensson et al. |
| 6,686,472 B2 | 2/2004 | Gerster et al. |
| 6,693,086 B1 | 2/2004 | Dow et al. |
| 6,696,076 B2 | 2/2004 | Tomai et al. |
| 6,699,474 B1 | 3/2004 | Cerny |
| 6,723,429 B2 | 4/2004 | Bengs et al. |
| 6,747,156 B2 | 6/2004 | Johansson et al. |
| 6,767,702 B2 | 7/2004 | Mirkin et al. |
| 6,800,296 B1 | 10/2004 | Langer et al. |
| 6,811,975 B2 | 11/2004 | Cook et al. |
| 6,815,170 B1 | 11/2004 | Morton |
| 6,881,421 B1 | 4/2005 | Da Silveira et al. |
| 6,989,435 B2 | 1/2006 | Grainger et al. |
| 7,008,411 B1 | 3/2006 | Mandrusov et al. |
| 7,097,837 B2 | 8/2006 | Nielsen et al. |
| 7,129,222 B2 | 10/2006 | Van Nest et al. |
| 7,132,475 B2 | 11/2006 | Hubbell et al. |
| 7,147,862 B1 | 12/2006 | Prieels et al. |
| 7,149,574 B2 | 12/2006 | Yun et al. |
| 7,192,725 B2 | 3/2007 | Chan et al. |
| 7,223,398 B1 | 5/2007 | Tuck et al. |
| 7,238,711 B1 | 7/2007 | Grainger et al. |
| 7,247,502 B2 | 7/2007 | Ennifar et al. |
| 7,250,403 B2 | 7/2007 | Van Nest et al. |
| 7,250,499 B2 | 7/2007 | Mirkin et al. |
| 7,262,286 B2 | 8/2007 | Kandimalla et al. |
| 7,276,489 B2 | 10/2007 | Agrawal et al. |
| 7,285,289 B2 | 10/2007 | Nagy et al. |
| 7,357,936 B1 | 4/2008 | Garcon |
| 7,363,076 B2 | 4/2008 | Yun et al. |
| 7,375,180 B2 | 5/2008 | Gorden et al. |
| 7,387,271 B2 | 6/2008 | Noelle et al. |
| 7,390,780 B2 | 6/2008 | Huang et al. |
| 7,427,629 B2 | 9/2008 | Kedl et al. |
| 7,462,354 B2 | 12/2008 | Sette et al. |
| 7,501,134 B2 | 3/2009 | O'Hagan et al. |
| 7,517,520 B2 | 4/2009 | Manolova et al. |
| 7,550,441 B2 | 6/2009 | Farokhzad et al. |
| 7,566,703 B2 | 7/2009 | Krieg et al. |
| 7,727,969 B2 | 6/2010 | Farokhzad |
| 7,776,620 B2 | 8/2010 | Ennifar et al. |
| 7,842,312 B2 | 11/2010 | Burgermeister et al. |
| 8,367,113 B2 | 2/2013 | Gu et al. |
| 8,629,151 B2 | 1/2014 | Zepp et al. |
| 8,652,487 B2 | 2/2014 | Maldonado et al. |
| 9,006,254 B2 | 4/2015 | Zepp et al. |
| 9,066,978 B2 | 6/2015 | Ilyinskii et al. |
| 9,265,815 B2 | 2/2016 | Fraser et al. |
| 9,289,476 B2 | 3/2016 | Fraser et al. |
| 9,289,477 B2 | 3/2016 | Fraser et al. |
| 9,295,718 B2 | 3/2016 | Fraser et al. |
| 9,764,031 B2 | 9/2017 | Ilyinskii et al. |
| 9,884,112 B2 | 2/2018 | Zepp et al. |
| 9,987,354 B2 | 6/2018 | Fraser et al. |
| 9,993,548 B2 | 6/2018 | Maldonado et al. |
| 9,994,443 B2 | 6/2018 | Zepp et al. |
| 10,004,802 B2 | 6/2018 | Kishimoto et al. |
| 2002/0055477 A1 | 5/2002 | Nest et al. |
| 2002/0197269 A1 | 12/2002 | Lingnau et al. |
| 2003/0108565 A1 | 6/2003 | Johnson et al. |
| 2003/0133988 A1 | 7/2003 | Fearon et al. |
| 2003/0138432 A1 | 7/2003 | Glazier |
| 2003/0165478 A1 | 9/2003 | Sokoll |
| 2003/0175950 A1 | 9/2003 | McSwiggen |
| 2003/0223938 A1 | 12/2003 | Nagy et al. |
| 2003/0232013 A1 | 12/2003 | Sieckman et al. |
| 2004/0022840 A1 | 2/2004 | Nagy et al. |
| 2004/0038406 A1 | 2/2004 | Unger et al. |
| 2004/0059094 A1 | 3/2004 | Bachmann et al. |
| 2004/0067503 A1 | 4/2004 | Tan et al. |
| 2004/0092470 A1 | 5/2004 | Leonard et al. |
| 2004/0141958 A1 | 7/2004 | Steinaa et al. |
| 2004/0142887 A1 | 7/2004 | Cui et al. |
| 2004/0156846 A1 | 8/2004 | Daum et al. |
| 2004/0191215 A1 | 9/2004 | Froix et al. |
| 2004/0192626 A1 | 9/2004 | McSwiggen et al. |
| 2004/0230380 A1 | 11/2004 | Chirino et al. |
| 2004/0247680 A1 | 12/2004 | Farokhzad et al. |
| 2004/0258698 A1 | 12/2004 | Wightman et al. |
| 2005/0020525 A1 | 1/2005 | McSwiggen et al. |
| 2005/0032733 A1 | 2/2005 | McSwiggen et al. |
| 2005/0037075 A1 | 2/2005 | Farokhzad et al. |
| 2005/0042298 A1 | 2/2005 | Pardridge et al. |
| 2005/0048063 A1 | 3/2005 | Ruoslahti et al. |
| 2005/0074812 A1 | 4/2005 | Ruoslahti et al. |
| 2005/0107322 A1 | 5/2005 | O'Hagan et al. |
| 2005/0113697 A1 | 5/2005 | Ottononi et al. |
| 2005/0158390 A1 | 7/2005 | Rana et al. |
| 2005/0163745 A1 | 7/2005 | Sokoll et al. |
| 2005/0191294 A1 | 9/2005 | Arap et al. |
| 2005/0192248 A1 | 9/2005 | Tsuji et al. |
| 2005/0196806 A1 | 9/2005 | Schlom et al. |
| 2005/0239734 A1 | 10/2005 | Uhlmann et al. |
| 2005/0244504 A1 | 11/2005 | Little et al. |
| 2006/0002852 A1 | 1/2006 | Saltzman et al. |
| 2006/0002995 A1 | 1/2006 | Harwigsson |
| 2006/0051317 A1 | 3/2006 | Batrakova et al. |
| 2006/0073114 A1 | 4/2006 | Grainger et al. |
| 2006/0093617 A1 | 5/2006 | Buyse et al. |
| 2006/0111271 A1 | 5/2006 | Cerny et al. |
| 2006/0142202 A1 | 6/2006 | Alkan et al. |
| 2006/0173339 A1 | 8/2006 | Tomes et al. |
| 2006/0189554 A1 | 8/2006 | Mumper et al. |
| 2006/0222652 A1 | 10/2006 | Sebbel et al. |
| 2006/0241076 A1 | 10/2006 | Uhlmann et al. |
| 2006/0257359 A1 | 11/2006 | Francois et al. |
| 2007/0014804 A1 | 1/2007 | Burkhard |
| 2007/0014807 A1 | 1/2007 | Maida, III |
| 2007/0087986 A1 | 4/2007 | Premack et al. |
| 2007/0098713 A1 | 5/2007 | Unger et al. |
| 2007/0116768 A1 | 5/2007 | Chorny et al. |
| 2007/0166384 A1 | 7/2007 | Zarraga et al. |
| 2007/0184068 A1 | 8/2007 | Renner et al. |
| 2007/0292386 A9 | 12/2007 | Campbell et al. |
| 2008/0014144 A1 | 1/2008 | Saltzman et al. |
| 2008/0014281 A1 | 1/2008 | Shibata et al. |
| 2008/0031899 A1 | 2/2008 | Reddy et al. |
| 2008/0044484 A1 | 2/2008 | Minev |
| 2008/0064859 A1 | 3/2008 | Vandenbark et al. |
| 2008/0081074 A1 | 4/2008 | Gu et al. |
| 2008/0145441 A1 | 6/2008 | Penades et al. |
| 2008/0160089 A1 | 7/2008 | Vitiello et al. |
| 2008/0171059 A1 | 7/2008 | Howland et al. |
| 2008/0207550 A1 | 8/2008 | Fearon et al. |
| 2008/0213377 A1 | 9/2008 | Bhatia et al. |
| 2008/0233181 A1 | 9/2008 | Nagy et al. |
| 2008/0268063 A1 | 10/2008 | Jon et al. |
| 2008/0274131 A1 | 11/2008 | Renner et al. |
| 2008/0305161 A1 | 12/2008 | Shah et al. |
| 2008/0317784 A1 | 12/2008 | O'Hagan et al. |
| 2009/0004118 A1 | 1/2009 | Nie et al. |
| 2009/0028910 A1 | 1/2009 | DeSimone et al. |

(56) References Cited

U.S. PATENT DOCUMENTS

| | | |
|---|---|---|
| 2009/0053293 A1 | 2/2009 | Liang et al. |
| 2009/0074828 A1 | 3/2009 | Alexis et al. |
| 2009/0104268 A1 | 4/2009 | Himmler et al. |
| 2009/0155292 A1 | 6/2009 | Santamaria et al. |
| 2009/0169636 A1 | 7/2009 | O'Hagan et al. |
| 2009/0226525 A1 | 9/2009 | de los Rios et al. |
| 2009/0257950 A1 | 10/2009 | Sligar et al. |
| 2009/0297609 A1 | 12/2009 | Shoichet et al. |
| 2009/0297621 A1 | 12/2009 | Lim et al. |
| 2009/0298710 A1 | 12/2009 | Farokhzad et al. |
| 2009/0325292 A1 | 12/2009 | Baker et al. |
| 2010/0022680 A1 | 1/2010 | Karnik et al. |
| 2010/0055189 A1 | 3/2010 | Hubbell et al. |
| 2010/0062968 A1 | 3/2010 | Pulendran et al. |
| 2010/0068285 A1 | 3/2010 | Zale et al. |
| 2010/0069426 A1 | 3/2010 | Zale et al. |
| 2010/0092425 A1 | 4/2010 | Von Andrian et al. |
| 2010/0099613 A1 | 4/2010 | Buyse et al. |
| 2010/0111973 A1 | 5/2010 | Dranoff et al. |
| 2010/0111993 A1 | 5/2010 | Tureci et al. |
| 2010/0129392 A1 | 5/2010 | Shi et al. |
| 2010/0129439 A1 | 5/2010 | Alexis et al. |
| 2010/0144845 A1 | 6/2010 | Farokhzad et al. |
| 2010/0151000 A1 | 6/2010 | Thomas et al. |
| 2010/0160299 A1 | 6/2010 | Baker et al. |
| 2010/0172993 A1 | 7/2010 | Singh et al. |
| 2010/0183727 A1 | 7/2010 | Iannacone et al. |
| 2010/0189742 A1 | 7/2010 | Van Der Burg et al. |
| 2010/0196482 A1 | 8/2010 | Radovic-Moreno et al. |
| 2010/0203142 A1 | 8/2010 | Zhang et al. |
| 2010/0233251 A1 | 9/2010 | Von Andrian et al. |
| 2010/0266491 A1 | 10/2010 | Farokhzad et al. |
| 2010/0297233 A1 | 11/2010 | Moretti et al. |
| 2010/0303723 A1 | 12/2010 | Farokhzad et al. |
| 2010/0303850 A1 | 12/2010 | Lipford et al. |
| 2010/0323019 A1 | 12/2010 | Lim et al. |
| 2010/0323199 A1 | 12/2010 | Gu et al. |
| 2011/0008435 A1 | 1/2011 | Devane et al. |
| 2011/0020388 A1 | 1/2011 | Zepp et al. |
| 2011/0027217 A1 | 2/2011 | Zepp et al. |
| 2011/0045046 A1 | 2/2011 | Franco |
| 2011/0052697 A1 | 3/2011 | Farokhzad et al. |
| 2011/0070154 A1 | 3/2011 | Hyde et al. |
| 2011/0104293 A1* | 5/2011 | Pulendran et al. ............ 424/490 |
| 2011/0110965 A1 | 5/2011 | Fraser et al. |
| 2011/0151015 A1 | 6/2011 | Hubby et al. |
| 2011/0171248 A1 | 7/2011 | Pittet et al. |
| 2011/0223201 A1 | 9/2011 | Lipford et al. |
| 2011/0229556 A1 | 9/2011 | Irvine et al. |
| 2011/0262491 A1 | 10/2011 | Keegan et al. |
| 2011/0272836 A1 | 11/2011 | Keegan et al. |
| 2011/0293700 A1 | 12/2011 | Bratzler et al. |
| 2011/0293701 A1 | 12/2011 | Bratzler et al. |
| 2011/0293723 A1 | 12/2011 | Bratzler et al. |
| 2011/0294717 A1 | 12/2011 | Ali et al. |
| 2011/0312877 A1* | 12/2011 | Berninger et al. ............ 514/3.3 |
| 2012/0027806 A1 | 2/2012 | Ilyinskii et al. |
| 2012/0058153 A1 | 3/2012 | Ilyinskii et al. |
| 2012/0058154 A1 | 3/2012 | Ilyinskii et al. |
| 2012/0064110 A1 | 3/2012 | Ilyinskii et al. |
| 2012/0070493 A1 | 3/2012 | Fraser et al. |
| 2012/0114677 A1 | 5/2012 | Zepp et al. |
| 2012/0171229 A1 | 7/2012 | Zepp et al. |
| 2012/0244222 A1 | 9/2012 | Altreuter et al. |
| 2012/0276109 A1 | 11/2012 | Fraser et al. |
| 2012/0276133 A1 | 11/2012 | Maldonado et al. |
| 2012/0276134 A1 | 11/2012 | Fraser et al. |
| 2012/0276155 A1 | 11/2012 | Kishimoto et al. |
| 2012/0276156 A1 | 11/2012 | Fraser et al. |
| 2012/0276157 A1 | 11/2012 | Fraser et al. |
| 2012/0276158 A1 | 11/2012 | Fraser et al. |
| 2012/0276159 A1 | 11/2012 | Fraser et al. |
| 2012/0276160 A1 | 11/2012 | Maldonado et al. |
| 2012/0294888 A1 | 11/2012 | Kishimoto et al. |
| 2012/0301498 A1 | 11/2012 | Altreuter et al. |
| 2012/0301510 A1 | 11/2012 | Kishimoto et al. |
| 2013/0028857 A1 | 1/2013 | Gao et al. |
| 2013/0039954 A1 | 2/2013 | Pittet et al. |
| 2013/0058894 A1 | 3/2013 | Maldonado et al. |
| 2013/0058901 A1 | 3/2013 | Maldonado et al. |
| 2013/0058902 A1 | 3/2013 | Kishimoto et al. |
| 2013/0058963 A1 | 3/2013 | Maldonado et al. |
| 2013/0058970 A1 | 3/2013 | Kishimoto et al. |
| 2013/0058974 A1 | 3/2013 | Maldonado et al. |
| 2013/0058975 A1 | 3/2013 | Maldonado et al. |
| 2013/0058976 A1 | 3/2013 | Kishimoto et al. |
| 2013/0058977 A1 | 3/2013 | Maldonado et al. |
| 2013/0058978 A1 | 3/2013 | Maldonado et al. |
| 2013/0059009 A1 | 3/2013 | Kishimoto et al. |
| 2014/0030344 A1 | 1/2014 | Zepp et al. |
| 2014/0193453 A1 | 7/2014 | Zepp et al. |
| 2014/0199340 A1 | 7/2014 | Maldonado |
| 2014/0242173 A1 | 8/2014 | Zepp et al. |
| 2014/0328854 A1 | 11/2014 | Maldonado et al. |
| 2014/0328921 A1 | 11/2014 | Maldonado |
| 2014/0328922 A1 | 11/2014 | Maldonado |
| 2014/0328923 A1 | 11/2014 | Maldonado et al. |
| 2014/0328924 A1 | 11/2014 | Kishimoto |
| 2014/0335186 A1 | 11/2014 | Kishimoto et al. |
| 2014/0356361 A1 | 12/2014 | Maldonado et al. |
| 2015/0320728 A1 | 11/2015 | Fraser et al. |
| 2015/0320856 A1 | 11/2015 | Altreuter et al. |
| 2015/0320870 A1 | 11/2015 | Maldonado |
| 2015/0320884 A1 | 11/2015 | Fraser et al. |
| 2015/0328300 A1 | 11/2015 | Zepp et al. |
| 2015/0328309 A1 | 11/2015 | Ilyinskii et al. |
| 2015/0328333 A1 | 11/2015 | Fraser et al. |
| 2015/0335762 A1 | 11/2015 | Fraser et al. |
| 2015/0359865 A1 | 12/2015 | Kishimoto |
| 2015/0374815 A1 | 12/2015 | Kishimoto et al. |
| 2016/0022650 A1 | 1/2016 | Fraser et al. |
| 2016/0030554 A1 | 2/2016 | Kishimoto et al. |
| 2016/0030555 A1 | 2/2016 | Kishimoto et al. |
| 2016/0067228 A1 | 3/2016 | Kishimoto |
| 2016/0074372 A1 | 3/2016 | Kishimoto |
| 2016/0074427 A1 | 3/2016 | Kishimoto |
| 2016/0074531 A1 | 3/2016 | Kishimoto |
| 2016/0074532 A1 | 3/2016 | Kishimoto |
| 2016/0128986 A1 | 5/2016 | O'Neil et al. |
| 2016/0128987 A1 | 5/2016 | Griset et al. |
| 2016/0220501 A1 | 8/2016 | Fraser et al. |
| 2016/0243253 A1 | 8/2016 | Fraser et al. |
| 2016/0256401 A1 | 9/2016 | Fraser et al. |
| 2016/0279234 A1 | 9/2016 | Kishimoto et al. |
| 2017/0258927 A1 | 9/2017 | Johnston |
| 2017/0349433 A1 | 12/2017 | Lipford et al. |
| 2018/0043023 A1 | 2/2018 | Ilyinski et al. |
| 2018/0071394 A1 | 3/2018 | O'Neil et al. |
| 2018/0085319 A1 | 3/2018 | Kishimoto |

FOREIGN PATENT DOCUMENTS

| | | |
|---|---|---|
| EP | 1 221 955 B9 | 11/2005 |
| EP | 1 752 141 A1 | 2/2007 |
| WO | WO 95/22963 A1 | 8/1995 |
| WO | WO 96/20698 A2 | 7/1996 |
| WO | WO 97/04747 A1 | 2/1997 |
| WO | WO 97/41440 A1 | 11/1997 |
| WO | WO 98/37919 A1 | 9/1998 |
| WO | WO 98/40100 A1 | 9/1998 |
| WO | WO 98/52581 A1 | 11/1998 |
| WO | WO 99/56755 A1 | 11/1999 |
| WO | WO 00/06123 A1 | 2/2000 |
| WO | WO 00/27363 A1 | 5/2000 |
| WO | WO 00/32227 A2 | 6/2000 |
| WO | WO 00/32626 A1 | 6/2000 |
| WO | WO 00/50075 A2 | 8/2000 |
| WO | WO 01/68103 A2 | 9/2001 |
| WO | WO 01/85208 A2 | 11/2001 |
| WO | WO 02/32450 A2 | 4/2002 |
| WO | WO 02/56905 A2 | 7/2002 |
| WO | WO 02/56907 A2 | 7/2002 |
| WO | WO 2003/039225 A2 | 5/2003 |
| WO | WO 2003/040164 A2 | 5/2003 |

(56) References Cited

FOREIGN PATENT DOCUMENTS

| WO | WO 2003/086280 A2 | 10/2003 |
|---|---|---|
| WO | WO 2004/007538 A2 | 1/2004 |
| WO | WO 2004/016282 A1 | 2/2004 |
| WO | WO 2004/022594 A2 | 3/2004 |
| WO | WO 2004/030608 A2 | 4/2004 |
| WO | WO 2004/053104 A2 | 6/2004 |
| WO | WO 2004/058179 A2 | 7/2004 |
| WO | WO 2004/071493 A1 | 8/2004 |
| WO | WO 2004/084871 A1 | 10/2004 |
| WO | WO 2004/098509 A2 | 11/2004 |
| WO | WO 2005/014110 A1 | 2/2005 |
| WO | WO 2005/042018 A2 | 5/2005 |
| WO | WO 2005/097993 A2 | 10/2005 |
| WO | WO 2005/108425 A1 | 11/2005 |
| WO | WO 2005/110013 A2 | 11/2005 |
| WO | WO 2005/120574 A1 | 12/2005 |
| WO | WO 2006/031878 A2 | 3/2006 |
| WO | WO 2006/037979 A2 | 4/2006 |
| WO | WO 2006/045796 A2 | 5/2006 |
| WO | WO 2006/045849 A1 | 5/2006 |
| WO | WO 2006/063974 A2 | 6/2006 |
| WO | WO 2006/066158 A2 | 6/2006 |
| WO | WO 2006/102395 A2 | 9/2006 |
| WO | WO 2006/117217 A2 | 11/2006 |
| WO | WO 2006/135434 A2 | 12/2006 |
| WO | WO 2006/137934 A2 | 12/2006 |
| WO | WO 2007/001448 A2 | 1/2007 |
| WO | WO 2007/003054 A1 | 1/2007 |
| WO | WO 2007/019678 A1 | 2/2007 |
| WO | WO 2007/062107 A2 | 5/2007 |
| WO | WO 2007/068747 A1 | 6/2007 |
| WO | WO 2007/070682 A2 | 6/2007 |
| WO | WO 2007/089870 A2 | 8/2007 |
| WO | WO 2007/098254 A2 | 8/2007 |
| WO | WO 2007/109810 A2 | 9/2007 |
| WO | WO 2007/118653 A2 | 10/2007 |
| WO | WO 2007/133807 A2 | 11/2007 |
| WO | WO 2007/137117 A2 | 11/2007 |
| WO | WO 2007/144150 A1 | 12/2007 |
| WO | WO 2007/149802 A2 | 12/2007 |
| WO | WO 2007/150030 A2 | 12/2007 |
| WO | WO 2008/033432 A2 | 3/2008 |
| WO | WO 2008/051245 A2 | 5/2008 |
| WO | WO 2008/071774 A1 | 6/2008 |
| WO | WO 2008/079924 A1 | 7/2008 |
| WO | WO 2008/093173 A1 | 8/2008 |
| WO | WO 2008/105773 A2 | 9/2008 |
| WO | WO 2008/115319 A2 | 9/2008 |
| WO | WO 2008/115641 A2 | 9/2008 |
| WO | WO 2008/019142 A2 | 10/2008 |
| WO | WO 2008/118861 A2 | 10/2008 |
| WO | WO 2008/121926 A1 | 10/2008 |
| WO | WO 2008/124632 A1 | 10/2008 |
| WO | WO 2008/124634 A1 | 10/2008 |
| WO | WO 2008/124639 A2 | 10/2008 |
| WO | WO 2008/127532 A1 | 10/2008 |
| WO | WO 2008/129020 A1 | 10/2008 |
| WO | WO 2008/143709 A2 | 11/2008 |
| WO | WO 2008/147456 A2 | 12/2008 |
| WO | WO 2009/022154 A2 | 2/2009 |
| WO | WO 2009/051837 A2 | 4/2009 |
| WO | WO 2009/076158 A1 | 6/2009 |
| WO | WO 2009/106999 A2 | 9/2009 |
| WO | WO 2009/108822 A1 | 9/2009 |
| WO | WO 2009/109428 A2 | 9/2009 |
| WO | WO 2009/111588 A1 | 9/2009 |
| WO | WO 2008/157419 A2 | 12/2009 |
| WO | WO 2010/003009 A1 | 1/2010 |
| WO | WO 2010/017330 A1 | 2/2010 |
| WO | WO 2010/018130 A1 | 2/2010 |
| WO | WO 2010/018131 A1 | 2/2010 |
| WO | WO 2010/018132 A1 | 2/2010 |
| WO | WO 2010/018133 A1 | 2/2010 |
| WO | WO 2010/018384 A1 | 2/2010 |
| WO | WO 2010/025324 A2 | 3/2010 |
| WO | WO 2010/037402 A1 | 4/2010 |
| WO | WO 2010/042863 A1 | 4/2010 |
| WO | WO 2010/042866 A1 | 4/2010 |
| WO | WO 2010/042870 A1 | 4/2010 |
| WO | WO 2010/042876 A1 | 4/2010 |
| WO | WO 2010/115046 A2 | 10/2010 |
| WO | WO 2010/123569 A2 | 10/2010 |
| WO | WO 2010/138192 A2 | 12/2010 |
| WO | WO 2010/138193 A2 | 12/2010 |
| WO | WO 2010/138194 A2 | 12/2010 |
| WO | WO 2011/005850 A1 | 1/2011 |

OTHER PUBLICATIONS

Alexander et al., Universal influenza DNA vaccine encoding conserved CD4+ T cell epitopes protects against lethal viral challenge in HLA-DR transgenic mice. Vaccine. Jan. 8, 2010;28(3):664-72. Epub Nov. 4, 2009.

Alexis et al., Factors affecting the clearance and biodistribution of polymeric nanoparticles. Mol Pharm. Jul.-Aug. 2008;5(4):505-15. Epub Aug. 4, 2008.

Allen et al., Nano-engineering block copolymer aggregates for drug delivery. Colloids Surfaces B-Biointerfaces. 1999;16:3-27.

Allison, The mode of action of immunological adjuvants. Dev Biol Stand. 1998;92:3-11.

Anderson et al., Delivery Systems for Immunomodulatory Proteins and Peptides. BioDrugs. Jan. 1997;7(1):51-65.

Anikeeva et al., Quantum dot/peptide-MHC biosensors reveal strong CD8-dependent cooperation between self and viral antigens that augment the T cell response. Proc Natl Acad Sci U S A. Nov. 7, 2006;103(45):16846-51. Epub Oct. 31, 2006.

Asano et al., Targeting activated lymphocytes with lipid microsphere containing a cytotoxic agent; efficacy of immunosuppression with a new drug delivery system. J Urology. 2001;165(5)384. Abstact 1571.

Astete et al., Synthesis and characterization of PLGA nanoparticles. J Biomat Sci. 2006;17:247-89.

Ataman-Onal et al., Surfactant-free anionic PLA nanoparticles coated with HIV-1 p24 protein induced enhanced cellular and humoral immune responses in various animal models. J Control Release. May 15, 2006;112(2):175-85. Epub Mar. 6, 2006.

Avgoustakis, Pegylated poly(lactide) and poly(lactide-co-glycolide) nanoparticles: preparation, properties and possible applications in drug delivery. Curr Drug Deliv. Oct. 2004;1(4):321-33.

Bachmann et al., T helper cell-independent neutralizing B cell response against vesicular stomatitis virus: role of antigen patterns in B cell induction?. Eur J Immunol. 1995;25(12):3445-51.

Badiee et al., Coencapsulation of CpG oligodeoxynucleotides with recombinant Leishmania major stress-inducible protein 1 in liposome enhances immune response and protection against leishmaniasis in immunized BALB/c mice. Clin Vaccine Immunol. Apr. 2008;15(4):668-74. Epub Jan. 30, 2008.

Bae et al., Mixed polymeric micelles for combination cancer chemotherapy through the concurrent delivery of multiple chemotherapeutic agents. J Control Release. Oct. 8, 2007;122(3):324-30. Epub Jun. 13, 2007.

Bagalkot et al., An Aptamer-Doxorubicin Physical Conjugate as a Novel Targeted Drug-Delivery Platform. Angew Chem Int. 2006;45(48):8149-52.

Bala et al., PLGA nanoparticles in drug delivery: the state of the art. Crit Rev Ther Drug Carrier Syst. 2004;21(5):387-422.

Barchet et al., Virus-induced interferon alpha production by a dendritic cell subset in the absence of feedback signaling in vivo. J Exp Med. 2002;195(4):507-16.

Barichello et al., Encapsulation of hydrophilic and lipophilic drugs in PLGA nanoparticles by the nanoprecipitation method. Drug Dev Ind Pharm. Apr. 1999;25(4):471-6.

Barve et al., Induction of immune responses and clinical efficacy in a phase II trial of IDM-2101, a 10-epitope cytotoxic T-lymphocyte vaccine, in metastatic non-small-cell lung cancer. J Clin Oncol. Sep. 20, 2008;26(27):4418-25.

Batista et al., The who, how and where of antigen presentation to B cells. Nat Rev Immunol. Jan. 2009;9(1):15-27.

(56) References Cited

OTHER PUBLICATIONS

Bauer et al., Human TLR9 confers responsiveness to bacterial DNA via species-specific CpG motif recognition. Proc Natl Acad Sci U S A. Jul. 31, 2001;98(16):9237-42. Epub Jul. 24, 2001.

Bayard et al., Hepatitis B virus (HBV)-derived DRB1*0101-restricted CD4 T-cell epitopes help in the development of HBV-specific CD8+ T cells in vivo. Vaccine. May 14, 2010;28(22):3818-26. Epub Mar. 31, 2010.

Beaurepaire et al., Functionalized Fluorescent Oxide Nanoparticles: Artificial Toxins for Sodium Channel Targeting and Imaging at the Single-Molecule Level. Nano Letters. 2004;4(11):2079-83.

Bei et al., "TAA polyepitope DNA-based vaccines: A potential tool for cancer therapy." J Biomed Biotech. 2010; 102758:1-12.

Bharali, Micro-and Nanoparticles-Based Vaccines for Hepatitis B. Immune-Mediated Diseases. 2007:415-21.

Blanco-Prieto et al., Slow delivery of the selective cholecystokinin agonist pBC 264 into the rat nucleus accumbens using microspheres. J Neurochem. Dec. 1996;67(6):2417-24.

Blander, Phagocytosis and antigen presentation: a partnership initiated by Toll-like receptors. Ann Rheum Dis. Dec. 2008;67 Suppl 3:iii44-9.

Boden et al., Regulatory T cells in inflammatory bowel disease. Curr Opin Gastroenterol. Nov. 2008;24(6):733-41.

Boes et al., T-cell engagement of dendritic cells rapidly rearranges MHC class II transport. Nature. 418(6901):983-988 (2002).

Bonifaz et al., Efficient targeting of protein antigen to the dendritic cell receptor DEC-205 in the steady state leads to antigen presentation on major histocompatibility complex class I products and peripheral CD8+ T cell tolerance. J Exp Med. 2002;196(12):1627-38.

Borges et al., Evaluation of the immune response following a short oral vaccination schedule with hepatitis B antigen encapsulated into alginate-coated chitosan nanoparticles. Eur J Pharm Sci. Dec. 2007;32(4-5):278-90. Epub Aug. 15, 2007.

Bourquin et al., Targeting CpG oligonucleotides to the lymph node by nanoparticles elicits efficient antitumoral immunity. J Immunol. Sep. 1, 2008;181(5):2990-8.

Boussif et al., A versatile vector for gene and oligonucleotide transfer into cells in culture and in vivo: polyethylenimine. Proc Natl Acad Sci. USA. 1995;92:7297-301.

Bozzacco et al., DEC-205 receptor on dendritic cells mediates presentation of HIV gag protein to CD8+ T cells in a spectrum of human MHC I haplotypes. Proc Natl Acad Sci USA. 2007;104(4):1289-94.

Brito et al., Nanoparticulate carriers for the treatment of coronary restenosis. Int J Nanomedicine. 2007;2(2):143-61.

Bullis, Shape Matters for Nanoparticles. Technology Review. Aug. 7, 2008. 2 pages.

Bundy et al., *Escherichia coli*-based cell-free synthesis of virus-like particles. Biotechnol Bioeng. May 1, 2008;100(1):28-37.

Busson et al., Prediction of CD4(+) T cell epitopes restricted to HLA-DP4 molecules. J Immunol Methods. Dec. 20, 2006;317(1-2):144-51. Epub Oct. 26, 2006.

Cameron et al., Aliphatic polyester polymer stars: synthesis, properties and applications in biomedicine and nanotechnology. Chem Soc Rev. Mar. 2011;40(3):1761-76.

Carino et al., Nanosphere based oral insulin delivery. J Control Release. 2000;65(1-2):261-9.

Carrasco et al., B cells acquire particulate antigen in a macrophage-rich area at the boundary between the follicle and the subcapsular sinus of the lymph node. Immunity. Jul. 2007;27(1):160-71. Epub Jul. 19, 2007.

Castelli et al., HLA-DP4, the most frequent HLA II molecule, defines a new supertype of peptide-binding specificity. J Immunol. Dec. 15, 2002;169(12):6928-34.

Cerritelli et al., PEG-SS-PPS: reduction-sensitive disulfide block copolymer vesicles for intracellular drug delivery. Biomacromolecules. Jun. 2007;8(6):1966-72. Epub May 12, 2007.

Chacón et al., Optimized preparation of poly D,L (lactic-glycolic) microspheres and nanoparticles for oral administration. Intl J Pharmaceutics. 1996;141:81-91.

Chapoval et al., HLA-DQ6 and HLA-DQ8 transgenic mice respond to ragweed allergens and recognize a distinct set of epitopes on short and giant ragweed group 5 antigens. J Immunol. Aug. 15, 1998;161(4):2032-7.

Cheng et al., Formulation of functionalized PLGA-PEG nanoparticles for in vivo targeted drug delivery. Biomaterials. 2007;28(5):869-76.

Chengalvala et al., Enhanced immunogenicity of hepatitis B surface antigen by insertion of a helper T cell epitope from tetanus toxoid. Vaccine. Mar. 5, 1999;17(9-10):1035-41.

Chinen et al., Basic and clinical immunology. J Allergy Clin Immunol. Aug. 2005;116(2):411-8.

Chu et al., Aptamer mediated siRNA delivery. Nuc Acid Res. 2006;34:e73.

Chu et al., CpG oligodeoxynucleotides act as adjuvants that switch on T helper 1 (Th1) immunity. J Exp Med. Nov. 17, 1997;186(10):1623-31.

Chu et al., Labeling tumor cells with fluorescent nanocrystal-aptamer bioconjugates. Biosens Bioelectron. 2006;21:1859-66.

Chukwu et al., Loading some psychopharmacologic agents onto poly(butylcynoacrylate) nanoparticles—a means for targeting agents to the brain and improving therapeutic efficiency. Proc Int'l Symp Control Rd Bioact Mat. 1999:1148-9.

Clark, The reticulum of lymph nodes in mice studied with the electron microscope. Am J Anat. 1962;110:217-57.

Connor et al., Ex vivo evaluation of anti-EpCAM immunocytokine huKS-IL2 in ovarian cancer. J Immunother. 2004;27(3):211-19.

Conti et al., Thymopentin loaded microsphere preparation by w/o/w emulsion technique: in vitro/ex vivo evaluation. J Microencapsul. May-Jun. 1997;14(3):303-10.

Croy et al., Polymeric micelles for drug delivery. Curr Pharm Design. 2006;12:4669-84.

Cruz et al., The influence of PEG chain length and targeting moiety on antibody-mediated delivery of nanoparticle vaccines to human dendritic cells. Biomaterials. Oct. 2011;32(28):6791-803. Epub Jul. 2, 2011. E-pub version.

Cvetanovich et al., Human regulatory T cells in autoimmune diseases. Curr Opin Immunol. Dec. 2010;22(6):753-60. Epub Sep. 24, 2010.

Czarniecki, Small molecule modulators of toll-like receptors. J Med Chem. Nov. 13, 2008;51(21):6621-6. doi: 10.1021/jm800957k. Epub Oct. 2, 2008.

Dakappagari et al., A chimeric multi-human epidermal growth factor receptor-2 B cell epitope peptide vaccine mediates superior antitumor responses. J Immunol. Apr. 15, 2003;170(8):4242-53.

Davis et al., CpG DNA is a potent enhancer of specific immunity in mice immunized with recombinant hepatitis B surface antigen. J Immunol. Jan. 15, 1998;160(2):870-6.

De Gregorio et al., Alum adjuvanticity: unraveling a century old mystery. Eur J Immunol. Aug. 2008;38(8):2068-71.

De Jaeghere et al., Freeze-drying and lyopreservation of diblock and triblock poly(lactic acid)-poly(ethylene oxide) (PLA-PEO) copolymer nanoparticles. Pharm Dev Technol. 2000;5(4):473-83.

De La Fuente et al., Novel hyaluronan-based nanocarriers for transmucosal delivery of macromolecules. Macromol Biosci. May 13, 2008;8(5):441-50.

Delemarre et al., Repopulation of macrophages in popliteal lymph nodes of mice after liposome-mediated depletion. J Leukoc Biol. 1990;47(3):251-7.

Demangel et al., Single chain antibody fragments for the selective targeting of antigens to dendritic cells. Mol Immunol. May 2005;42(8):979-85. Epub Dec. 10, 2004.

Demello et al., Microscale reactors: nanoscale products. Lab on a Chip. 2004;4(2):11N-15N.

Demello, Control and detection of chemical reactions in microfluidic systems. Nature. 2006;442(7100):394-402.

Deming, Facile synthesis of block copolypeptides of defined architecture. Nature. 1997;390(6658):386-9.

Depla et al., Rational design of a multiepitope vaccine encoding T-lymphocyte epitopes for treatment of chronic hepatitis B virus infections. J Virol. Jan. 2008;82(1):435-50. Epub Oct. 17, 2007.

(56) References Cited

OTHER PUBLICATIONS

Derfus et al., Intracellular Delivery of Quantum Dots for Live Cell Labeling and Organelle Tracking. Adv Mat. 2004;16:961-6.
Diethelm-Okita et al., Universal epitopes for human CD4+ cells on tetanus and diphtheria toxins. J Infect Dis. Mar. 2000;181(3):1001-9.
Ding et al., Multiepitope peptide-loaded virus-like particles as a vaccine against hepatitis B virus-related hepatocellular carcinoma. Hepatology. May 2009;49(5):1492-502.
Diwan et al., Dose sparing of CpG oligodeoxynucleotide vaccine adjuvants by nanoparticle delivery. Curr Drug Deliv. Oct. 2004;1(4):405-12.
Diwan et al., Enhancement of immune responses by co-delivery of a CpG oligodeoxynucleotide and tetanus toxoid in biodegradable nanospheres. J Control Release. Dec. 13, 2002;85(1-3):247-62.
Donbrow, Ed., Microcapsules and Nanoparticles in Medicine and Pharmacy. CRC Press, Boca Raton, 1992.
Dou et al., Development of a macrophage-based nanoparticle platform for antiretroviral drug delivery. Blood. Oct. 15, 2006;108(8):2827-35. Epub Jun. 29, 2006. Erratum in: Blood. Mar. 1, 2007;109(5):1816.
Elamanchili et al., "Pathogen-mimicking" nanoparticles for vaccine delivery to dendritic cells. J Immunother. May-Jun. 2007;30(4):378-95. Abstract only.
Eldridge et al., Biodegradable microspheres as a vaccine delivery system. Mol Immunol. 1991;28(3):287-94.
Farokhzad et al., Drug delivery systems in urology—getting "smarter". Urology. Sep. 2006;68(3):463-9.
Farokhzad et al., Impact of nanotechnology on drug delivery. ACS Nano. Jan. 27, 2009;3(1):16-20.
Farokhzad et al., Nanoparticle—aptamer bioconjugates for cancer targeting. Expert Opin Drug Deliv. 2006;3(3):311-24.
Farokhzad et al., Nanoparticle-Aptamer Bioconjugates: A New Approach for Targeting Prostate Cancer Cells. Cancer Research. 2004;64:7668-72.
Farokhzad et al., Targeted nanoparticle-aptamer bioconjugates for cancer chemotherapy in vivo. Proc Natl Acad Sci USA. 2006;103(16):6315-20.
Farr et al., The structure of the sinus wall of the lymph node relative to its endocytic properties and transmural cell passage. Am J Anat. 1980;157(3):265-84.
Feuillet et al., Involvement of Toll-like receptor 5 in the recognition of flagellated bacteria. Proc Natl Acad Sci U S A. Aug. 15, 2006;103(16):6315-20.Acad Sci U S a. 2006.33):12487-92. Epub Aug. 4, 2006.
Fonseca et al., Paclitaxel-loaded PLGA nanoparticles: preparation, physicochemical characterization and in vitro anti-tumoral activity. J Control Release. 2002;83(2):273-86.
Forslund et al., Nitric oxide-releasing particles inhibit phagocytosis in human neutrophils. Biochem Biophys Res Commun. Apr. 17, 1997;233(2):492-5.
Gao et al., In vivo cancer targeting and imaging with semiconductor quantum dots. Nat Biotechnol. 2004;22(8):969-76.
Gao et al., In vivo molecular and cellular imaging with quantum dots. Curr Op Biotechnol. 2005;16:63-72.
Garçon et al., Boosting vaccine power. Sci Am. Oct. 2009;301(4):72-9.
Garrett et al., Novel engineered trastuzumab conformational epitopes demonstrate in vitro and in vivo antitumor properties against HER-2/neu. J Immunol. Jun. 1, 2007;178(11):7120-31.
Gelperina et al., The potential advantages of nanoparticle drug delivery systems in chemotherapy of tuberculosis. Am J Respir Crit Care Med. Dec. 15, 2005;172(12):1487-90. Epub Sep. 8, 2005.
Getts et al., Microparticles bearing encephalitogenic peptides induce T-cell tolerance and ameliorate experimental autoimmune encephalomyelitis. Nat Biotechnol. Nov. 18, 2012. doi: 10.1038/nbt.2434. [Epub ahead of print].
Govender et al., PLGA nanoparticles prepared by nanoprecipitation: drug loading and release studies of a water soluble drug. J Control Release. Feb. 1, 1999;57(2):171-85.

Gref et al., Biodegradable long-circulating polymeric nanospheres. Science. 1994;263(5153):1600-3.
Griset et al., Expansile nanoparticles: synthesis, characterization, and in vivo efficacy of an acid-responsive polymeric drug delivery system. J Am Chem Soc. Feb. 25, 2009;131(7):2469-71. Epub Jan. 30, 2009.
Griset, Dissertation entitled: Delivery of Paclitaxel via pH-Responsive Polymeric Nanoparticles for Prevention of Lung Cancer and Mesothelioma Recurrence, Ohio State University, 2003.
Gu et al., Precise engineering of targeted nanoparticles by using self-assembled biointegrated block copolymers. Proc Natl Acad Sci U S A. Feb. 19, 2008;105(7):2586-91. Epub Feb. 13, 2008.
Gvili et al., PLGA nanoparticles for DNA vaccination-waiving complexity and increasing efficiency. Molc Ther. 2006;13:5209.
Haas et al., Sequence independent interferon-alpha induction by multimerized phosphodiester DNA depends on spatial regulation of Toll-like receptor-9 activation in plasmacytoid dendritic cells. Immunology. Feb. 2009;126(2):290-8. Epub Nov. 15, 2008.
Haddadi, Delivery of rapamycin by PLGA nanoparticles enhances its suppressive activity on dendritic cells. J Biomed Mat Res A. 2007;84A(4):885-98.
Haensler et al., Polyamidoamine cascade polymers mediate efficient transfection of cells in culture. Bioconjugate Chem. 1993;4(5):372-9.
Hamdy et al., Co-delivery of cancer-associated antigen and Toll-like receptor 4 ligand in PLGA nanoparticles induces potent CD8+ T cell-mediated anti-tumor immunity. Vaccine. Sep. 15, 2008;26(39):5046-57. Epub Aug. 3, 2008.
Hamdy et al., Pharmaceutical analysis of synthetic lipid A-based vaccine adjuvants in poly (D,L-lactic-co-glycolic acid) nanoparticle formulations. J Pharm Biomed Anal. Aug. 15, 2007;44(4):914-23. Epub Mar. 19, 2007.
Hanes et al., Polymer microspheres for vaccine delivery. Pharm Biotechnol. 1995;6:389-412.
Hangartner et al., Antiviral immune responses in gene-targeted mice expressing the immunoglobulin heavy chain of virus-neutralizing antibodies. Proc Natl Acad Sci USA. 2003;100:12883-88.
Harada et al., Supramolecular assemblies of block copolymers in aqueous media as nanocontainers relevant to biological applications. Progress Polymer Sci. 2006;31(11):949-82.
Harper et al., Efficacy of a bivalent L1 virus-like particle vaccine in prevention of infection with human papillomavirus types 16 and 18 in young women: a randomised controlled trial. Lancet. 2004;364(9447):1757-65.
Hatsukami et al., Safety and immunogenicity of a nicotine conjugate vaccine in current smokers. Clin Pharmacol Ther. Nov. 2005;78(5):456-67.
Hawiger et al., Dendritic cells induce peripheral T cell unresponsiveness under steady state conditions in vivo. J Exp Med. 2001;194(6):769-79.
Heeg et al., Structural requirements for uptake and recognition of CpG oligonucleotides. Int J Med Microbiol. Jan. 2008;298(1-2):33-8. Epub Aug. 13, 2007.
Heil et al., Species-specific recognition of single-stranded RNA via toll-like receptor 7 and 8. Science. Mar. 5, 2004;303(5663):1526-9. Epub Feb. 19, 2004.
Hemmi et al., A Toll-like receptor recognizes bacterial DNA. Nature. Dec. 7, 2006;408(6813):740-5.
Hood et al., Tumor regression by targeted gene delivery to the neovasculature. Science. Jun. 28, 2002;296(5577):2404-7.
Hruby et al., Poly (ethylene oxide)-coated polymide nanoparticles deradable by glutathione. Colloid Polym Sci. 2007;285:569-74.
Johnson et al., Mechanism for rapid self-assembly of block copolymer nanoparticles. Phys Rev Lett. 2003;91(11):118302.1-4.
Jones et al., Polymeric micelles—a new generation of colloidal drug carriers. Eur J Pharm Biopharm. Sep. 1999;48(2):101-11.
Jung et al., Tetanus Toxoid Loaded Nanoparticles from Sulfobutylated Poly(Vinyl Alcohol)-Graft-Poly(Lactide-co-Glycolide): Evaluation of Antibody Response After Oral and Nasal Application in Mice. Pharm Res. 2001;18(3):352-60.
Junt et al., Subcapsular sinus macrophages in lymph nodes clear lymph-borne viruses and present them to antiviral B cells. Nature. 2007;450:110-4. Supplemental material.

(56) References Cited

OTHER PUBLICATIONS

Kaba et al., Immune responses of mice with different genetic backgrounds to improved multiepitope, multitarget malaria vaccine candidate antigen FALVAC-1A. Clin Vaccine Immunol. Nov. 2008;15(11):1674-83. Epub Sep. 10, 2008.
Kabanov et al., DNA Complexes with Polycations for the Delivery of Genetic Material into Cells. Bioconjugate Chem. 1995;6(1):7-20.
Kamentsky, Laser scanning cytometry. Methods Cell Biol. 2001;63:51-87.
Kanchan et al., Interactions of antigen-loaded polylactide particles with macrophages and their correlation with the immune response. Biomaterials. Dec. 2007;28(35):5344-57. Epub Sep. 7, 2007.
Karrer et al., on the key role of secondary lymphoid organs in antiviral immune responses studied in alymphoplastic (aly/aly) and spleenless (Hox11(-)/-) mutant mice. J Exp Med. 1997;185(12):2157-70.
Kelly et al., The Optical Properties of Metal Nanoparticles: The Influence of Size, Shape, and Dielectric Environment. J Phys Chem B. 2003;107(3):668-77.
Khan et al., A systematic bioinformatics approach for selection of epitope-based vaccine targets. Cell Immunol. Dec. 2006;244(2):141-7. Epub Apr. 16, 2007.
Kim et al., Enhancement of DNA vaccine potency through coadministration of CIITA DNA with DNA vaccines via gene gun. J Immunol. May 15, 2008;180(10):7019-27.
Kim et al., Inhibition of follicular T-helper cells by CD8(+) regulatory T cells is essential for self tolerance. Nature. Sep. 16, 2010;467(7313):328-32.
Kimura et al., Binding of oligoguanylate to scavenger receptors is required for oligonucleotides to augment NK cell activity and induce IFN. J Biochem. Nov. 1994;116(5):991-4.
Konan et al., Preparation and characterization of sterile sub-200 nm meso-tetra(4-hydroxylphenyl)porphyrin-loaded nanoparticles for photodynamic therapy. Eur J Pharm Biopharm. Jan. 2003;55(1):115-24.
Krieg et al., CpG motifs in bacterial DNA trigger direct B-cell activation. Nature. 1995;374(6522):546-9.
Kukowska-Latallo et al., Efficient transfer of genetic material into mammalian cells using Starburst polyamidoarnine dendrimers. Proc Natl Acad Sci USA. 1996;93(10):4897-902.
Labhasetwar et al., Arterial uptake of biodegradable nanoparticles: Effect of surface modifications. J Pharm Sci. 1998;87(10):1229-34.
Lairmore et al., Human T-lymphotropic virus type 1 peptides in chimeric and multivalent constructs with promiscuous T-cell epitopes enhance immunogenicity and overcome genetic restriction. J Virol. Oct. 1995;69(10):6077-89.
Lamalle-Bernard et al., Coadsorption of HIV-1 p24 and gp120 proteins to surfactant-free anionic PLA nanoparticles preserves antigenicity and immunogenicity. J Control Release. Sep. 28, 2006;115(1):57-67. Epub Jul. 13, 2006.
Langer, Biomaterials in drug delivery and tissue engineering: one laboratory's experience. Acc Chem Res. 2000;33(2):94-101.
Langer, New methods of drug delivery. Science. 1990;249(4976):1527-33.
Langer, Selected advances in drug delivery and tissue engineering. J Control Release. 1999;62:7-11.
Lee et al., Adaptations of nanoscale viruses and other protein cages for medical applications. Nanomedicine. Sep. 2006;2(3):137-49.
Leopold et al., Fluorescent virions: dynamic tracking of the pathway of adenoviral gene transfer vectors in living cells. Hum Gene Ther. 1998;9(3):367-78.
Leucuta et al., Albumin microspheres as a drug delivery system for epirubicin: pharmaceutical, pharmacokinetic and biological aspects. Int J Phar. 1988;41:213-7.
Liang et al., Activation of human B cells by phosphorothioate oligodeoxynucleotides. J Clin Invest. Sep. 1, 1996;98(5):1119-29.
Liang et al., Paclitaxel-Loaded Poly(γ-glutamic acid)-poly(lactide) Nanoparticles as a Targeted Drug Delivery System against Cultured HepG2 Cells. Bioconjug Chem. Mar.-Apr. 2006;17(2):291-9. E-pub ahead of print. E-pub version.

Lim et al., A Self-Destroying Polycationic Polymer: Biodegradable Poly(4-hydroxy-L-¬proline ester). J Am Chem Soc. 1999;121(24):5633-9.
Lim et al., Cationic hyperbranched poly(amino ester): a novel class of DNA condensing molecule with cationic surface, biodegradable three-dimensional structure, and tertiary amine groups in the interior. J Am Chem Soc. Mar. 14, 2001;123(10):2460-1.
Lin et al., Well-Ordered Mesoporous Silica Nanoparticles as Cell Markers. Chem Mater. 2005;17:4570-3.
Lindblad, Aluminium compounds for use in vaccines. Immunol Cell Biol. Oct. 2004;82(5):497-505.
Lipford et al., Bacterial DNA as immune cell activator. Trends Microbiol. Dec. 1998;6(12):496-500.
Lipford et al., CpG-containing synthetic oligonucleotides promote B and cytotoxic T cell responses to protein antigen: a new class of vaccine adjuvants. Eur J Immunol. Sep. 1997;27(9):2340-4.
Livingston et al., A rational strategy to design multiepitope immunogens based on multiple Thlymphocyte epitopes. J Immunol. Jun. 1, 2002;168(11):5499-506.
Lloyd, Disulphide reduction in lysosomes. The role of cysteine. Biochem J. Jul. 1, 1986;237(1):271-2.
Lönnberg, Solid-phase synthesis of oligonucleotide conjugates useful for delivery and targeting of potential nucleic acid therapeutics. Bioconjug Chem. Jun. 2009;20(6):1065-94.
Low et al., Folate receptor-targeted drugs for cancer and inflammatory diseases. Adv Drug Deliv Rev. 2004;56(8):1055-8.
Ludewig et al., Induction of optimal anti-viral neutralizing B cell responses by dendritic cells requires transport and release of virus particles in secondary lymphoid organs. Eur J Immunol. 2000;30(1):185-96.
Malyala et al., Enhancing the therapeutic efficacy of CpG oligonucleotides using biodegradable microparticles. Adv Drug Deliv Rev. Mar. 28, 2009;61(3):218-25. Epub Jan. 11, 2009.
Malyala et al., The potency of the adjuvant, CpG oligos, is enhanced by encapsulation in PLG microparticles. J Pharm Sci. Mar. 2008;97(3):1155-64.
Manolova et al., Nanoparticles target distinct dendritic cell populations according to their size. Eur J Immunol. 2008;38:1404-13.
Martin et al., A vector-based minigene vaccine approach results in strong induction of T-cell responses specific of hepatitis C virus. Vaccine. May 12, 2008;26(20):2471-81. Epub Apr. 1, 2008.
Martinez-Pomares et al., Antigen presentation the macrophage way. Cell. Nov. 16, 2007;131(4):641-3.
Mathiowitz et al., Novel microcapsules for delivery systems. Reactive Polymers. 1987;6:275-83.
Mathiowitz et al., Polyanhydride Microspheres as Drug Carriers I. Hot-Melt Microencapsulation. J Control Release. 1987;5:13-22.
Mathiowitz et al., Polyanhydride Microspheres as Drug Carriers. II . . . Microencapsulation by Solvent Removal. J Appl Polymer Sci. 1988;35:755-74.
Mattheakis et al., Optical coding of mammalian cells using semiconductor quantum dots. Anal Biochem. 2004;327(2):200-8.
Maye et al., Comparison of the phagocytosis of two types of cyclosporin (SDZ OXL 400 and SDZ IMM 125) by alveolar macrophages from hamsters. Cell Biol Toxicol. Dec. 1998;14(6):411-8.
McSorley et al., Bacterial flagellin is an effective adjuvant for CD4+ T cells in vivo. J Immunol. Oct. 1, 2002;169(7):3914-9.
Meister et al., Mechanisms of gene silencing by double-stranded RNA. Nature. 2004;431(7006):343-9.
Mempel et al., T-cell priming by dendritic cells in lymph nodes occurs in three distinct phases. Nature. 2004;427(6970):154-9.
Metelitsa et al., Antidisialoganglioside/granulocyte macrophage-colonystimulating factor fusion protein facilitates neutrophil antibody-dependent cellular cytotoxicity and depends on FcγRII (CD32) and Mac-1 (CD11b/CD18) for enhanced effector cell adhesion and azurophil granule exocytosis. Blood. 2002;99(11):4166-73.
Michiels et al., Patent exemption for clinical trials: current status of the Bolar-type provisions in Europe. Life Sciences Intellectual Property Review 2008. Lavoix. www.worldipreview.com. 2008:68-70.

(56) References Cited

OTHER PUBLICATIONS

Miyara et al., Therapeutic approaches to allergy and autoimmunity based on FoxP3+ regulatory T-cell activation and expansion. J Allergy Clin Immunol. Apr. 2009;123(4):749-55.
Moghimi et al., Long-circulating and target-specific nanoparticles: theory to practice. Pharmacol Rev. 2001;53(2):283-318.
Moghimi et al., Nanomedicine: current status and future prospects. FASEB J. Mar. 2005;19(3):311-30.
Mulligan, The basic science of gene therapy. Science. 1993;260(5110):926-32.
Murray et al., Synthesis and characterization of monodisperse nanocrystals and close-packed nanocrystal assemblies. Ann Rev Mat Sci. 2000;30:545-610.
Nakase et al., Biodegradable microspheres targeting mucosal immune-regulating cells: new approach for treatment of inflammatory bowel disease. J Gastroenterol. Mar. 2003;38 Suppl 15:59-62.
Nielsen et al., Therapeutic efficacy of anti-ErbB2 immunoliposomes targeted by a phage antibody selected for cellular endocytosis. Biochim Biophys Acta. Aug. 19, 2002;1591(1-3):109-118.
Nikou et al., A HER-2/neu peptide admixed with PLA microspheres induces a Th1-biased immune response in mice. Biochim Biophys Acta. Sep. 15, 2005;1725(2):182-9.
Notter et al., Targeting of a B7-1 (CD80) immunoglobulin G fusion protein to acute myeloid leukemia blasts increases their costimulatory activity for autologous remission T cells. Blood. 2001;97(10):3138-45.
Ochsenbein et al., Control of early viral and bacterial distribution and disease by natural antibodies. Science. 1999;286(5447):2156-9.
Ochsenbein et al., Protective T cell-independent antiviral antibody responses are dependent on complement. J Exp Med. 1999;190(8):1165-74.
Oh et al., CD4+CD25+ regulatory T cells in autoimmune arthritis. Immunol Rev. Jan. 2010;233(1):97-111.
Okada et al., Antigen-engaged B cells undergo chemotaxis toward the T zone and form motile conjugates with helper T cells. PLoS Biol. 2005;3(6):e150. 1047-61.
Olivier et al., Synthesis of pegylated immunonanoparticles. Pharm Res. Aug. 2002;19(8):1137-43.
Ong et al., Redox-triggered contents release from liposomes. J Am Chem Soc. Nov. 5, 2008;130(44):14739-44. Epub Oct. 8, 2008.
O'Sullivan et al., Truncation analysis of several DR binding epitopes. J Immunol. Feb. 15, 1991;146(4):1240-6.
Paoletti et al. eds., Vaccines: from Concept to Clinic. A Guide to the Development and Clinical Testing of Vaccines for Human Use. 1999 CRC Press. 210 pages.
Pape et al., The humoral immune response is initiated in lymph nodes by B cells that acquire soluble antigen directly in the follicles. Immunity. 2007;26(4):491-502.
Pasqualini et al., Aminopeptidase N is a receptor for tumor-homing peptides and a target for inhibiting angiogenesis. Cancer Res. 2000;60(3):722-7.
Patri et al., Synthesis and in Vitro Testing of J591 Antibody—Dendrimer Conjugates for Targeted Prostate Cancer Therapy. Bioconj Chem. 2004;15:1174-81.
Pellegrino et al., On the development of colloidal nanoparticles towards multifunctional structures and their possible use for biological applications. Small. 2005;1(1):48-63
Phillips et al., Enhanced antibody response to liposome-associated protein antigens: preferential stimulation of IgG2a/b production. Vaccine. 1992;10(3):151-8.
Pimentel et al., Peptide nanoparticles as novel immunogens: design and analysis of a prototypic severe acute respiratory syndrome vaccine. Chem Biol Drug Des. Jan. 2009;73(1):53-61.
Pitaksuteepong, Nanoparticles: A vaccine adjuvant for subcutaneous administration. Naresuan University J. 2005;13(2):53-62.
Popielarski et al., A nanoparticle-based model delivery system to guide the rational design of gene delivery to the liver. 2. In vitro and in vivo uptake results. Bioconjug Chem. Sep.-Oct. 2005;16(5):1071-80.
Purcell et al., Dissecting the role of peptides in the immune response: theory, practice and the application to vaccine design. J Pept Sci. May 2003;9(5):255-81.
Purcell et al., More than one reason to rethink the use of peptides in vaccine design. Nat Rev Drug Discov. May 2007;6(5):404-14.
Qi et al., Extrafollicular activation of lymph node B cells by antigen-bearing dendritic cells. Science. 2006;312(5780):1672-6.
Qiu et al., PLA-coated gold nanoparticles for the labeling of PLA biocarriers. Chem Mater. 2004;16:850-6.
Quintanar-Guerrero et al., Preparation Techniques and Mechanisms of Formation of Biodegradable Nanoparticles from Preformed Polymers. Drug Dev Industrial Pharmacy. 1998;24(12):1113-28.
Raman et al., Peptide Based Nanoparticles as a Platform for Vaccine Design. http://www.nsti.org/Nanotech2005/showabstract.html?absno=637. 2005. Abstract Only.
Reddy et al., Exploiting lymphatic transport and complement activation in nanoparticle vaccines. Nat Biotech. 2007;25(10):1159-64.
Reif et al., Balanced responsiveness to chemoattractants from adjacent zones determines B-cell position. Nature. 2002;416(6876):94-9.
Reis et al., Nanoencapsulation I. Methods for preparation of drug-loaded polymeric nanoparticles. Nanomedicine. 2006;2:8-21.
Robbins et al., Stable expression of shRNAs in human CD34+ progenitor cells can avoid induction of interferon responses to siRNAs in vitro. Nature Biotechnology. 2006;24(5):566-71.
Roman et al., Immunostimulatory DNA sequences function as T helper-1-promoting adjuvants. Nat Med. Aug. 1997;3(8):849-54.
Rossbacher et al, The B cell receptor itself can activate complement to provide the complement receptor 1/2 ligand required to enhance B cell immune responses in vivo. J Exp Med. 2003;198(4):591-602.
Salmeron et al., Encapsulation Study of 6-Methylprednisolone in Lipid Microspheres. Drug Develop Indust Pharm. 1997;23(2):133-6.
Samuel et al, Polymeric nanoparticles for targeted delivery of therapeutic vaccines to dendritic cells. Proc Intl Conf on MEMS, NANO and Smart Sys. Jul. 2003;20-23:242-6.
Scardino et al., A polyepitope DNA vaccine targeted to Her-2/ErbB-2 elicits a broad range of human and murine CTL effectors to protect against tumor challenge. Cancer Res. Jul. 15, 2007;67(14):7028-36.
Schultz et al., Single-target molecule detection with nonbleaching multicolor optical immunolabels. Proc Natl Acad Sci USA. 2000;97(3):996-1001.
Schultz, Plasmon resonant particles for biological detection. Curr Op Biotechnol. 2003;14:13-22.
Senger et al., Identification of B-cell epitopes on virus-like particles of cutaneous alpha-human papillomaviruses. J Virol. Dec. 2009;83(24):12692-701. Epub Sep. 30, 2009.
Shahiwala et al., Nanocarriers for systemic and mucosal vaccine delivery. Recent Pat Drug Deliv Formul. 2007;1(1):1-9.
Sharma et al., Pharmaceutical aspects of intranasal delivery of vaccines using particulate systems. J Pharm Sci. Mar. 2009;98(3):812-43.
Shen et al., Enhanced and prolonged cross-presentation following endosomal escape of exogenous antigens encapsulated in biodegradable nanoparticles. Immunol. 2006;117:78-88.
Shestopalov et al., Multi-step synthesis of nanoparticles performed on millisecond time scale in a microfluidic droplet-based system. Lab Chip. 2004;4(4):316-21.
Shiow et al., CD69 acts downstream of interferon-alpha/beta to inhibit S1P1 and lymphocyte egress from lymphoid organs. Nature. Mar. 23, 2006;440(7083):540-4. Epub Mar. 8, 2006.
Singh et al., Anionic microparticles are a potent delivery system for recombinant antigens from Neisseria meningitidis serotype B. J Pharm Sci. Feb. 2004;93(2):273-82.
Singh et al., Cationic microparticles are an effective delivery system for immune stimulatory cpG DNA. Pharm Res. Oct. 2001;18(10):1476-9.
Singh et al., Nanoparticles and microparticles as vaccine-delivery systems. Expert Rev Vaccines. Oct. 2007;6(5):797-808.
Sondel et al., Preclinical and clinical development of immunocytokines. Curr Opin Investig Drugs. 2003;4(6):696-700.

(56) References Cited

OTHER PUBLICATIONS

Sonehara et al., Hexamer palindromic oligonucleotides with 5'-CG-3' motif(s) induce production of interferon. J Interferon Cytokine Res. Oct. 1996;16(10):799-803.

Srinivasan et al., Prediction of class I T-cell epitopes: evidence of presence of immunological hot spots inside antigens. Bioinformatics. Aug. 4, 2004;20 Suppl 1:i297-302.

Stivaktakis et al., Immune responses in mice of beta-galactosidase adsorbed or encapsulated in poly(lactic acid) and poly(lactic-co-glycolic acid) microspheres. J Biomed Mater Res A. Jun. 1, 2005;73(3):332-8.

Stivaktakis et al., PLA and PLGA microspheres of beta-galactosidase: Effect of formulation factors on protein antigenicity and immunogenicity. J Biomed Mater Res A. Jul. 1, 2004;70(1):139-48.

Storm et al., Surface Modification of Nanoparticles to Oppose Uptake by the Mononuclear Phagocyte System. Adv Drug Deliv Rev. 1995;17:31-48.

Suri et al., Nanotechnology-based drug delivery systems. J Occup Med Toxicol. Dec. 1, 2007;2:16.

Tabata et al., Macrophage activation through phagocytosis of poly (L-lactic acid) microspheres containing an immunomodulatory agent. 1989;7(2):79-86. Abstract only.

Tabata et al., Protein precoating of polylactide microspheres containing a lipophilic immunopotentiator for enhancement of macrophage phagocytosis and activation. Pharm Res. Apr. 1989;6(4):296-301.

Tang et al., Adenovirus hexon T-cell epitope is recognized by most adults and is restricted by HLA DP4, the most common class II allele. Gene Ther. Sep. 2004;11(18):1408-15.

Tang et al., In Vitro Gene Delivery by Degraded Polyamidoamine Dendrimers. Bioconjugate Chem. 1996;7:703-14.

Tarlinton et al., Antigen to the node: B cells go native. Immunity. Apr. 2007;26(4):388-90.

Taylor et al., Macrophage receptors and immune recognition. Annu Rev Immunol. 2005;23:901-44.

Timmerman, Carrier protein conjugate vaccines: the "missing link" to improved antibody and CTL responses? Hum Vaccin. Mar. 2009;5(3):181-3. Epub Mar. 24, 2009.

Tissot et al., Versatile virus-like particle carrier for epitope based vaccines. PLoS One. Mar. 23, 2010;5(3):e9809.

Tomai et al., Resiquimod and other immune response modifiers as vaccine adjuvants. Expert Rev Vaccines. Oct. 2007;6(5):835-47.

Tong et al., Ring-opening polymerization-mediated controlled formulation of polylactide-drug nanoparticles. J Am Chem Soc. Apr. 8, 2009;131(13):4744-54. E-pub Mar. 12, 2009.

Trindade et al., Nanocrystalline Semiconductors: Synthesis, Properties, and Perspectives. Chem Mat. 2001;13(11):3843-58.

Uhrich et al., Polymeric Systems for Controlled Drug Release. Chem Rev. 1999;99(11):3181-98.

Unkeless et al., Structure and function of human and murine receptors for IgG. Annu Rev Immunol. 1998;6:251-81.

Uwatoku et al., Application of Nanoparticle Technology for the Prevention of Restenosis After Balloon Injury in Rats. Circ Res. 2003;92(7):e62-9.

Van Broekhoven et al., Targeting dendritic cells with antigen-containing liposomes: a highly effective procedure for induction of antitumor immunity and for tumor immunotherapy. Cancer Res.Jun. 15, 2004;64(12):4357-65.

Vascotto et al., Antigen presentation by B lymphocytes: how receptor signaling directs membrane trafficking. Curr Opin Immunol. 2007;19(1):93-8.

Vauthier et al., Design aspects of poly(alkylcyanoacrylate) nanoparticles for drug delivery. J Drug Target. Dec. 2007;15(10):641-63.

Vila et al., Regulatory T cells and autoimmunity. Curr Opin Hematol. Jul. 2009;16(4):274-9.

Vita et al., The immune epitope database 2.0. Nucleic Acids Res. Jan. 2010;38(Database issue):D854-62. Epub Nov. 11, 2009.

Vollmer et al., Characterization of three CpG oligodeoxynucleotide classes with distinct immunostimulatory activities. Eur J Immunol. Jan. 2004;34(1):251-62.

Von Andrian et al., Homing and cellular traffic in lymph nodes. Nat Rev Immunol. 2003;3(11):867-78.

Weber et al., T cell epitope: friend or foe? Immunogenicity of biologics in context. Adv Drug Deliv Rev. Sep. 30, 2009;61(11):965-76. Epub Jul. 18, 2009.

Wessels et al., Studies of group B streptococcal infection in mice deficient in complement component C3 or C4 demonstrate an essential role for complement in both innate and acquired immunity. Proc Natl Acad Sci USA. 1995;92(25):11490-4.

Whelan et al., Efficient recovery of infectious vesicular stomatitis virus entirely from cDNA clones. Proc Natl Acad Sci USA. 1995;92(18):8388-92.

Wu et al., A novel chitosan CpG nanoparticle regulates cellular and humoral immunity of mice.Biomed Environ Sci. Apr. 2006;19(2):87-95.

Wu et al., Resiquimod: a new immune response modifier with potential as a vaccine adjuvant for Th1 immune responses. Antiviral Res. Nov. 2004;64(2):79-83.

Yang et al., Tumor necrosis factor alpha blocking peptide loaded PEG-PLGA nanoparticles: preparation and in vitro evaluation. Int J Pharm. Feb. 22, 2007;331(1):123-32.

Yang, Imaging of vascular gene therapy. Radiology. 2003;228:36-49.

Yoo et al., in vitro and In vivo anti-tumor activities of nanoparticles based on doxorubicin—PLGA conjugates. J Control Release. 2000;68(3):419-31.

Yu et al., Potent CpG oligonucleotides containing phosphodiester linkages: in vitro and in vivo immunostimulatory properties. Biochem Biophys Res Commun. Sep. 13, 2002;297(1):83-90.

Yuan et al., Intranasal immunization with chitosan/pCETP nanoparticles inhibits atherosclerosis in a rabbit model of atherosclerosis. Vaccine. Jul. 4, 2008;26(29-30):3727-34. Epub May 16, 2008.

Zauner et al., Polylysine-based transfection systems utilizing receptor-mediated delivery. Adv Drug Del Rev. 1998;30:97-113.

Zhang et al., A comparative study of the antigen-specific immune response induced by co-delivery of CpG ODN and antigen using fusion molecules or biodegradable microparticles. J Pharm Sci. Dec. 2007;96(12):3283-92.

Zhang et al., Nanoparticles of poly(lactide)/vitamin E TPGS copolymer for cancer chemotherapy: synthesis, formulation, characterization and in vitro drug release. Biomaterials. Jan. 2006;27(2):262-70.

Zhang-Hoover et al., Tolerogenic APC generate CD8+ T regulatory cells that modulate pulmonary interstitial fibrosis. J Immunol. Jan. 1, 2004;172(1):178-85.

Zheng et al., Highly fluorescent, water-soluble, size-tunable gold quantum dots. Phys Rev Lett. 2004;93(7):077402.1-4.

Zheng et al., How antigen quantity and quality determine T-cell decisions in lymphoid tissue. Mol Cell Biol. Jun. 2008;28(12):4040-51. Epub Apr. 21, 2008.

Zhou et al., Investigation on a novel core-coated microspheres protein delivery system. J Control Release. Jul. 10, 2001;75(1-2):27-36.

Zhu et al., T cell epitope mapping of ragweed pollen allergen Ambrosia artemisiifolia (Amb a 5) and Ambrosia trifida (Amb t 5) and the role of free sulfhydryl groups in T cell recognition. J Immunol. Nov. 15, 1995;155(10):5064-73.

Zwiorek et al., Delivery by cationic gelatin nanoparticles strongly increases the immunostimulatory effects of CpG oligonucleotides. Pharm Res. Mar. 2008;25(3):551-62. Epub Oct. 3, 2007.

U.S. Appl. No. 13/560,943, filed Jul. 27, 2012, Gao et al.

Extended European Search Report for Application No. EP 12819411.5 dated Mar. 18, 2015.

Stano et al., PPS nanoparticles as versatile delivery system to induce systemic and broad mucosal immunity after intranasal administration. Vaccine. Jan. 17, 2011;29(4):804-12. doi: 10.1016/j.vaccine. 2010.11.010. Epub Nov. 19, 2010.

EP 12819411.5, Mar. 18, 2015, Extended European Search Report.

U.S. Appl. No. 14/658,040, filed Mar. 13, 2015, Zepp et al.

U.S. Appl. No. 14/717,451, filed May 20, 2015, Ilyinskii et al.

(56) References Cited

OTHER PUBLICATIONS

U.S. Appl. No. 15/050,397, filed Feb. 22, 2016, Fraser et al.
U.S. Appl. No. 14/810,418, filed Jul. 27, 2015, Fraser et al.
U.S. Appl. No. 14/802,260, filed Jul. 17, 2015, Altreuter et al.
U.S. Appl. No. 14/810,427, filed Jul. 27, 2015, Fraser et al.
U.S. Appl. No. 15/061,096, filed Mar. 4, 2016, Fraser et al.
U.S. Appl. No. 14/810,442, filed Jul. 27, 2015, Fraser et al.
U.S. Appl. No. 14/10,450, filed Jul. 27, 2015, Fraser et al.
U.S. Appl. No. 14/810,457, filed Jul. 27, 2015, Kishimoto et al.
U.S. Appl. No. 15/061,204, filed Mar. 4, 2016, Kishimoto et al.
U.S. Appl. No. 14/810,466, filed Jul. 27, 2015, Kishimoto et al.
U.S. Appl. No. 14/810,472, filed Jul. 27, 2015, Fraser et al.
U.S. Appl. No. 14/810,476, filed Jul. 27, 2015, Maldonado.
U.S. Appl. No. 14/269,047, filed May 2, 2015, Maldonado et al.
U.S. Appl. No. 14/269,056, filed May 2, 2014, Maldonato et al.
U.S. Appl. No. 14/742,583, filed Jun. 17, 2015, Kishimoto.
U.S. Appl. No. 14/751,106, filed Jun. 25, 2015, Kishimoto et al.
U.S. Appl. No. 14/846,949, filed Sep. 7, 2015, Kishimoto.
U.S. Appl. No. 14/846,952, filed Sep. 7, 2015, Kishimoto.
U.S. Appl. No. 14/846,958, filed Sep. 7, 2015, Kishimoto.
U.S. Appl. No. 14/846,964, filed Sep. 7, 2015, Kishimoto.
U.S. Appl. No. 14/934,132, filed Nov. 5, 2015, Griset et al.
U.S. Appl. No. 14/934,135, filed Nov. 5, 2015, Griset et al.
U.S. Appl. No. 14/846,967, filed Sep. 7, 2015, Kishimoto.
U.S. Appl. No. 15/456,520, filed Mar. 11, 2017, Johnston.
Robbins et al., Fabricated Nanoparticles with Cross Validation Using a Humanized Mouse Model. Nanomed Nanotech Biol Med. 2015. Accepted manuscript. doi: 10.1016/j.nano.2014.11.010. 36 pages.
Thomas et al., Engineering complement activation on polypropylene sulfide vaccine nanoparticles. Biomaterials. Mar. 2011;32(8):2194-203. doi: 10.1016/j.biomaterials.2010.11.037.
Wong et al., Cutting edge: antigen-independent CD8 T cell proliferation. J Immunol. May 15, 2001;166(10):5864-8.
[No Author Listed] Drug Delivery System. May 2007;22(3):289.
Akagi et al., Development of vaccine adjuvants using polymeric nanoparticles and their potential applications for anti-HIV vaccine. Yakugaku Zasshi. 2007;127(2):307-17.
Anderson et al., Cytotoxic T cells. J Invest Dermatol. 2006;126:32-41. DOI:10.1038/sj.jid5700001.
Ma et al., Enhanced presentation of MHC Class Ia, Ib and Class II—restricted peptides encapsulated in biodegradable nanoparticles: a promising strategy for tumor immunotherapy. J Transl Med. Mar. 31, 2011;9(34):1-10. https://doi.org/10.1186/1479-5876-9-34.
U.S. Appl. No. 12/788,260, filed May 26, 2010, Zepp et al.
U.S. Appl. No. 13/948,129, filed Jul. 22, 2013, Zepp et al.
U.S. Appl. No. 14/273,099, filed May 8, 2014, Zepp et al.
U.S. Appl. No. 12/788,261, filed May 26, 2010, Lipford et al.
U.S. Appl. No. 14/138,601, filed Dec. 23, 2013, Zepp et al.
U.S. Appl. No. 12/862,076, filed Aug. 24, 2010, Fraser et al.
U.S. Appl. No. 13/116,453, filed May 26, 2011, Bratzler et al.
U.S. Appl. No. 12/764,569, filed Apr. 21, 2010, Lipford et al.
U.S. Appl. No. 13/116,488, filed May 26, 2011, Bratzler et al.
U.S. Appl. No. 13/116,542, filed May 26, 2011, Ilyinskii et al.
U.S. Appl. No. 13/116,556, filed May 26, 2011, Bratzler et al.
U.S. Appl. No. 13/289,211, filed Nov. 4, 2011, Zepp et al.
U.S. Appl. No. 13/428,340, filed Mar. 23, 2012, Altreuter et al.
U.S. Appl. No. 13/458,021, filed Apr. 27, 2012, Fraser et al.
U.S. Appl. No. 13/458,980, filed Apr. 27, 2012, Altreuter et al.
U.S. Appl. No. 13/458,067, filed Apr. 27, 2012, Fraser et al.
U.S. Appl. No. 13/457,994, filed Apr. 27, 2012, Fraser et al.
U.S. Appl. No. 13/457,999, filed Apr. 27, 2012, Fraser et al.
U.S. Appl. No. 13/457,977, filed Apr. 27, 2012, Kishimoto et al.
U.S. Appl. No. 13/457,936, filed Apr. 27, 2012, Kishimoto et al.
U.S. Appl. No. 13/458,220, filed Apr. 27, 2012, Fraser et al.
U.S. Appl. No. 14/161,660, filed Jan. 22, 2014, Maldonado.
U.S. Appl. No. 14/269,047, filed May 2, 2014, Maldonado et al.
U.S. Appl. No. 14/296,204, filed Jun. 4, 2014, Maldonado et al.
U.S. Appl. No. 14/269,048, filed May 2, 2014, Maldonado.
U.S. Appl. No. 14/269,054, filed May 2, 2014, Maldonado.
U.S. Appl. No. 14/269,058, filed May 2, 2014, Kishimoto.
U.S. Appl. No. 14/269,056, filed May 2, 2014, Maldonado et al.
U.S. Appl. No. 14/269,042, filed May 2, 2014, Kishimoto et al.
PCT/US2012/048670, Feb. 27, 2013, International Search Report and Written Opinion.
PCT/US2012/048670, Feb. 13, 2014, International Preliminary Report on Patentability.

\* cited by examiner

SEQUENCE LISTING

<160> NUMBER OF SEQ ID NOS: 2

<210> SEQ ID NO 1
<211> LENGTH: 8
<212> TYPE: PRT
<213> ORGANISM: Artificial Sequence
<220> FEATURE:
<223> OTHER INFORMATION: Synthetic Peptide

<400> SEQUENCE: 1

```
Ser Ile Ile Asn Phe Glu Lys Leu
1               5

<210> SEQ ID NO 2
<211> LENGTH: 20
<212> TYPE: PRT
<213> ORGANISM: Artificial Sequence
<220> FEATURE:
<223> OTHER INFORMATION: Synthetic Peptide

<400> SEQUENCE: 2

Thr Cys Cys Ala Thr Gly Ala Cys Gly Thr Thr Cys Cys Thr Gly Ala
1               5                   10                  15

Cys Gly Thr Thr
            20
```

METHODS FOR ADMINISTERING SYNTHETIC NANOCARRIERS THAT GENERATE HUMORAL AND CYTOTOXIC T LYMPHOCYTE RESPONSES

RELATED APPLICATIONS

This application claims the benefit under 35 U.S.C. § 119 of U.S. provisional application 61/513,496, 61/513,526 and 61/513,527, each filed Jul. 29, 2011, the entire contents of each of which are incorporated herein by reference.

FIELD OF THE INVENTION

This invention relates to methods for generating humoral and cytotoxic T lymphocyte (CTL) immune responses in a subject and related compositions. Generally, the humoral and CTL immune responses are generated with synthetic nanocarrier compositions that comprise a protein that comprises at least one humoral epitope and at least one MHC Class I-restricted epitope.

BACKGROUND OF THE INVENTION

Classically, vaccines have promoted a single arm of the immune system, for example, the generation of a humoral immune response consisting of antibodies to an antigen or, alternatively, activation of a CTL response to an antigen. Additionally, conventional vaccines generally do not target the sites of action of cells of interest, such as APCs, in an optimal manner. Methods and compositions for effectively activating both of these arms of the immune system optimally to effectively generate immune responses and/or reduce off-target effects and toxicity are needed.

SUMMARY OF THE INVENTION

Provided herein are methods, and related compositions, for generating humoral and CTL immune responses in a subject. In one aspect, a method comprising identifying a subject in need of a humoral and CTL immune response to a first protein, and administering to the subject a composition comprising a population of synthetic nanocarriers coupled to the first protein, wherein the first protein comprises at least one humoral epitope and at least one MHC Class I-restricted epitope that are not the same epitope, wherein the population of synthetic nanocarriers does not comprise a saponin-cholesterol adjuvant, and wherein the mean of a particle size distribution obtained using dynamic light scattering of the population of synthetic nanocarriers is a maximum dimension of from 20 nm to 250 nm is provided. In another embodiment, the mean of a DLS distribution is determined by any of the examples of such a method provided herein. Such examples are described in more detail below. In one embodiment, the composition is administered in an amount effective to generate a humoral and CTL immune response to the first protein.

In another aspect, a method comprising administering to the subject a composition comprising a population of synthetic nanocarriers coupled to a first protein; wherein the first protein comprises at least one humoral epitope and at least one MHC Class I-restricted epitope that are not the same epitope, wherein the population of synthetic nanocarriers does not comprise a saponin-cholesterol adjuvant, wherein the mean of a particle size distribution obtained using dynamic light scattering of the population of synthetic nanocarriers is a maximum dimension of from 20 nm to 250 nm, and wherein the composition is administered according to a vaccination regimen is provided.

In another aspect, a method comprising administering to the subject a composition comprising a population of synthetic nanocarriers coupled to a first protein; wherein the first protein comprises at least one humoral epitope and at least one MHC Class I-restricted epitope that are not the same epitope, wherein the population of synthetic nanocarriers does not comprise a saponin-cholesterol adjuvant, wherein the mean of a particle size distribution obtained using dynamic light scattering of the population of synthetic nanocarriers is a maximum dimension of from 20 nm to 250 nm, and wherein the composition is administered according to a protocol that was previously shown to result in a humoral and CTL immune response specific to the first protein in one or more test subjects is provided.

In one embodiment, the methods provided herein further comprise identifying a subject in need of a humoral and cytotoxic T lymphocyte (CTL) immune response to the first protein. In another embodiment, the composition is administered according to a vaccination regimen. In yet another embodiment, the composition is administered according to a protocol that was previously shown to result in a humoral and CTL immune response specific to the first protein in one or more test subjects In another embodiment, the composition further comprises one or more adjuvants. In another embodiment, the method further comprises administering one or more adjuvants. In a further embodiment, the one or more adjuvants comprise stimulators or agonists of pattern recognition receptors, mineral salts, alum, alum combined with monphosphoryl lipid A of Enterobacteria (MPL), MPL® (AS04), AS15, saponins, QS-21, Quil-A, ISCOMs, ISCOMA-TRIX™, MF59™, Montanide® ISA 51, Montanide® ISA 720, AS02, liposomes and liposomal formulations, AS01, synthesized or specifically prepared microparticles and microcarriers, bacteria-derived outer membrane vesicles of *N. gonorrheae* or *Chlamydia trachomatis*, chitosan particles, depot-forming agents, Pluronic® block co-polymers, specifically modified or prepared peptides, muramyl dipeptide, aminoalkyl glucosaminide 4-phosphates, RC529, bacterial toxoids, toxin fragments, agonists of Toll-Like Receptors 2, 3, 4, 5, 7, 8, 9 and/or combinations thereof; adenine derivatives; immunostimulatory DNA; immunostimulatory RNA; imidazoquinoline amines, imidazopyridine amines, 6,7-fused cycloalkylimidazopyridine amines, 1,2-bridged imidazoquinoline amines; imiquimod; resiquimod; agonist for DC surface molecule CD40; type I interferons; poly I:C; bacterial lipopolysacccharide (LPS); VSV-G; HMGB-1; flagellin or portions or derivatives thereof; immunostimulatory DNA molecules comprising CpGs; proinflammatory stimuli released from necrotic cells; urate crystals; activated components of the complement cascade; activated components of immune complexes; complement receptor agonists; cytokines; or cytokine receptor agonists. In yet another embodiment, the one or more adjuvants comprise an agonist of Toll-Like Receptor 2, 3, 4, 7, 8 or 9. In still another embodiment, the one or more adjuvants comprise an imidazoquinoline or oxoadenine. In one embodiment, the imidazoquinoline comprises resiquimod or imiquimod.

In another embodiment, the one or more adjuvants are coupled to the synthetic nanocarriers of the population of synthetic nanocarriers.

In still another embodiment, the composition further comprises or the method further comprises administering another population of synthetic nanocarriers, and the one or more adjuvants are coupled to the synthetic nanocarriers of the other population of synthetic nanocarriers.

In a further embodiment, the one or more adjuvants are not coupled to a synthetic nanocarrier.

In another embodiment, the composition further comprises one or more additional antigens or the method further comprises administering one or more additional antigens. In an embodiment, the one or more additional antigens comprise at least one humoral epitope and/or at least one MHC Class I-restricted epitope. In another embodiment, the one or more additional antigens comprise at least one humoral epitope and at least one MHC Class I-restricted epitope that are not the same epitope. In one embodiment, the one or more additional antigens comprise a second protein. In another embodiment, the one or more additional antigens comprise a humoral epitope and/or a MHC Class I-restricted epitope. In still another embodiment, the one or more additional antigens comprise a humoral epitope and a MHC Class I-restricted epitope. In yet another embodiment, the one or more additional antigens comprise at least one humoral epitope and at least one MHC Class I-restricted epitope that are not the same epitope.

In one embodiment, the one or more additional antigens are coupled to the synthetic nanocarriers.

In another embodiment, the composition further comprises or the method further comprises administering another population of synthetic nanocarriers, and the one or more additional antigens are coupled to the synthetic nanocarriers of the other population of synthetic nanocarriers.

In still another embodiment, the one or more additional antigens are not coupled to a synthetic nanocarrier.

In one embodiment, the synthetic nanocarriers and/or other synthetic nanocarriers comprise a polymeric nanoparticle, a metallic nanoparticle, a dendrimer, a buckyball, a nanowire, a virus-like particle or a peptide or protein particle. In another embodiment, the synthetic nanocarriers and/or other synthetic nanocarriers comprise one or more polymers. In yet another embodiment, the one or more polymers comprise a polyester, polyamino acid, polycarbonate, polyacetal, polyketal, polysaccharide, polyethyloxazoline or polyethyleneimine. In still another embodiment, the one or more polymers comprise a polyester. In one embodiment, the polyester comprises a poly(lactic acid), poly(glycolic acid), poly(lactic-co-glycolic acid) or polycaprolactone. In another embodiment, the polyester is coupled to a polyether. In yet another embodiment, the polyether comprises polyethylene glycol.

In one embodiment, the first protein and/or one or more additional antigens are antigens associated with cancer, an infection or infectious disease or a non-autoimmune or degenerative disease. In another embodiment, the first protein and/or one or more additional antigens are antigens associated with human immunodeficiency virus (HIV), malaria, leischmaniasis, a human filovirus infection, a togavirus infection, a alphavirus infection, an arenavirus infection, a bunyavirus infection, a flavivirus infection, a human papillomavirus infection, a human influenza A virus infection, a hepatitis B infection or a hepatitis C infection.

In another embodiment, the subject has or is at risk of having cancer, an infection or infectious disease or a non-autoimmune or degenerative disease. In yet another embodiment, the subject has or is at risk of having HIV, malaria, leischmaniasis, a human filovirus infection, a togavirus infection, a alphavirus infection, an arenavirus infection, a bunyavirus infection, a flavivirus infection, a human papillomavirus infection, a human influenza A virus infection, a hepatitis B infection or a hepatitis C infection.

In still another embodiment, the humoral and CTL immune responses that are generated are clinically effective. In one embodiment, the immune responses are effective to treat or prevent cancer, an infection or infectious disease or a non-autoimmune or degenerative disease in the subject. In another embodiment, the immune responses are effective to treat or prevent HIV, malaria, leischmaniasis, a human filovirus infection, a togavirus infection, a alphavirus infection, an arenavirus infection, a bunyavirus infection, a flavivirus infection, a human papillomavirus infection, a human influenza A virus infection, a hepatitis B infection or a hepatitis C infection in the subject.

In one embodiment, the composition further comprises a pharmaceutically acceptable excipient.

In another embodiment, the composition is sterile.

In another embodiment, the composition is reconstituted from a lyophilized form.

In another aspect, a dosage form comprising any of the compositions provided is provided.

In yet another aspect, a vaccine comprising any of the compositions and dosage forms provided is provided.

In yet a further embodiment, the composition is administered by intravenous, oral, subcutaneous, pulmonary, intranasal, intradermal, transmucosal, intramucosal or intramuscular administration.

In still another aspect, a method comprising administering any of the compositions provided herein to a subject in need thereof is provided. In one embodiment, the subject is a human. In another embodiment, the subject has or is at risk of having cancer. In still another embodiment, the subject has or is at risk of having an infection or infectious disease. In yet another embodiment, the subject has or is at risk of having a non-autoimmune or degenerative disease. In yet a further embodiment, the subject has or is at risk of having HIV. In another embodiment, the subject has or is at risk of having malaria, leischmaniasis, a human filovirus infection, a togavirus infection, a alphavirus infection, an arenavirus infection, a bunyavirus infection, a flavivirus infection, a human papillomavirus infection, a human influenza A virus infection, a hepatitis B infection or a hepatitis C infection.

In one embodiment of any of the methods provided herein, any of the compositions provided can be administered to a subject, such as a human, according to a vaccination regimen.

In another embodiment of any of the method provided herein, any of the compositions provided can be administered to a subject according to a protocol that was previously shown to result in a humoral and CTL immune response specific to the first protein in one or more test subjects is provided In another aspect, any of the methods provided can further comprise assessing the humoral and CTL immune response in the subject. The methods for assessing the humoral and CTL immune response can be any of the methods provided herein.

In yet another aspect, a method comprising preparing any of the compositions provided herein and assessing the generation of a humoral and CTL immune response is provided. In one embodiment, the composition comprises synthetic nanocarriers coupled to a first protein that comprises at least one humoral epitope and at least one MHC Class I-restricted epitope that are not the same epitope. In another embodiment, the population of synthetic nanocarriers coupled to the first protein does not comprise a saponin-cholesterol adjuvant and/or the mean of a particle size distribution obtained using dynamic light scattering of the population of synthetic nanocarriers is a maximum dimension of from 20 nm to 250 nm.

In one aspect, a composition comprising a population of synthetic nanocarriers coupled to a first protein, wherein the first protein comprises at least one humoral epitope and at least one MHC Class I-restricted epitope that are not the same epitope, wherein the population of synthetic nanocarriers does not comprise a saponin-cholesterol adjuvant, and wherein the mean of a particle size distribution obtained using dynamic light scattering of the population of synthetic nanocarriers is a maximum dimension of from 20 nm to 250 nm, for use in therapy or prophylaxis is provided.

In another aspect, a composition comprising a population of synthetic nanocarriers coupled to a first protein, wherein the first protein comprises at least one humoral epitope and at least one MHC Class I-restricted epitope that are not the same epitope, wherein the population of synthetic nanocarriers does not comprise a saponin-cholesterol adjuvant, and wherein the mean of a particle size distribution obtained using dynamic light scattering of the population of synthetic nanocarriers is a maximum dimension of from 20 nm to 250 nm, for use in any of the methods provided herein is provided.

In yet another aspect, a composition comprising a population of synthetic nanocarriers coupled to a first protein, wherein the first protein comprises at least one humoral epitope and at least one MHC Class I-restricted epitope that are not the same epitope, wherein the population of synthetic nanocarriers does not comprise a saponin-cholesterol adjuvant, and wherein the mean of a particle size distribution obtained using dynamic light scattering of the population of synthetic nanocarriers is a maximum dimension of from 20 nm to 250 nm, for use in vaccination is provided.

In still another aspect, a composition comprising a population of synthetic nanocarriers coupled to a first protein, wherein the first protein comprises at least one humoral epitope and at least one MHC Class I-restricted epitope that are not the same epitope, wherein the population of synthetic nanocarriers does not comprise a saponin-cholesterol adjuvant, and wherein the mean of a particle size distribution obtained using dynamic light scattering of the population of synthetic nanocarriers is a maximum dimension of from 20 nm to 250 nm, for use in generating a humoral and CTL immune response to the first protein in a subject is provided. In one embodiment, these immune responses are clinically effective. In another embodiment, these immune responses are each effective in achieving immunity against a disease.

In a further aspect, a composition comprising a population of synthetic nanocarriers coupled to a first protein, wherein the first protein comprises at least one humoral epitope and at least one MHC Class I-restricted epitope that are not the same epitope, wherein the population of synthetic nanocarriers does not comprise a saponin-cholesterol adjuvant, and wherein the mean of a particle size distribution obtained using dynamic light scattering of the population of synthetic nanocarriers is a maximum dimension of from 20 nm to 250 nm, for use in a method of therapy or prophylaxis of cancer, an infection or infectious disease, a non-autoimmune or degenerative disease, HIV, malaria, leishmaniasis, a human filovirus infection, a togavirus infection, a alphavirus infection, an arenavirus infection, a bunyavirus infection, a flavivirus infection, a human papillomavirus infection, a human influenza A virus infection, a hepatitis B infection or a hepatitis C infection I is provided.

In still a further aspect, a composition comprising a population of synthetic nanocarriers coupled to a first protein, wherein the first protein comprises at least one humoral epitope and at least one MHC Class I-restricted epitope that are not the same epitope, wherein the population of synthetic nanocarriers does not comprise a saponin-cholesterol adjuvant, and wherein the mean of a particle size distribution obtained using dynamic light scattering of the population of synthetic nanocarriers is a maximum dimension of from 20 nm to 250 nm, for use in a method of therapy or prophylaxis comprising administration by intravenous, oral, subcutaneous, pulmonary, intranasal, intradermal, transmucosal, intramucosal or intramuscular administration is provided.

In yet a further aspect, a composition comprising a population of synthetic nanocarriers coupled to a first protein, wherein the first protein comprises at least one humoral epitope and at least one MHC Class I-restricted epitope that are not the same epitope, wherein the population of synthetic nanocarriers does not comprise a saponin-cholesterol adjuvant, and wherein the mean of a particle size distribution obtained using dynamic light scattering of the population of synthetic nanocarriers is a maximum dimension of from 20 nm to 250 nm, for the manufacture of a medicament, for example a vaccine, for use in any of the methods provided herein is provided.

In another aspect, a composition for use as defined for any of the compositions or methods provided herein wherein the composition is any of the compositions provided herein is provided.

DETAILED DESCRIPTION OF THE INVENTION

Figure 1:
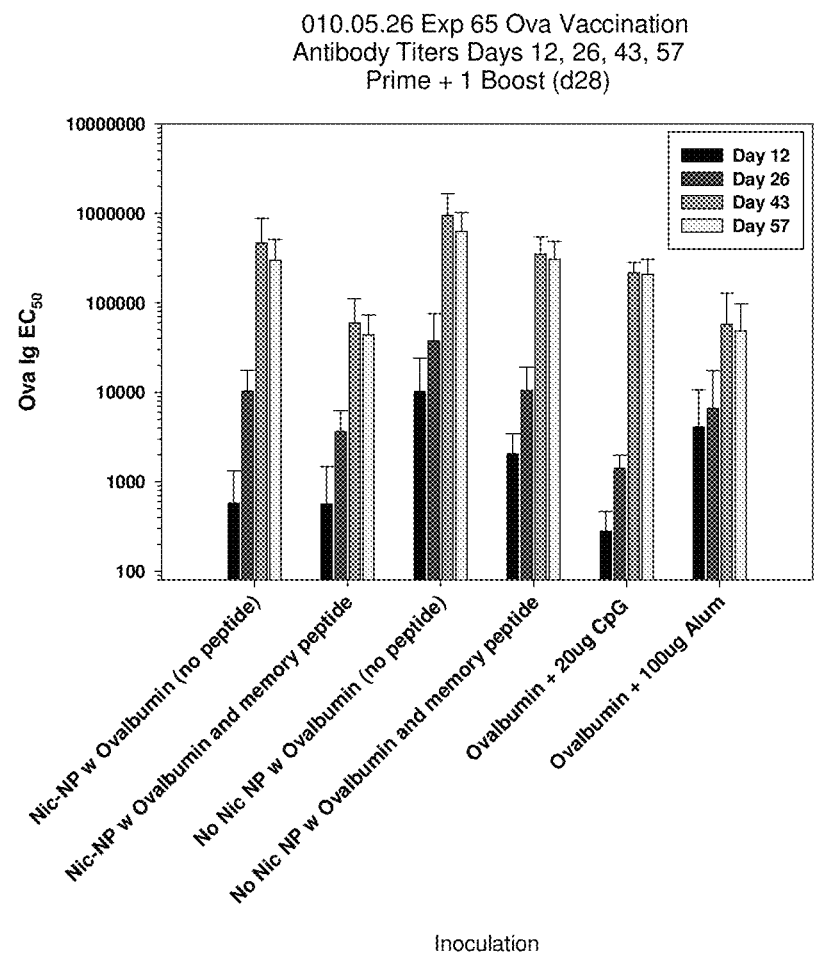
FIG. 1 shows the antibody titers generated at days 12, 26, 43 and 57 following a prime and one boost (on day 28) vaccination regimen.
Figure 2:
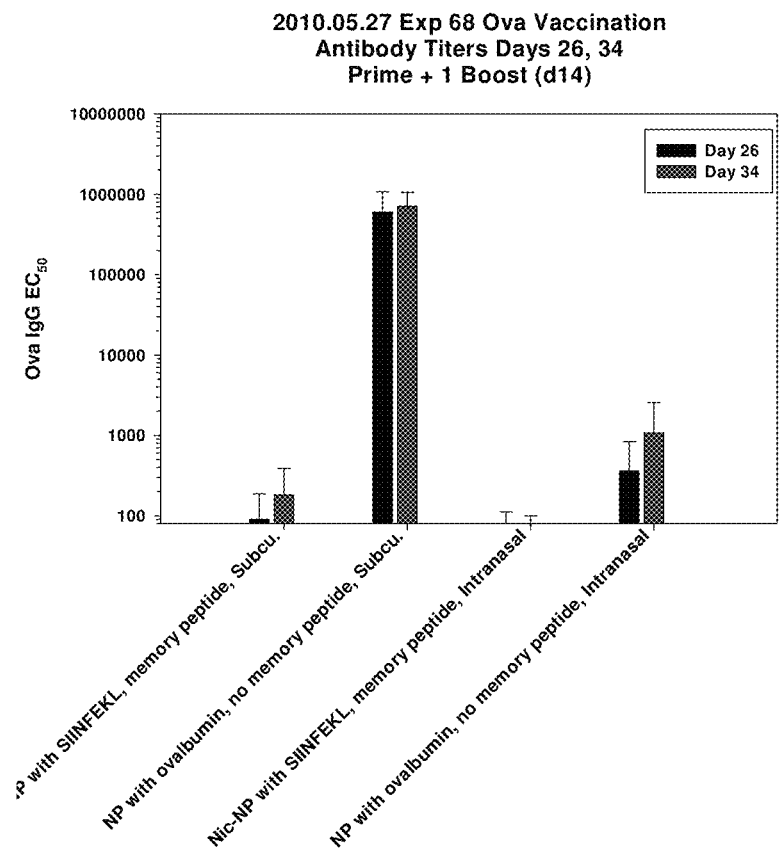
FIG. 2 shows the antibody titers generated at days 26 and 34 following a prime and one boost (on day 14) vaccination regimen.
Figure 3:
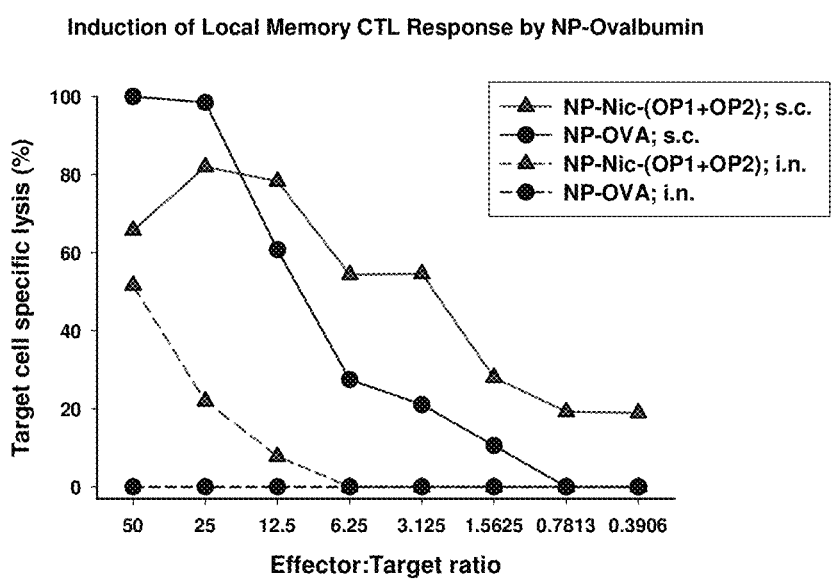
FIG. 3 shows the induction of local memory CTL response by synthetic nanocarriers coupled to ovalbumin (OVA).
Figure 4:
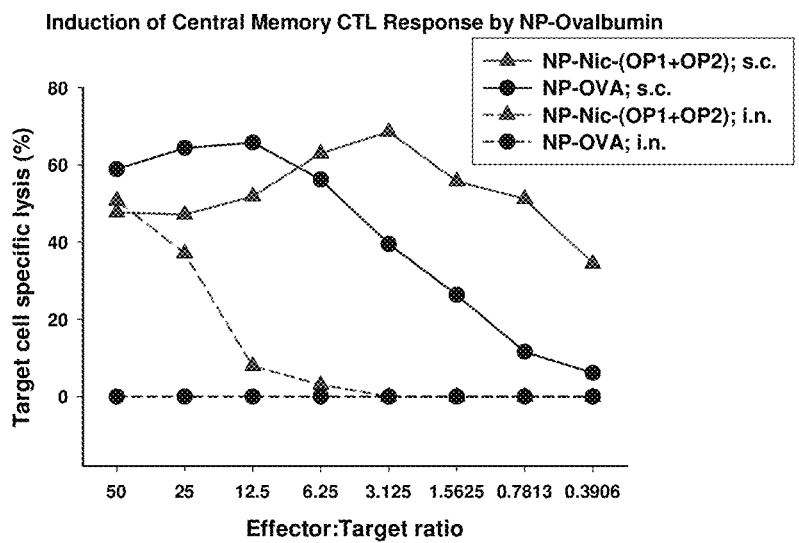
FIG. 4 shows the induction of central CTL response by synthetic nanocarriers coupled to ovalbumin.
Figure 5:
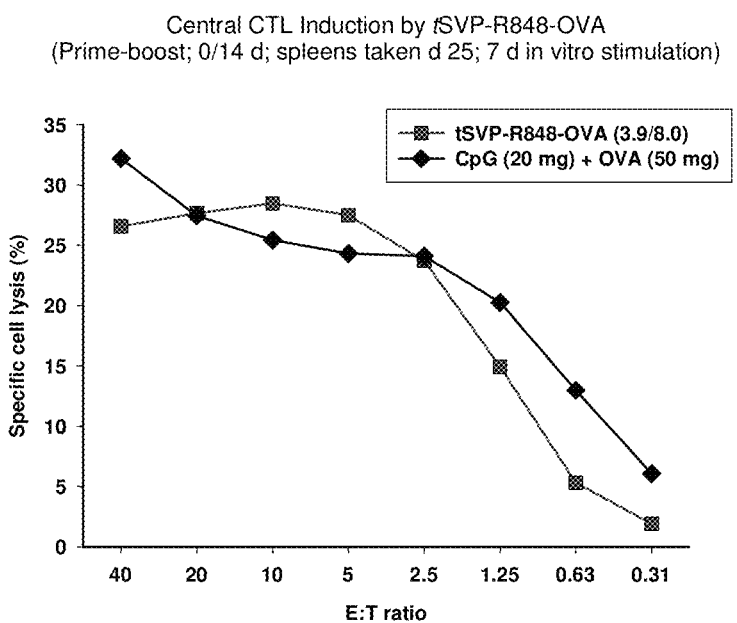
FIG. 5 shows the induction of central CTL induction by synthetic nanocarrier compositions with ovalbumin and adjuvant.
Figure 6:
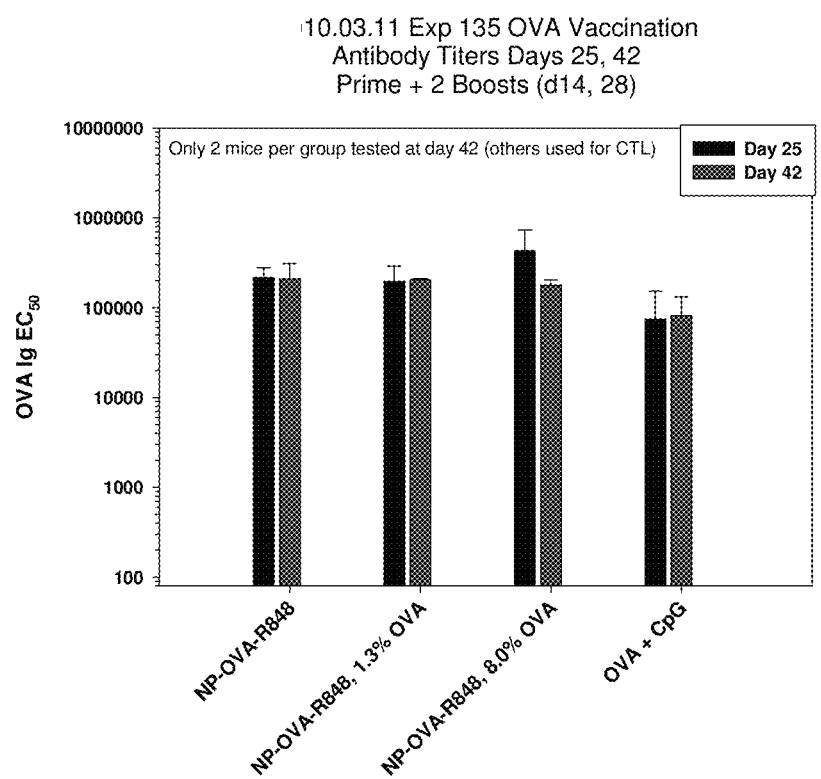
FIG. 6 shows the antibody titers generated at days 25 and 42 following a prime and two boosts (on days 14 and 28) vaccination regimen.
Figure 7:
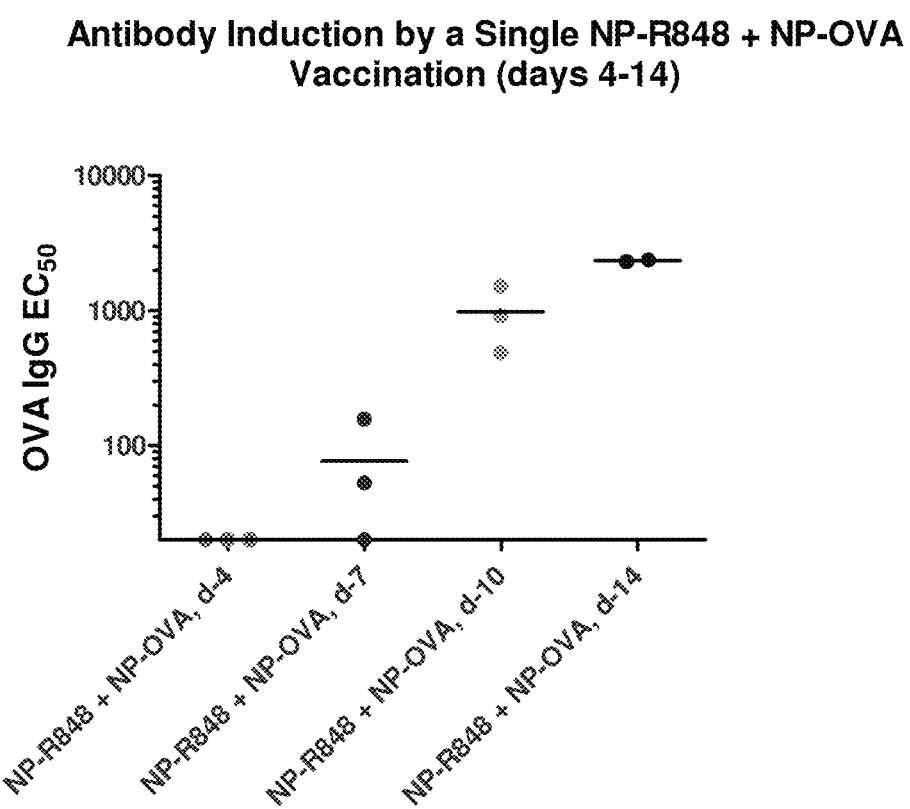
FIG. 7 shows the development of antibody titers after a single injection by NC-R848+NC-OVA. Individual titers and averages for each experimental group are shown. Nanocarrier=NC=NP.
Figure 8:
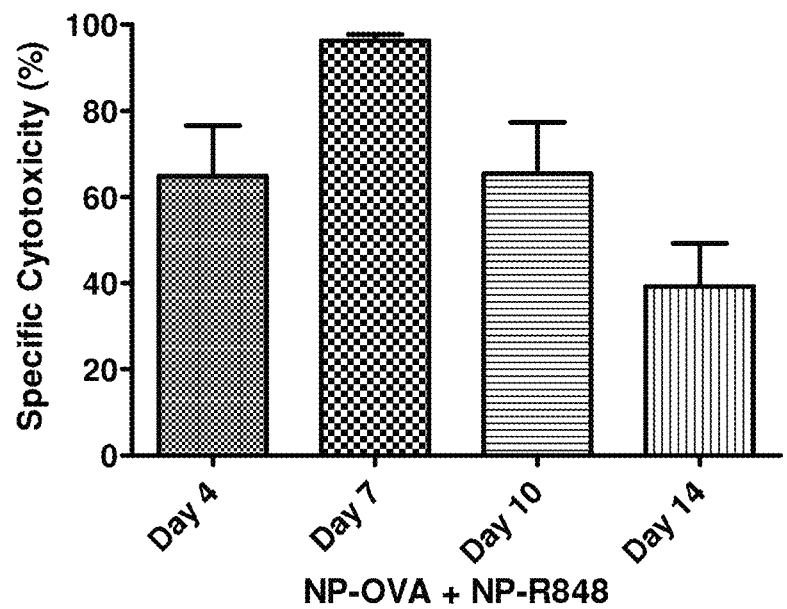
FIG. 8 shows the specific cytotoxicity in vivo after a single immunization with NC-R848+NC-OVA. Averages for each group with standard deviation are shown.
Figure 9:
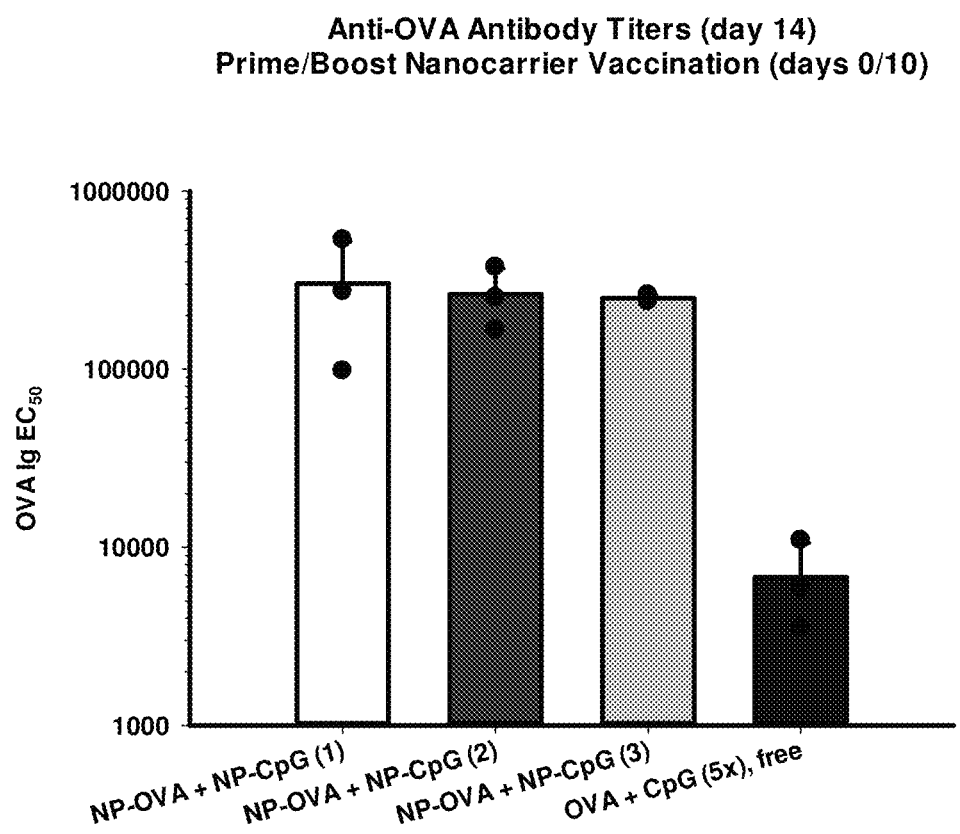
FIG. 9 shows the anti-ovalbumin antibody titers upon the immunization with nanocarriers carrying CpG and OVA vs. free CpG (5×) and OVA (5×).
Figure 10:
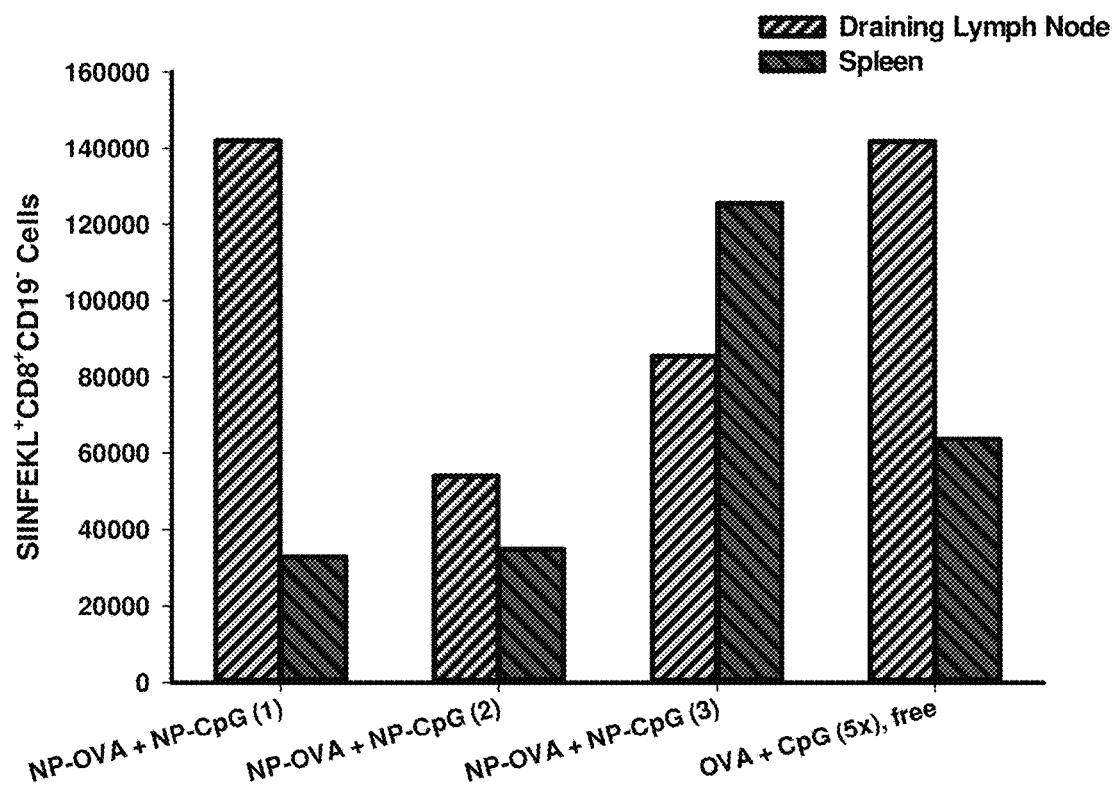
FIG. 10 shows the induction of OVA-specific CTL response in draining lymph nodes and spleens by the immunization with nanocarriers carrying CpG and OVA vs. free CpG (5×) and OVA (5×).
Figure 11:
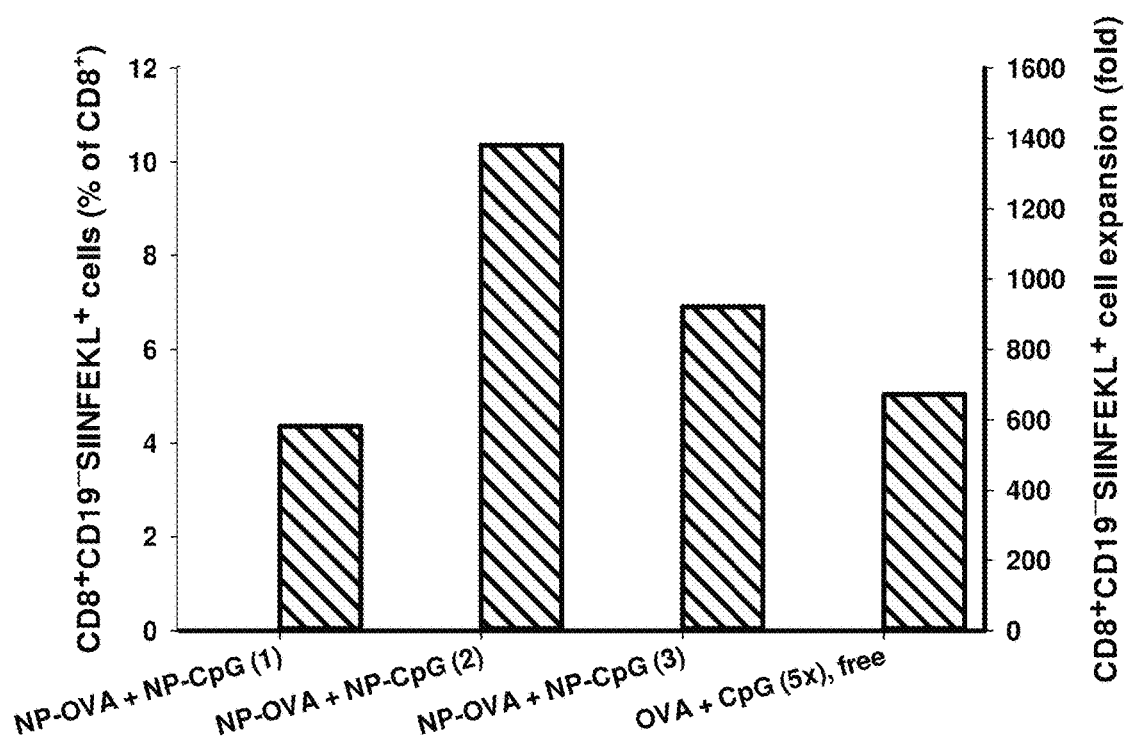
FIG. 11 shows the expansion of systemically induced OVA-specific CTLs in vitro upon the immunization with nanocarriers carrying CpG and OVA vs. free CpG (5×) and OVA (5×). Left Y axis (dark striped bars)-fraction of SIINFEKL (SEQ ID NO: 1)-specific CD8+ cells after expansion; right Y axis (light striped bars)-expansion potential presented as proportion of post- and pre-expansion SIINFEKL (SEQ ID NO: 1)-specific CTLs.

Before describing the present invention in detail, it is to be understood that this invention is not limited to particularly exemplified materials or process parameters as such may, of course, vary. It is also to be understood that the terminology used herein is for the purpose of describing particular embodiments of the invention only, and is not intended to be limiting of the use of alternative terminology to describe the present invention.

All publications, patents and patent applications cited herein, whether supra or infra, are hereby incorporated by reference in their entirety for all purposes.

As used in this specification and the appended claims, the singular forms "a," "an" and "the" include plural referents unless the content clearly dictates otherwise. For example, reference to "a polymer" includes a mixture of two or more such molecules or a mixture of differing molecular weights of a single polymer species, reference to "a synthetic nanocarrier" includes a mixture of two or more such synthetic nanocarriers or a plurality of such synthetic nanocarriers, reference to "a DNA molecule" includes a mixture of two or more such DNA molecules or a plurality of such DNA molecules, reference to "an adjuvant" includes mixture of two or more such adjuvant molecules or a plurality of such adjuvant molecules, and the like.

As used herein, the term "comprise" or variations thereof such as "comprises" or "comprising" are to be read to indicate the inclusion of any recited integer (e.g. a feature, element, characteristic, property, method/process step or limitation) or group of integers (e.g. features, elements, characteristics, properties, method/process steps or limitations) but not the exclusion of any other integer or group of integers. Thus, as used herein, the term "comprising" is inclusive and does not exclude additional, unrecited integers or method/process steps.

In embodiments of any of the compositions and methods provided herein, "comprising" may be replaced with "consisting essentially of" or "consisting of". The phrase "consisting essentially of" is used herein to require the specified integer(s) or steps as well as those which do not materially affect the character or function of the claimed invention. As used herein, the term "consisting" is used to indicate the presence of the recited integer (e.g. a feature, element, characteristic, property, method/process step or limitation) or group of integers (e.g. features, elements, characteristics, properties, method/process steps or limitations) alone.

A. Introduction

Treatment of challenging diseases such as of HIV, malaria, hepatitis B, and cancer with therapeutic or prophylactic vaccines may be enhanced by, or in some circumstances require, combined humoral and CTL immune responses. While vaccine approaches have been proposed for creating a combined CTL and humoral immune response, alternative approaches could provide valuable improvements in clinical efficacy, safety, and/or manufacturability. Provided herein are methods for using synthetic nanocarrier compositions, and related compositions, that are believed to have not been previously shown to generate strong and effective humoral and CTL immune responses. Such compositions can effectively target immune cells of interest to generate more effective immune responses.

The inventors have unexpectedly and surprisingly discovered that the problems and limitations noted above can be overcome by practicing the invention disclosed herein. In particular, it has been unexpectedly and surprisingly discovered that effective humoral and CTL immune responses can be generated with synthetic nanocarriers to which a protein, that comprises at least one humoral epitope and at least one MHC Class I-restricted epitope that are not the same epitope, is coupled, wherein the population of synthetic nanocarriers does not comprise a saponin-cholesterol adjuvant, and wherein the mean of a particle size distribution obtained using dynamic light scattering of the population of synthetic nanocarriers is a maximum dimension of from 20 nm to 250 nm. In one aspect, therefore, a method comprising administering such a composition is provided. In one embodiment, the method comprises identifying a subject in need of a humoral and CTL immune response to a first protein, and administering to the subject a composition comprising such synthetic nanocarriers. In some embodiments, the composition is in an amount effective to generate a humoral and CTL immune response to the first protein. In another embodiment, the method comprises administering such a composition to a subject according to a protocol that was previously shown to result in a humoral and CTL immune response specific to the first protein in one or more test subjects.

In embodiments, the immune responses that are generated are clinically effective. In some embodiments, the subject to which the compositions are administered may have or be at risk of having cancer, an infection or infectious disease or a non-autoimmune or degenerative disease. In other embodiments, the subject may have or be at risk of having HIV, malaria, leischmaniasis, a human filovirus infection, a togavirus infection, a alphavirus infection, an arenavirus infection, a bunyavirus infection, a flavivirus infection, a human papillomavirus infection, a human influenza A virus infection, a hepatitis B infection or a hepatitis C infection.

In other embodiments, the compositions are administered to a subject, such as a human, according to a vaccination regimen.

The invention will now be described in more detail below.

B. Definitions

"Adjuvant" means an agent that does not constitute a specific antigen, but boosts the strength and longevity of an immune response to a concomitantly administered antigen. Such adjuvants may include, but are not limited to stimulators of pattern recognition receptors, such as Toll-like receptors, RIG-1 and NOD-like receptors (NLR), mineral salts, such as alum, alum combined with monphosphoryl lipid (MPL) A of Enterobacteria, such as *Escherihia coli, Salmonella minnesota, Salmonella typhimurium,* or *Shigella flexneri* or specifically with MPL® (AS04), MPL A of above-mentioned bacteria separately, saponins, such as QS-21, Quil-A, ISCOMs, ISCOMATRIX™, emulsions such as MF59™, Montanide® ISA 51 and ISA 720, AS02 (QS21+squalene+MPL®), liposomes and liposomal formulations such as AS01, synthesized or specifically prepared microparticles and microcarriers such as bacteria-derived outer membrane vesicles (OMV) of *N. gonorrheae, Chlamydia trachomatis* and others, or chitosan particles, depot-forming agents, such as Pluronic® block co-polymers, specifically modified or prepared peptides, such as muramyl dipeptide, aminoalkyl glucosaminide 4-phosphates, such as RC529, or proteins, such as bacterial toxoids or toxin fragments. "Saponin-cholesterol adjuvants" are saponin adjuvants that are stabilized by admixture with cholesterol. Such adjuvants include, for example, ISCOMs and ISCO-MATRIX adjuvants. Preferably, in some embodiments, the synthetic nanocarriers provided herein are not or do not comprise such adjuvants. In other embodiments, the compositions provided herein do not comprise such adjuvants.

In embodiments, adjuvants comprise agonists for pattern recognition receptors (PRR), including, but not limited to Toll-Like Receptors (TLRs), specifically TLRs 2, 3, 4, 5, 7, 8, 9 and/or combinations thereof. In other embodiments, adjuvants comprise agonists for Toll-Like Receptors 3, agonists for Toll-Like Receptors 7 and 8, or agonists for Toll-Like Receptor 9; preferably the recited adjuvants comprise imidazoquinolines; such as R848; adenine derivatives, such as those disclosed in U.S. Pat. No. 6,329,381 (Sumitomo Pharmaceutical Company), US Published Patent Application 2010/0075995 to Biggadike et al., or WO 2010/018132 to Campos et al.; immunostimulatory DNA; or immunostimulatory RNA. In specific embodiments, synthetic nanocarriers incorporate as adjuvants compounds that are agonists for toll-like receptors (TLRs) 7 & 8 ("TLR 7/8 agonists"). Of utility are the TLR 7/8 agonist compounds disclosed in U.S. Pat. No. 6,696,076 to Tomai et al., including but not limited to imidazoquinoline amines, imidazopyridine amines, 6,7-fused cycloalkylimidazopyridine amines, and 1,2-bridged imidazoquinoline amines. Preferred adjuvants comprise imiquimod and resiquimod (also known as R848). In specific embodiments, an adjuvant may be an agonist for the DC surface molecule CD40. In certain embodiments, to stimulate immunity rather than tolerance, a synthetic nanocarrier incorporates an adjuvant that promotes DC maturation (needed for priming of naive T cells) and the production of cytokines, such as type I interferons, which promote antibody immune responses. In embodiments, adjuvants also may comprise immunostimulatory RNA molecules, such as but not limited to dsRNA, poly I:C or poly I:poly C12U (available as Ampligen®, both poly I:C and poly I:polyC12U being known as TLR3 stimulants), and/or those disclosed in F. Heil et al., "Species-Specific Recognition of Single-Stranded RNA via Toll-like Receptor 7 and 8" Science 303(5663), 1526-1529 (2004); J. Vollmer et al., "Immune modulation by chemically modified ribonucleosides and oligoribonucleotides" WO 2008033432 A2; A. Forsbach et al., "Immunostimulatory oligoribonucleotides containing specific sequence motif(s) and targeting the Toll-like receptor 8 pathway" WO 2007062107 A2; E. Uhlmann et al., "Modified oligoribonucleotide analogs with enhanced immunostimulatory activity" U.S. Pat. Appl. Publ. US 2006241076; G. Lipford et al., "Immunostimulatory viral RNA oligonucleotides and use for treating cancer and infections" WO 2005097993 A2; G. Lipford et al., "Immunostimulatory G,U-containing oligoribonucleotides, compositions, and screening methods" WO 2003086280 A2. In some embodiments, an adjuvant may be a TLR-4 agonist, such as bacterial lipopolysaccharide (LPS), VSV-G, and/or HMGB-1. In some embodiments, adjuvants may comprise TLR-5 agonists, such as flagellin, or portions or derivatives thereof, including but not limited to those disclosed in U.S. Pat. Nos. 6,130,082, 6,585,980, and 7,192,725. In specific embodiments, synthetic nanocarriers incorporate a ligand for Toll-like receptor (TLR)-9, such as immunostimulatory DNA molecules comprising CpGs, which induce type I interferon secretion, and stimulate T and B cell activation leading to increased antibody production and cytotoxic T cell responses (Krieg et al., CpG motifs in bacterial DNA trigger direct B cell activation. Nature. 1995. 374:546-549; Chu et al. CpG oligodeoxynucleotides act as adjuvants that switch on T helper 1 (Th1) immunity. J. Exp. Med. 1997. 186:1623-1631; Lipford et al. CpG-containing synthetic oligonucleotides promote B and cytotoxic T cell responses to protein antigen: a new class of vaccine adjuvants. Eur. J. Immunol. 1997. 27:2340-2344; Roman et al. Immunostimulatory DNA sequences function as T helper-1-promoting adjuvants. Nat. Med. 1997. 3:849-854; Davis et al. CpG DNA is a potent enhancer of specific immunity in mice immunized with recombinant hepatitis B surface antigen. J. Immunol. 1998. 160:870-876; Lipford et al., Bacterial DNA as immune cell activator. Trends Microbiol. 1998. 6:496-500; U.S. Pat. No. 6,207,646 to Krieg et al.; U.S. Pat. No. 7,223,398 to Tuck et al.; U.S. Pat. No. 7,250,403 to Van Nest et al.; or U.S. Pat. No. 7,566,703 to Krieg et al.

In some embodiments, adjuvants may be proinflammatory stimuli released from necrotic cells (e.g., urate crystals). In some embodiments, adjuvants may be activated components of the complement cascade (e.g., CD21, CD35, etc.). In some embodiments, adjuvants may be activated components of immune complexes. The adjuvants also include complement receptor agonists, such as a molecule that binds to CD21 or CD35. In some embodiments, the complement receptor agonist induces endogenous complement opsonization of the synthetic nanocarrier. In some embodiments, adjuvants are cytokines, which are small proteins or biological factors (in the range of 5 kD-20 kD) that are released by cells and have specific effects on cell-cell interaction, communication and behavior of other cells. In some embodiments, the cytokine receptor agonist is a small molecule, antibody, fusion protein, or aptamer.

In embodiments, at least a portion of the dose of adjuvant may be coupled to synthetic nanocarriers, preferably, all of the dose of adjuvant is coupled to synthetic nanocarriers. In other embodiments, at least a portion of the dose of the adjuvant is not coupled to the synthetic nanocarriers. In embodiments, the dose of adjuvant comprises two or more types of adjuvants. For instance, and without limitation, adjuvants that act on different TLR receptors may be combined. As an example, in an embodiment a TLR 7/8 agonist may be combined with a TLR 9 agonist. In another embodiment, a TLR 7/8 agonist may be combined with a TLR 9 agonist. In yet another embodiment, a TLR 9 agonist may be combined with a TLR 9 agonist.

"Administering" or "administration" means providing a material, such as a drug, to a subject in a manner that is pharmacologically useful.

"Amount effective" is any amount of a composition provided herein that produces one or more desired responses, such as one or more desired immune responses. This amount can be for in vitro or in vivo purposes. For in vivo purposes, the amount can be one that a clinician would believe may have a clinical benefit for a subject in need of a humoral immune response and a CTL immune response to a single protein. An effective amount that a clinician would believe may have a clinical benefit for such a subject is also referred to herein as a "clinically effective amount". In embodiments, both the humoral immune response and the CTL immune response that is elicited by a composition provided herein results in a clinical effect from each of these arms of the immune system. In other embodiments, clinically effective amounts are effective amounts that can be helpful in the treatment of a subject with a disease or condition in which a humoral immune response and a CTL immune response to a single protein would provide a benefit. Such subjects include, in some embodiments, those that have or are at risk of having cancer, an infection or infectious disease or a non-autoimmune or degenerative disease. In other embodiments, such subjects include those that have or are at risk of having HIV, malaria, leischmaniasis, a human filovirus infection, a togavirus infection, a alphavirus infection, an arenavirus infection, a bunyavirus infection, a flavivirus infection, a human papillomavirus infection, a human influenza A virus infection, a hepatitis B infection or a hepatitis C infection.

Amounts effective include those that involve the production of a humoral immune response against a humoral epitope and a CTL immune response against a MHC Class I-restricted epitope administered in one of the compositions provided herein. A subject's humoral and CTL immune response can be monitored by routine methods. An amount that is effective to produce the desired immune responses as provided herein can also be an amount of a composition provided herein that produces a desired therapeutic endpoint or a desired therapeutic result. In one embodiment, the amount that is effective is one that provides effective immunity against a disease or agent that causes a disease as provided herein. In another embodiment, the immunity persists in the subject for at least 6, 12, 18, 24, 36, 48, 60 or more months. In still another embodiment, the immunity results or persists due to the administration of a composition provided herein according to a vaccination regimen.

Amounts effective will depend, of course, on the particular subject being treated; the severity of a condition, disease or disorder; the individual patient parameters including age, physical condition, size and weight; the duration of the treatment; the nature of concurrent therapy (if any); the specific route of administration and like factors within the knowledge and expertise of the health practitioner. These factors are well known to those of ordinary skill in the art and can be addressed with no more than routine experimentation. It is generally preferred that a maximum dose be used, that is, the highest safe dose according to sound medical judgment. It will be understood by those of ordinary skill in the art, however, that a patient may insist upon a lower dose or tolerable dose for medical reasons, psychological reasons or for virtually any other reason.

In general, doses of the compositions of the invention can range from about 10 µg/kg to about 100,000 µg/kg. In some embodiments, the doses can range from about 0.1 mg/kg to about 100 mg/kg. In still other embodiments, the doses can range from about 0.1 mg/kg to about 25 mg/kg, about 25 mg/kg to about 50 mg/kg, about 50 mg/kg to about 75 mg/kg or about 75 mg/kg to about 100 mg/kg. Alternatively, the dose can be administered based on the number of synthetic nanocarriers. For example, useful doses include greater than $10^6$, $10^7$, $10^8$, $10^9$ or $10^{10}$ synthetic nanocarriers per dose. Other examples of useful doses include from about $1 \times 10^6$ to about $1 \times 10^{10}$, about $1 \times 10^7$ to about $1 \times 10^9$ or about $1 \times 10^8$ to about $1 \times 10^9$ synthetic nanocarriers per dose.

"Antigen" means any antigen that can generate one or more immune responses. The antigen may be one that generates a humoral and/or CTL immune response. Such antigens include, but are not limited to proteins, peptides, small molecules, oligosaccharides, and carbohydrates. In some embodiments, such an antigen comprises a non-protein antigen (i.e., not a protein or peptide antigen). In some embodiments, an antigen that generates a humoral immune response comprises a carbohydrate associated with an infectious agent. In some embodiments, an antigen that generates a humoral immune response comprises a glycoprotein or glycopeptide associated with an infectious agent. The infectious agent can be a bacterium, virus, fungus, protozoan, or parasite. Antigens may be B cell or T cell antigens.

The synthetic nanocarrier compositions for use in the inventive methods provided herein are coupled to an antigen that is a protein that comprises at least one humoral epitope and at least one MHC Class I-restricted epitope that is not the same epitope. Such compositions can, in some embodiments, comprise one or more additional antigens that may also be so limited but not necessarily so. The one or more additional antigens for use in the methods and compositions provided herein can be any antigen, which include antigens that comprise humoral epitopes and/or MHC Class I-restricted epitopes. The one or more additional antigens may also include MHC Class II-restricted epitopes. In other embodiments, the one or more additional antigens may be any antigen that generates a humoral immune response. In still other embodiments, the one or more additional antigens may be any of the T cell antigens described herein, including a CD-1 restricted antigen. In yet other embodiments, the one or more additional antigens may be a protein, peptide, small molecule, oligosaccharide and carbohydrate.

In embodiments, antigens, including a protein that comprises at least one humoral epitope and at least one MHC Class I-restricted epitope that are not the same epitope, are coupled to the synthetic nanocarriers. In other embodiments, the antigens are not coupled to the synthetic nanocarriers. In yet other embodiments, the antigens are encapsulated in the synthetic nanocarriers. "Type(s) of antigens" means molecules that share the same, or substantially the same, antigenic characteristics.

"Antigens associated" with a disease, disorder or condition provided herein are antigens that can generate an undesired immune response against, as a result of, or in conjunction with the disease, disorder or condition; the cause of the disease, disorder or condition (or a symptom or effect thereof); and/or can generate an undesired immune response that is a symptom, result or effect of the disease, disorder or condition. In some embodiments, such as with cancer, such antigens are expressed in or on diseased cells, such as cancer or tumor cells, but not in or on normal or healthy cells (or non-diseased cells). Such antigens can also comprise an antigen that is expressed in or on diseased cells and on normal or healthy cells (or non-diseased cells) but is expressed in or on diseased cells at a greater level than on normal or healthy cells (or non-diseased cells). Preferably, the use of an antigen associated with a disease or condition provided herein will not lead to a substantial or detrimental immune response against normal or healthy cells or will lead to a beneficial immune response against the disease or condition that outweighs any immune response against normal or healthy cells (or non-diseased cells). The antigens associated with a disease or condition provided herein, in some embodiments, are proteins that are coupled to synthetic nanocarriers that comprise humoral and/or MHC Class I-restricted epitopes. In other embodiments, such proteins comprise a humoral and a MHC Class I-restricted epitope. In still other embodiments, such proteins comprise at least one humoral epitope and at least one MHC Class I-restricted epitope that are not the same epitope. Examples of antigens, including the foregoing proteins, are provided elsewhere herein.

"At least a portion of the dose" means at least some part of the dose, ranging up to including all of the dose.

An "at risk" subject is one in which a health practitioner believes has a chance of having a disease or condition as provided herein.

"B cell antigen" means any antigen that is recognized by or triggers an immune response in a B cell (e.g., an antigen that is specifically recognized by a B cell or a receptor thereon). In some embodiments, an antigen that is a T cell antigen is also a B cell antigen. In other embodiments, the T cell antigen is not also a B cell antigen. B cell antigens include, but are not limited to, proteins, peptides, small molecules, oligosaccharides and carbohydrates.

"Couple" or "Coupled" or "Couples" (and the like) means to chemically associate one entity (for example a moiety) with another. In some embodiments, the coupling is covalent, meaning that the coupling occurs in the context of the presence of a covalent bond between the two entities. In non-covalent embodiments, the non-covalent coupling is mediated by non-covalent interactions including but not limited to charge interactions, affinity interactions, metal coordination, physical adsorption, host-guest interactions, hydrophobic interactions, TT stacking interactions, hydrogen bonding interactions, van der Waals interactions, magnetic interactions, electrostatic interactions, dipole-dipole interactions, and/or combinations thereof. In embodiments, encapsulation is a form of coupling.

"Cytotoxic T lymphocyte (CTL) immune response" means any stimulation, induction or proliferation of cytotoxic T cells, preferably cytotoxic T cells that are specific to an epitope, such as a MHC Class I-restricted epitope. In embodiments, the epitope is or is of an antigen that is associated with any of the diseases or conditions provided herein. Methods for assessing CTL immune responses are known to those of skill in the art. Examples of such a method are provided in the EXAMPLES.

"Dosage form" means a pharmacologically and/or immunologically active material in a medium, carrier, vehicle, or device suitable for administration to a subject.

"Encapsulate" means to enclose at least a portion of a substance within a synthetic nanocarrier. In some embodiments, a substance is enclosed completely within a synthetic nanocarrier. In other embodiments, most or all of a substance that is encapsulated is not exposed to the local environment external to the synthetic nanocarrier. In other embodiments, no more than 50%, 40%, 30%, 20%, 10% or 5% (weight/weight) is exposed to the local environment. Encapsulation is distinct from absorption, which places most or all of a substance on a surface of a synthetic nanocarrier, and leaves the substance exposed to the local environment external to the synthetic nanocarrier.

"Epitope", also known as an antigenic determinant, is the part of an antigen that is recognized by the immune system, specifically by, for example, antibodies, B cells, or T cells. As used herein, a "humoral epitope" is one that is recognized by antibodies or B cells, while a "MHC Class I-restricted epitope" is one that is presented to immune cells by MHC class I molecules found on nucleated cells. "MHC Class II-restricted epitopes" are epitopes that are presented to immune cells by MHC class II molecules found on antigen presenting cells (APCs), for example, on professional antigen-presenting immune cells, such as on macrophages, B cells, and dendritic cells, or on non-hematopoietic cells, such as hepatocytes.

A number of epitopes are known to those of skill in the art, and exemplary epitopes suitable according to some aspects of this invention include, but are not limited to those listed in the Immune Epitope Database (www.immuneepitope.org, Vita R, Zarebski L, Greenbaum J A, Emami H, Hoof I, Salimi N, Damle R, Sette A, Peters B. The immune epitope database 2.0. Nucleic Acids Res. 2010 January; 38(Database issue):D854-62; the entire contents of which as well as all database entries of IEDB version 2.4, August 2011, and particularly all epitopes disclosed therein, are incorporated herein by reference). Epitopes can also be identified with publicly available algorithms, for example, the algorithms described in Wang P, Sidney J, Kim Y, Sette A, Lund O, Nielsen M, Peters B. 2010. peptide binding predictions for HLA DR, DP and DQ molecules. BMC Bioinformatics 2010, 11:568; Wang P, Sidney J, Dow C, Mothé B, Sette A, Peters B. 2008. A systematic assessment of MHC class II peptide binding predictions and evaluation of a consensus approach. PLoS Comput Biol. 4(4):e1000048; Nielsen M, Lund O. 2009. N,N-align. An artificial neural network-based alignment algorithm for MHC class II peptide binding prediction. BMC Bioinformatics. 10:296; Nielsen M, Lundegaard C, Lund O. 2007. Prediction of MHC class II binding affinity using SMM-align, a novel stabilization matrix alignment method. BMC Bioinformatics. 8:238; Bui H H, Sidney J, Peters B, Sathiamurthy M, Sinichi A, Purton K A, Mothé B R, Chisari F V, Watkins D I, Sette A. 2005. Immunogenetics. 57:304-314; Sturniolo T, Bono E, Ding J, Raddrizzani L, Tuereci O, Sahin U, Braxenthaler M, Gallazzi F, Protti M P, Sinigaglia F, Hammer J. 1999. Generation of tissue-specific and promiscuous HLA ligand databases using DNA microarrays and virtual HLA class II matrices. Nat. Biotechnol. 17(6):555-561; Nielsen M, Lundegaard C, Worning P, Lauemoller S L, Lamberth K, Buus S, Brunak S, Lund O. 2003. Reliable prediction of T-cell epitopes using neural networks with novel sequence representations. Protein Sci 12:1007-1017; Bui H H, Sidney J, Peters B, Sathiamurthy M, Sinichi A, Purton K A, Mothé B R, Chisari F V, Watkins D I, Sette A. 2005. Automated generation and evaluation of specific MHC binding predictive tools: ARB matrix applications. Immunogenetics 57:304-314; Peters B, Sette A. 2005. Generating quantitative models describing the sequence specificity of biological processes with the stabilized matrix method. BMC Bioinformatics 6:132; Chou P Y, Fasman G D. 1978. Prediction of the secondary structure of proteins from their amino acid sequence. Adv Enzymol Relat Areas Mol Biol 47:45-148; Emini E A, Hughes J V, Perlow D S, Boger J. 1985. Induction of hepatitis A virus-neutralizing antibody by a virus-specific synthetic peptide. J Virol 55:836-839; Karplus P A, Schulz G E. 1985. Prediction of chain flexibility in proteins. Naturwissenschaften 72:212-213; Kolaskar A S, Tongaonkar P C. 1990. A semi-empirical method for prediction of antigenic determinants on protein antigens. FEBS Lett 276:172-174; Parker J M, Guo D, Hodges R S. 1986. New hydrophilicity scale derived from high-performance liquid chromatography peptide retention data: correlation of predicted surface residues with antigenicity and X-ray-derived accessible sites. Biochemistry 25:5425-5432; Larsen J E, Lund O, Nielsen M. 2006. Improved method for predicting linear B-cell epitopes. Immunome Res 2:2; Ponomarenko J V, Bourne P E. 2007. Antibody-protein interactions: benchmark datasets and prediction tools evaluation. BMC Struct Biol 7:64; Haste Andersen P, Nielsen M, Lund O. 2006. Prediction of residues in discontinuous B-cell epitopes using protein 3D structures. Protein Sci 15:2558-2567; Ponomarenko J V, Bui H, Li W, Fusseder N, Bourne P E, Sette A, Peters B. 2008. ElliPro: a new structure-based tool for the prediction of antibody epitopes. BMC Bioinformatics 9:514; Nielsen M, Lundegaard C, Blicher T, Peters B, Sette A, Justesen S, Buus S, and Lund 0.2008. PLoS Comput Biol. 4(7)e1000107. Quantitative predictions of peptide binding to any HLA-DR molecule of known sequence: NetMHCIIpan; the entire contents of each of which are incorporated herein by reference for disclosure of methods and algorithms for the identification of epitopes.

"Generating" means causing an action, such as an immune response (e.g., a humoral immune response or a CTL immune response) against an epitope to occur, either directly oneself or indirectly, such as, but not limited to, an unrelated third party that takes an action through reliance on one's words or deeds.

"Humoral immune response" means any immune response that results in the production or stimulation of B cells and/or the production of antibodies. Preferably, the humoral immune response is specific to an epitope comprised within an inventive composition or administered during the practice of an inventive method. Methods for assessing whether a humoral response is induced are known to those of ordinary skill in the art. The production of antibodies is referred to herein as an "antibody response". "Antibody titer" means the production of a measurable level of antibodies. Preferably, the antibody response or generation of the antibody titer is in a human. In some embodiments, the antibodies are antibodies of a certain isotype, such as IgG or a subclass thereof. Methods for measuring antibody titers are known in the art and include Enzyme-linked Immunosorbent Assay (ELISA). Methods for measuring antibody titers are also described in some detail in the EXAMPLES. Preferably, the antibody response or antibody titer is specific to an epitope as provided herein. In embodiments, the antibody response can be quantitated, for example, as the number of antibodies, concentration of antibodies or titer. The values can be absolute or they can be relative. Assays for quantifying an antibody response include antibody capture assays, enzyme-linked immunosorbent assays (ELISAs), inhibition liquid phase absorption assays (ILPAAs), rocket immunoelectrophoresis (RIE) assays and line immunoelectrophoresis (LIE) assays. When an antibody response is compared to another antibody response the same type of quantitative value (e.g., titer) and method of measurement (e.g., ELISA) is preferably used to make the comparison.

An ELISA method for measuring an antibody titer, for example, may consist of the following steps (i) preparing an ELISA-plate coating material such that the antibody target of interest is coupled to a substrate polymer or other suitable material (ii) preparing the coating material in an aqueous solution (such as PBS) and delivering the coating material solution to the wells of a multiwell plate for overnight deposition of the coating onto the multiwell plate (iii) thoroughly washing the multiwell plate with wash buffer (such as 0.05% Tween-20 in PBS) to remove excess coating material (iv) blocking the plate for nonspecific binding by applying a diluent solution (such as 10% fetal bovine serum in PBS), (v) washing the blocking/diluent solution from the plate with wash buffer (vi) diluting the serum sample(s) containing antibodies and appropriate standards (positive controls) with diluent as required to obtain a concentration that suitably saturates the ELISA response (vii) serially diluting the plasma samples on the multiwell plate such to cover a range of concentrations suitable for generating an ELISA response curve (viii) incubating the plate to provide for antibody-target binding (ix) washing the plate with wash buffer to remove antibodies not bound to antigen (x) adding an appropriate concentration of a secondary detection antibody in same diluent such as a biotin-coupled detection antibody capable of binding the primary antibody (xi) incubating the plate with the applied detection antibody, followed by washing with wash buffer (xii) adding an enzyme such as streptavidin-HRP (horse radish peroxidase) that will bind to biotin found on biotinylated antibodies and incubating (xiii) washing the multiwell plate (xiv) adding substrate(s) (such as TMB solution) to the plate (xv) applying a stop solution (such as 2N sulfuric acid) when color development is complete (xvi) reading optical density of the plate wells at a specific wavelength for the substrate (450 nm with subtraction of readings at 570 nm) (xvi) applying a suitable multiparameter curve fit to the data and defining half-maximal effective concentration (EC50) as the concentration on the curve at which half the maximum OD value for the plate standards is achieved.

"Identifying" is any action or set of actions that allows a clinician to recognize a subject as one who may benefit from the methods and compositions provided herein. Preferably, the identified subject is one who is in need of a humoral immune response and CTL immune response to a single protein. Such subjects include any subject that has or is at risk of having any of the disease or conditions provided herein. The action or set of actions may be either directly oneself or indirectly, such as, but not limited to, an unrelated third party that takes an action through reliance on one's words or deeds.

An "infection" or "infectious disease" is any condition or disease caused by a microorganism, pathogen or other agent, such as a bacterium, fungus, prion or virus.

"Maximum dimension of a synthetic nanocarrier" means the largest dimension of a nanocarrier measured along any axis of the synthetic nanocarrier. "Minimum dimension of a synthetic nanocarrier" means the smallest dimension of a synthetic nanocarrier measured along any axis of the synthetic nanocarrier. For example, for a spheroidal synthetic nanocarrier, the maximum and minimum dimension of a synthetic nanocarrier would be substantially identical, and would be the size of its diameter. Similarly, for a cuboidal synthetic nanocarrier, the minimum dimension of a synthetic nanocarrier would be the smallest of its height, width or length, while the maximum dimension of a synthetic nanocarrier would be the largest of its height, width or length. In an embodiment, a minimum dimension of at least 75%, preferably at least 80%, more preferably at least 90%, of the synthetic nanocarriers in a sample, based on the total number of synthetic nanocarriers in the sample, is equal to or greater than 100 nm. In an embodiment, a maximum dimension of at least 75%, preferably at least 80%, more preferably at least 90%, of the synthetic nanocarriers in a sample, based on the total number of synthetic nanocarriers in the sample, is equal to or less than 5 µm. Preferably, a minimum dimension of at least 75%, preferably at least 80%, more preferably at least 90%, of the synthetic nanocarriers in a sample, based on the total number of synthetic nanocarriers in the sample, is greater than 110 nm, more preferably greater than 120 nm, more preferably greater than 130 nm, and more preferably still greater than 150 nm. Aspects ratios of the maximum and minimum dimensions of inventive synthetic nanocarriers may vary depending on the embodiment. For instance, aspect ratios of the maximum to minimum dimensions of the synthetic nanocarriers may vary from 1:1 to 1,000,000:1, preferably from 1:1 to 100,000:1, more preferably from 1:1 to 10,000:1, more preferably from 1:1 to 1000:1, still more preferably from 1:1 to 100:1, and yet more preferably from 1:1 to 10:1. Preferably, a maximum dimension of at least 75%, preferably at least 80%, more preferably at least 90%, of the synthetic nanocarriers in a sample, based on the total number of synthetic nanocarriers in the sample is equal to or less than 3 µm, more preferably equal to or less than 2 µm, more preferably equal to or less than 1 µm, more preferably equal to or less than 800 nm, more preferably equal to or less than 600 nm, and more preferably still equal to or less than 500 nm. In preferred embodiments, a minimum dimension of at least 75%, preferably at least 80%, more preferably at least 90%, of the synthetic nanocarriers in a sample, based on the total number of synthetic nanocarriers in the sample, is equal to or greater than 100 nm, more preferably equal to or greater than 120 nm, more preferably equal to or greater than 130 nm, more preferably equal to or greater than 140 nm, and more preferably still equal to or greater than 150 nm. Measurement of synthetic nanocarrier dimensions (e.g., diameter) is obtained by suspending the synthetic nanocarriers in a liquid (usually aqueous) media and using dynamic light scattering (DLS) (e.g. using a Brookhaven ZetaPALS instrument). For example, a suspension of synthetic nanocarriers can be diluted from an aqueous buffer into purified water to achieve a final synthetic nanocarrier suspension concentration of approximately 0.01 to 0.1 mg/mL. The diluted suspension may be prepared directly inside, or transferred to, a suitable cuvette for DLS analysis. The cuvette may then be placed in the DLS, allowed to equilibrate to the controlled temperature, and then scanned for sufficient time to acquire a stable and reproducible distribution based on appropriate inputs for viscosity of the medium and refractive indicies of the sample. The effective diameter, or mean of the distribution, is then reported. "Dimension" or "size" or "diameter" of synthetic nanocarriers means the mean of a particle size distribution obtained using dynamic light scattering.

"MHC" refers to major histocompatibility complex, a large genomic region or gene family found in most vertebrates that encodes MHC molecules that display fragments or epitopes of processed proteins on the cell surface. The presentation of MHC:peptide on cell surfaces allows for surveillance by immune cells, usually a T cell. There are two general classes of MHC molecules: Class I and Class II. Generally, Class I MHC molecules are found on nucleated cells and present peptides to cytotoxic T cells. Class II MHC molecules are found on certain immune cells, chiefly macrophages, B cells and dendritic cells, collectively known as APCs. The best-known genes in the MHC region are the subset that encodes antigen-presenting proteins on the cell surface. In humans, these genes are referred to as human leukocyte antigen (HLA) genes.

"Pharmaceutically acceptable excipient" means a pharmacologically inactive material used together with the recited synthetic nanocarriers to formulate the compositions. Pharmaceutically acceptable excipients comprise a variety of materials known in the art, including but not limited to saccharides (such as glucose, lactose, and the like), preservatives such as antimicrobial agents, reconstitution aids, colorants, saline (such as phosphate buffered saline), and buffers.

"Protein(s)" means compounds, typically having a molecular weight greater than 1000 daltons, comprising amino acid residues joined together primarily by peptide bonds between the carboxyl and amino groups of adjacent amino acid residues. Proteins may also comprise additional bonding structures such as secondary structures, tertiary structures, and the like. Certain of the peptide bonds in proteins may be replaced by other bond types, for various purposes, such as stabilization or coupling. When coupled to synthetic nanocarriers, preferably, there are multiple copies of the protein that are coupled to each synthetic nanocarrier.

"Protocol" refers to any dosing regimen of one or more substances to a subject. A dosing regimen may include the amount, frequency and/or mode of administration. In some embodiments, such a protocol may be used to administer one or more compositions of the invention to one or more test subjects. Immune responses in these test subjects can then be assessed to determine whether or not the protocol was effective in generating desired immune response(s). Any other therapeutic and/or prophylactic effects may also be assessed instead of or in addition to the aforementioned immune responses. Whether or not a protocol had a desired effect can be determined using any of the methods provided herein or otherwise known in the art. For example, a population of cells may be obtained from a subject to which a composition provided herein has been administered according to a specific protocol in order to determine whether or not specific immune cells, cytokines, antibodies, etc. were generated, activated, etc. Useful methods for detecting the presence and/or number of immune cells include, but are not limited to, flow cytometric methods (e.g., FACS) and immunohistochemistry methods. Antibodies and other binding agents for specific staining of immune cell markers, are commercially available. Such kits typically include staining reagents for multiple antigens that allow for FACS-based detection, separation and/or quantitation of a desired cell population from a heterogeneous population of cells.

"Subject" means animals, including warm blooded mammals such as humans and primates; avians; domestic household or farm animals such as cats, dogs, sheep, goats, cattle, horses and pigs; laboratory animals such as mice, rats and guinea pigs; fish; reptiles; zoo and wild animals; and the like.

"Synthetic nanocarrier(s)" means a discrete object that is not found in nature, and that possesses at least one dimension that is less than or equal to 5 microns in size. Albumin nanoparticles are generally included as synthetic nanocarriers, however in certain embodiments the synthetic nanocarriers do not comprise albumin nanoparticles. In embodiments, synthetic nanocarriers do not comprise chitosan. In certain other embodiments, the synthetic nanocarriers do not comprise chitosan. In other embodiments, inventive synthetic nanocarriers are not lipid-based nanoparticles. In further embodiments, inventive synthetic nanocarriers do not comprise a phospholipid.

A synthetic nanocarrier can be, but is not limited to, one or a plurality of lipid-based nanoparticles (also referred to herein as lipid nanoparticles, i.e., nanoparticles where the majority of the material that makes up their structure are lipids), polymeric nanoparticles, metallic nanoparticles, surfactant-based emulsions, dendrimers, buckyballs, nanowires, virus-like particles (i.e., particles that are primarily made up of viral structural proteins but that are not infectious or have low infectivity), peptide or protein-based particles (also referred to herein as protein particles, i.e., particles where the majority of the material that makes up their structure are peptides or proteins) (such as albumin nanoparticles) and/or nanoparticles that are developed using a combination of nanomaterials such as lipid-polymer nanoparticles. Synthetic nanocarriers may be a variety of different shapes, including but not limited to spheroidal, cuboidal, pyramidal, oblong, cylindrical, toroidal, and the like. Synthetic nanocarriers according to the invention comprise one or more surfaces. Exemplary synthetic nanocarriers that can be adapted for use in the practice of the present invention comprise: (1) the biodegradable nanoparticles disclosed in U.S. Pat. No. 5,543,158 to Gref et al., (2) the polymeric nanoparticles of Published US Patent Application 20060002852 to Saltzman et al., (3) the lithographically constructed nanoparticles of Published US Patent Application 20090028910 to DeSimone et al., (4) the disclosure of WO 2009/051837 to von Andrian et al., (5) the nanoparticles disclosed in Published US Patent Application 2008/0145441 to Penades et al., (6) the protein nanoparticles disclosed in Published US Patent Application 20090226525 to de los Rios et al., (7) the virus-like particles disclosed in published US Patent Application 20060222652 to Sebbel et al., (8) the nucleic acid coupled virus-like particles disclosed in published US Patent Application 20060251677 to Bachmann et al., (9) the virus-like particles disclosed in WO2010047839A1 or WO2009106999A2, (10) the nano-precipitated nanoparticles disclosed in P. Paolicelli et al., "Surface-modified PLGA-based Nanoparticles that can Efficiently Associate and Deliver Virus-like Particles" Nanomedicine. 5(6):843-853 (2010) or (11) apoptotic cells, apoptotic bodies or the synthetic or semisynthetic mimics disclosed in U.S. Publication 2002/0086049. In embodiments, synthetic nanocarriers may possess an aspect ratio greater than 1:1, 1:1.2, 1:1.5, 1:2, 1:3, 1:5, 1:7, or greater than 1:10.

Synthetic nanocarriers according to the invention that have a minimum dimension of equal to or less than about 100 nm, preferably equal to or less than 100 nm, do not comprise a surface with hydroxyl groups that activate complement or alternatively comprise a surface that consists essentially of moieties that are not hydroxyl groups that activate complement. In a preferred embodiment, synthetic nanocarriers according to the invention that have a minimum dimension of equal to or less than about 100 nm, preferably equal to or less than 100 nm, do not comprise a surface that substantially activates complement or alternatively comprise a surface that consists essentially of moieties that do not substantially activate complement. In a more preferred embodiment, synthetic nanocarriers according to the invention that have a minimum dimension of equal to or less than about 100 nm, preferably equal to or less than 100 nm, do not comprise a surface that activates complement or alternatively comprise a surface that consists essentially of moieties that do not activate complement. In embodiments, synthetic nanocarriers exclude virus-like particles. In embodiments, when synthetic nanocarriers comprise virus-like particles, the virus-like particles comprise non-natural adjuvant (meaning that the VLPs comprise an adjuvant other than naturally occurring RNA generated during the production of the VLPs). In embodiments, synthetic nanocarriers may possess an aspect ratio greater than 1:1, 1:1.2, 1:1.5, 1:2, 1:3, 1:5, 1:7, or greater than 1:10.

"T cell antigen" means any antigen that is recognized by and triggers an immune response in a T cell (e.g., an antigen that is specifically recognized by a T cell receptor on a T cell or an NKT cell via presentation of the antigen or portion thereof bound to a Class I or Class II major histocompatability complex molecule (MHC), or bound to a CD1 complex). In some embodiments, an antigen that is a T cell antigen is also a B cell antigen. In other embodiments, the T cell antigen is not also a B cell antigen. T cell antigens generally are proteins or peptides. T cell antigens may be an antigen that stimulates a CD8+ T cell response, a CD4+ T cell response, or both. The nanocarriers, therefore, in some embodiments can effectively stimulate both types of responses.

In some embodiments the T cell antigen is a T helper cell antigen (i.e. one that can generate an enhanced response to a B cell antigen, preferably an unrelated B cell antigen, through stimulation of T cell help). In embodiments, a T helper cell antigen may comprise one or more peptides obtained or derived from tetanus toxoid, Epstein-Barr virus, influenza virus, respiratory syncytial virus, measles virus, mumps virus, rubella virus, cytomegalovirus, adenovirus, diphtheria toxoid, or a PADRE peptide (known from the work of Sette et al. U.S. Pat. No. 7,202,351). In other embodiments, a T helper cell antigen may comprise one or more lipids, or glycolipids, including but not limited to: α-galactosylceramide (α-GalCer), α-linked glycosphingolipids (from *Sphingomonas* spp.), galactosyl diacylglycerols (from *Borrelia burgdorferi*), lypophosphoglycan (from *Leishmania donovani*), and phosphatidylinositol tetramannoside (PIM4) (from *Mycobacterium leprae*). For additional lipids and/or glycolipids useful as a T helper cell antigen, see V. Cerundolo et al., "Harnessing invariant NKT cells in vaccination strategies." Nature Rev Immun, 9:28-38 (2009). In embodiments, CD4+ T-cell antigens may be derivatives of a CD4+ T-cell antigen that is obtained from a source, such as a natural source. In such embodiments, CD4+ T-cell antigen sequences, such as those peptides that bind to MHC II, may have at least 70%, 80%, 90%, or 95% identity to the antigen obtained from the source. In embodiments, the T cell antigen, preferably a T helper cell antigen, may be coupled to, or uncoupled from, a synthetic nanocarrier. In some embodiments, the T cell antigen is encapsulated in the synthetic nanocarriers of the compositions.

"Vaccine" means a composition of matter that improves the immune response to a particular pathogen or disease. A vaccine typically contains factors that stimulate a subject's immune system to recognize a specific antigen as foreign and eliminate it from the subject's body. A vaccine also establishes an immunologic 'memory' so the antigen will be quickly recognized and responded to if a person is re-challenged. Vaccines can be prophylactic (for example to prevent future infection by any pathogen), or therapeutic (for example a vaccine against a tumor specific antigen for the treatment of cancer). In embodiments, a vaccine may comprise dosage forms according to the invention.

"Vaccine regimen" or "vaccination regimen" is a schedule of one or more vaccinations that includes the number and timing of doses of a vaccine. Generally, vaccination regimens are intended to achieve immunity against the development of a disease or condition. Preferably, the vaccine regimen is one that achieves immunity via both the humoral and CTL arms of the immune system.

C. Compositions for Use in the Inventive Methods

Provided herein are methods and related compositions for effective humoral and CTL immune response generation. It has been found that synthetic nanocarriers to which a protein that comprises at least one humoral epitope and at least one MHC Class I-restricted epitope that are not the same epitope, is coupled, wherein the synthetic nanocarriers do not comprise a saponin-cholesterol adjuvant, and wherein the mean of a particle size distribution obtained using dynamic light scattering of the population of synthetic nanocarriers is a maximum dimension of from 20 nm to 250 nm can be used to generate effective and strong humoral and CTL immune responses. The compositions provided can be used for a variety of desired clinical endpoints such as for vaccination.

A wide variety of synthetic nanocarriers can be used according to the invention. In some embodiments, synthetic nanocarriers are spheres or spheroids. In some embodiments, synthetic nanocarriers are flat or plate-shaped. In some embodiments, synthetic nanocarriers are cubes or cubic. In some embodiments, synthetic nanocarriers are ovals or ellipses. In some embodiments, synthetic nanocarriers are cylinders, cones, or pyramids.

In some embodiments, it is desirable to use a population of synthetic nanocarriers that is relatively uniform in terms of size, shape, and/or composition so that each synthetic nanocarrier has similar properties. For example, at least 80%, at least 90%, or at least 95% of the synthetic nanocarriers, based on the total number of synthetic nanocarriers, may have a minimum dimension or maximum dimension that falls within 5%, 10%, or 20% of the average diameter or average dimension of the synthetic nanocarriers. In some embodiments, a population of synthetic nanocarriers may be heterogeneous with respect to size, shape, and/or composition.

Synthetic nanocarriers can be solid or hollow and can comprise one or more layers. In some embodiments, each layer has a unique composition and unique properties relative to the other layer(s). To give but one example, synthetic nanocarriers may have a core/shell structure, wherein the core is one layer (e.g. a polymeric core) and the shell is a second layer (e.g. a lipid bilayer or monolayer). Synthetic nanocarriers may comprise a plurality of different layers.

In some embodiments, synthetic nanocarriers may comprise metal particles, quantum dots, ceramic particles, etc. In some embodiments, a non-polymeric synthetic nanocarrier is an aggregate of non-polymeric components, such as an aggregate of metal atoms (e.g., gold atoms).

In some embodiments, synthetic nanocarriers may optionally comprise one or more lipids. In some embodiments, a synthetic nanocarrier may comprise a liposome. In some embodiments, a synthetic nanocarrier may comprise a lipid bilayer. In some embodiments, a synthetic nanocarrier may comprise a lipid monolayer. In some embodiments, a synthetic nanocarrier may comprise a micelle. In some embodiments, a synthetic nanocarrier may comprise a core comprising a polymeric matrix surrounded by a lipid layer (e.g., lipid bilayer, lipid monolayer, etc.). In some embodiments, a synthetic nanocarrier may comprise a non-polymeric core (e.g., metal particle, quantum dot, ceramic particle, bone particle, viral particle, proteins, nucleic acids, carbohydrates, etc.) surrounded by a lipid layer (e.g., lipid bilayer, lipid monolayer, etc.).

In some embodiments, synthetic nanocarriers can comprise one or more polymers. In some embodiments, such a polymer can be surrounded by a coating layer (e.g., liposome, lipid monolayer, micelle, etc.). In some embodiments, various elements (i.e., components) of the synthetic nanocarriers can be coupled with the polymer.

In some embodiments, a component can be covalently associated with a polymeric matrix. In some embodiments, covalent association is mediated by a linker. In some embodiments, a component can be noncovalently associated with a polymeric matrix. For example, in some embodiments, a component can be encapsulated within, surrounded by, and/or dispersed throughout a polymeric matrix. Alternatively or additionally, a component can be associated with a polymeric matrix by hydrophobic interactions, charge interactions, van der Waals forces, etc.

A wide variety of polymers and methods for forming polymeric matrices therefrom are known conventionally. In general, a polymeric matrix comprises one or more polymers.

The synthetic nanocarriers provided herein may be polymeric nanocarriers. Polymers may be natural or unnatural (synthetic) polymers. Polymers may be homopolymers or copolymers comprising two or more monomers. In terms of sequence, copolymers may be random, block, or comprise a combination of random and block sequences. Typically, polymers in accordance with the present invention are organic polymers.

In some embodiments, the synthetic nanocarriers comprise one or more polymers that comprise a polyester, polycarbonate, polyamide, or polyether, or unit thereof. In other embodiments, the polymer comprises poly(ethylene glycol) (PEG), poly(lactic acid), poly(glycolic acid), poly(lactic-co-glycolic acid), or a polycaprolactone, or unit thereof. In some embodiments, it is preferred that the polymer is biodegradable. Therefore, in these embodiments, it is preferred that if the polymer comprises a polyether, such as poly(ethylene glycol) or unit thereof, the polymer comprises a block-co-polymer of a polyether and a biodegradable polymer such that the polymer is biodegradable. In other embodiments, the polymer does not solely comprise a polyether or unit thereof, such as poly(ethylene glycol) or unit thereof. The one or more polymers may be comprised within a polymeric synthetic nanocarrier or may be comprised in a number of other different types of synthetic nanocarriers.

Examples of polymers suitable for use in the present invention also include, but are not limited to polyethylenes, polycarbonates (e.g. poly(1,3-dioxan-2one)), polyanhydrides (e.g. poly(sebacic anhydride)), polypropylfumerates, polyamides (e.g. polycaprolactam), polyacetals, polyethers, polyesters (e.g., polylactide, polyglycolide, polylactide-co-glycolide, polycaprolactone, polyhydroxyacid (e.g. poly(β-hydroxyalkanoate))), poly(orthoesters), polycyanoacrylates, polyvinyl alcohols, polyurethanes, polyphosphazenes, polyacrylates, polymethacrylates, polyureas, polystyrenes, and polyamines, polylysine, polylysine-PEG copolymers, and poly(ethyleneimine), poly(ethylene imine)-PEG copolymers.

In some embodiments, polymers in accordance with the present invention include polymers which have been approved for use in humans by the U.S. Food and Drug Administration (FDA) under 21 C.F.R. § 177.2600, including but not limited to polyesters (e.g., polylactic acid, poly(lactic-co-glycolic acid), polycaprolactone, polyvalerolactone, poly(1,3-dioxan-2one)); polyanhydrides (e.g., poly(sebacic anhydride)); polyethers (e.g., polyethylene glycol); polyurethanes; polymethacrylates; polyacrylates; and polycyanoacrylates.

In some embodiments, polymers can be hydrophilic. For example, polymers may comprise anionic groups (e.g., phosphate group, sulphate group, carboxylate group); cationic groups (e.g., quaternary amine group); or polar groups (e.g., hydroxyl group, thiol group, amine group). In some embodiments, a synthetic nanocarrier comprising a hydrophilic polymeric matrix generates a hydrophilic environment within the synthetic nanocarrier. In some embodiments, polymers can be hydrophobic. In some embodiments, a synthetic nanocarrier comprising a hydrophobic polymeric matrix generates a hydrophobic environment within the synthetic nanocarrier. Selection of the hydrophilicity or hydrophobicity of the polymer may have an impact on the nature of materials that are incorporated (e.g. coupled) within the synthetic nanocarrier.

In some embodiments, polymers may be modified with one or more moieties and/or functional groups. A variety of moieties or functional groups can be used in accordance with the present invention. In some embodiments, polymers may be modified with polyethylene glycol (PEG), with a carbohydrate, and/or with acyclic polyacetals derived from polysaccharides (Papisov, 2001, ACS Symposium Series, 786:301). Certain embodiments may be made using the general teachings of U.S. Pat. No. 5,543,158 to Gref et al., or WO publication WO2009/051837 by Von Andrian et al.

In some embodiments, polymers may be modified with a lipid or fatty acid group. In some embodiments, a fatty acid group may be one or more of butyric, caproic, caprylic, capric, lauric, myristic, palmitic, stearic, arachidic, behenic, or lignoceric acid. In some embodiments, a fatty acid group may be one or more of palmitoleic, oleic, vaccenic, linoleic, alpha-linoleic, gamma-linoleic, arachidonic, gadoleic, arachidonic, eicosapentaenoic, docosahexaenoic, or erucic acid.

In some embodiments, polymers may be polyesters, including copolymers comprising lactic acid and glycolic acid units, such as poly(lactic acid-co-glycolic acid) and poly(lactide-co-glycolide), collectively referred to herein as "PLGA"; and homopolymers comprising glycolic acid units, referred to herein as "PGA," and lactic acid units, such as poly-L-lactic acid, poly-D-lactic acid, poly-D,L-lactic acid, poly-L-lactide, poly-D-lactide, and poly-D,L-lactide, collectively referred to herein as "PLA." In some embodiments, exemplary polyesters include, for example, polyhydroxyacids; PEG copolymers and copolymers of lactide and glycolide (e.g., PLA-PEG copolymers, PGA-PEG copolymers, PLGA-PEG copolymers, and derivatives thereof. In some embodiments, polyesters include, for example, poly(caprolactone), poly(caprolactone)-PEG copolymers, poly(L-lactide-co-L-lysine), poly(serine ester), poly(4-hydroxy-L-proline ester), poly[α-(4-aminobutyl)-L-glycolic acid], and derivatives thereof.

In some embodiments, a polymer may be PLGA. PLGA is a biocompatible and biodegradable co-polymer of lactic acid and glycolic acid, and various forms of PLGA are characterized by the ratio of lactic acid:glycolic acid. Lactic acid can be L-lactic acid, D-lactic acid, or D,L-lactic acid. The degradation rate of PLGA can be adjusted by altering the lactic acid:glycolic acid ratio. In some embodiments, PLGA to be used in accordance with the present invention is characterized by a lactic acid:glycolic acid ratio of approximately 85:15, approximately 75:25, approximately 60:40, approximately 50:50, approximately 40:60, approximately 25:75, or approximately 15:85.

In some embodiments, polymers may be one or more acrylic polymers. In certain embodiments, acrylic polymers include, for example, acrylic acid and methacrylic acid copolymers, methyl methacrylate copolymers, ethoxyethyl methacrylates, cyanoethyl methacrylate, aminoalkyl methacrylate copolymer, poly(acrylic acid), poly(methacrylic acid), methacrylic acid alkylamide copolymer, poly(methyl methacrylate), poly(methacrylic acid anhydride), methyl methacrylate, polymethacrylate, poly(methyl methacrylate) copolymer, polyacrylamide, aminoalkyl methacrylate copolymer, glycidyl methacrylate copolymers, polycyanoacrylates, and combinations comprising one or more of the foregoing polymers.

The acrylic polymer may comprise fully-polymerized copolymers of acrylic and methacrylic acid esters with a low content of quaternary ammonium groups.

In some embodiments, polymers can be cationic polymers. In general, cationic polymers are able to condense and/or protect negatively charged strands of nucleic acids (e.g. DNA, or derivatives thereof). Amine-containing polymers such as poly(lysine) (Zauner et al., 1998, Adv. Drug Del. Rev., 30:97; and Kabanov et al., 1995, Bioconjugate Chem., 6:7), poly(ethylene imine) (PEI; Boussif et al., 1995, Proc. Natl. Acad. Sci., USA, 1995, 92:7297), and poly (amidoamine) dendrimers (Kukowska-Latallo et al., 1996, Proc. Natl. Acad. Sci., USA, 93:4897; Tang et al., 1996, Bioconjugate Chem., 7:703; and Haensler et al., 1993, Bioconjugate Chem., 4:372) are positively-charged at physiological pH, form ion pairs with nucleic acids, and mediate transfection in a variety of cell lines. In embodiments, the synthetic nanocarriers may not comprise (or may exclude) cationic polymers.

In some embodiments, polymers can be degradable polyesters bearing cationic side chains (Putnam et al., 1999, Macromolecules, 32:3658; Barrera et al., 1993, J. Am. Chem. Soc., 115:11010; Kwon et al., 1989, Macromolecules, 22:3250; Lim et al., 1999, J. Am. Chem. Soc., 121:5633; and Zhou et al., 1990, Macromolecules, 23:3399). Examples of these polyesters include poly(L-lactide-co-L-lysine) (Barrera et al., 1993, J. Am. Chem. Soc., 115:11010), poly(serine ester) (Zhou et al., 1990, Macromolecules, 23:3399), poly(4-hydroxy-L-proline ester) (Putnam et al., 1999, Macromolecules, 32:3658; and Lim et al., 1999, J. Am. Chem. Soc., 121:5633), and poly(4-hydroxy-L-proline ester) (Putnam et al., 1999, Macromolecules, 32:3658; and Lim et al., 1999, J. Am. Chem. Soc., 121:5633).

The properties of these and other polymers and methods for preparing them are well known in the art (see, for example, U.S. Pat. Nos. 6,123,727; 5,804,178; 5,770,417; 5,736,372; 5,716,404; 6,095,148; 5,837,752; 5,902,599; 5,696,175; 5,514,378; 5,512,600; 5,399,665; 5,019,379; 5,010,167; 4,806,621; 4,638,045; and 4,946,929; Wang et al., 2001, J. Am. Chem. Soc., 123:9480; Lim et al., 2001, J. Am. Chem. Soc., 123:2460; Langer, 2000, Acc. Chem. Res., 33:94; Langer, 1999, J. Control. Release, 62:7; and Uhrich et al., 1999, Chem. Rev., 99:3181). More generally, a variety of methods for synthesizing certain suitable polymers are described in Concise Encyclopedia of Polymer Science and Polymeric Amines and Ammonium Salts, Ed. by Goethals, Pergamon Press, 1980; Principles of Polymerization by Odian, John Wiley & Sons, Fourth Edition, 2004; Contemporary Polymer Chemistry by Allcock et al., Prentice-Hall, 1981; Deming et al., 1997, Nature, 390:386; and in U.S. Pat. Nos. 6,506,577, 6,632,922, 6,686,446, and 6,818,732.

In some embodiments, polymers can be linear or branched polymers. In some embodiments, polymers can be dendrimers. In some embodiments, polymers can be substantially cross-linked to one another. In some embodiments, polymers can be substantially free of cross-links. In some embodiments, polymers can be used in accordance with the present invention without undergoing a cross-linking step. It is further to be understood that synthetic nanocarriers may comprise block copolymers, graft copolymers, blends, mixtures, and/or adducts of any of the foregoing and other polymers. Those skilled in the art will recognize that the polymers listed herein represent an exemplary, not comprehensive, list of polymers that can be of use in accordance with the present invention.

In some embodiments, synthetic nanocarriers may optionally comprise one or more amphiphilic entities. In some embodiments, an amphiphilic entity can promote the production of synthetic nanocarriers with increased stability, improved uniformity, or increased viscosity. In some embodiments, amphiphilic entities can be associated with the interior surface of a lipid membrane (e.g., lipid bilayer, lipid monolayer, etc.). Many amphiphilic entities known in the art are suitable for use in making synthetic nanocarriers in accordance with the present invention. Such amphiphilic entities include, but are not limited to, phosphoglycerides; phosphatidylcholines; dipalmitoyl phosphatidylcholine (DPPC); dioleylphosphatidyl ethanolamine (DOPE); dioleyloxypropyltriethylammonium (DOTMA); dioleoylphosphatidylcholine; cholesterol; cholesterol ester; diacylglycerol; diacylglycerolsuccinate; diphosphatidyl glycerol (DPPG); hexanedecanol; fatty alcohols such as polyethylene glycol (PEG); polyoxyethylene-9-lauryl ether; a surface active fatty acid, such as palmitic acid or oleic acid; fatty acids; fatty acid monoglycerides; fatty acid diglycerides; fatty acid amides; sorbitan trioleate (Span®85) glycocholate; sorbitan monolaurate (Span®20); polysorbate 20 (Tween®20); polysorbate 60 (Tween®60); polysorbate 65 (Tween®65); polysorbate 80 (Tween®80); polysorbate 85 (Tween®85); polyoxyethylene monostearate; surfactin; a poloxomer; a sorbitan fatty acid ester such as sorbitan trioleate; lecithin; lysolecithin; phosphatidylserine; phosphatidylinositol; sphingomyelin; phosphatidylethanolamine (cephalin); cardiolipin; phosphatidic acid; cerebrosides; dicetylphosphate; dipalmitoylphosphatidylglycerol; stearylamine; dodecylamine; hexadecyl-amine; acetyl palmitate; glycerol ricinoleate; hexadecyl sterate; isopropyl myristate; tyloxapol; poly(ethylene glycol)5000-phosphatidylethanolamine; poly(ethylene glycol)-400-monostearate; phospholipids; synthetic and/or natural detergents having high surfactant properties; deoxycholates; cyclodextrins; chaotropic salts; ion pairing agents; and combinations thereof. An amphiphilic entity component may be a mixture of different amphiphilic entities. Those skilled in the art will recognize that this is an exemplary, not comprehensive, list of substances with surfactant activity. Any amphiphilic entity may be used in the production of synthetic nanocarriers to be used in accordance with the present invention.

In some embodiments, synthetic nanocarriers may optionally comprise one or more carbohydrates. Carbohydrates may be natural or synthetic. A carbohydrate may be a derivatized natural carbohydrate. In certain embodiments, a carbohydrate comprises monosaccharide or disaccharide, including but not limited to glucose, fructose, galactose, ribose, lactose, sucrose, maltose, trehalose, cellbiose, mannose, xylose, arabinose, glucoronic acid, galactoronic acid, mannuronic acid, glucosamine, galatosamine, and neuramic acid. In certain embodiments, a carbohydrate is a polysaccharide, including but not limited to pullulan, cellulose, microcrystalline cellulose, hydroxypropyl methylcellulose (HPMC), hydroxycellulose (HC), methylcellulose (MC), dextran, cyclodextran, glycogen, hydroxyethylstarch, carageenan, glycon, amylose, chitosan, N,O-carboxylmethylchitosan, algin and alginic acid, starch, chitin, inulin, konjac, glucommannan, pustulan, heparin, hyaluronic acid, curdlan, and xanthan. In embodiments, the synthetic nanocarriers do not comprise (or specifically exclude) carbohydrates, such as a polysaccharide. In certain embodiments, the carbohydrate may comprise a carbohydrate derivative such as a sugar alcohol, including but not limited to mannitol, sorbitol, xylitol, erythritol, maltitol, and lactitol.

Compositions for use in the methods according to the invention comprise synthetic nanocarriers in combination with pharmaceutically acceptable excipients, such as preservatives, buffers, saline, or phosphate buffered saline. The compositions may be made using conventional pharmaceutical manufacturing and compounding techniques to arrive at useful dosage forms. In an embodiment, synthetic nanocarriers are suspended in sterile saline solution for injection together with a preservative.

In embodiments, when preparing synthetic nanocarriers as carriers for use in vaccines, methods for coupling the components to the synthetic nanocarriers may be useful. If the component is a small molecule it may be of advantage to attach the component to a polymer prior to the assembly of the synthetic nanocarriers. In embodiments, it may also be an advantage to prepare the synthetic nanocarriers with surface groups that are used to couple the component to the synthetic nanocarrier through the use of these surface groups rather than attaching the component to a polymer and then using this polymer conjugate in the construction of synthetic nanocarriers.

In certain embodiments, the coupling can be a covalent linker. In embodiments, components according to the invention can be covalently coupled to the external surface via a 1,2,3-triazole linker formed by the 1,3-dipolar cycloaddition reaction of azido groups on the surface of the nanocarrier with the component containing an alkyne group or by the 1,3-dipolar cycloaddition reaction of alkynes on the surface of the nanocarrier with components containing an azido group. Such cycloaddition reactions are preferably performed in the presence of a Cu(I) catalyst along with a suitable Cu(I)-ligand and a reducing agent to reduce Cu(II) compound to catalytic active Cu(I) compound. This Cu(I)-catalyzed azide-alkyne cycloaddition (CuAAC) can also be referred as the click reaction.

Additionally, the covalent coupling may comprise a covalent linker that comprises an amide linker, a disulfide linker, a thioether linker, a hydrazone linker, a hydrazide linker, an imine or oxime linker, an urea or thiourea linker, an amidine linker, an amine linker, and a sulfonamide linker.

An amide linker is formed via an amide bond between an amine on one component with the carboxylic acid group of a second component such as the nanocarrier. The amide bond in the linker can be made using any of the conventional amide bond forming reactions with suitably protected amino acids or antigens or adjuvants and activated carboxylic acid such N-hydroxysuccinimide-activated ester.

A disulfide linker is made via the formation of a disulfide (S—S) bond between two sulfur atoms of the form, for instance, of R1-S—S-R2. A disulfide bond can be formed by thiol exchange of an antigen or adjuvant containing thiol/mercaptan group (—SH) with another activated thiol group on a polymer or nanocarrier or a nanocarrier containing thiol/mercaptan groups with a component containing activated thiol group.

A triazole linker, specifically a 1,2,3-triazole of the form

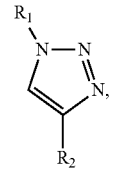

wherein R1 and R2 may be any chemical entities, is made by the 1,3-dipolar cycloaddition reaction of an azide attached to a first component such as the nanocarrier with a terminal alkyne attached to a second component. The 1,3-dipolar cycloaddition reaction is performed with or without a catalyst, preferably with Cu(I)-catalyst, which links the two components through a 1,2,3-triazole function. This chemistry is described in detail by Sharpless et al., Angew. Chem. Int. Ed. 41(14), 2596, (2002) and Meldal, et al, Chem. Rev., 2008, 108(8), 2952-3015 and is often referred to as a "click" reaction or CuAAC.

In embodiments, a polymer containing an azide or alkyne group, terminal to the polymer chain is prepared. This polymer is then used to prepare a synthetic nanocarrier in such a manner that a plurality of the alkyne or azide groups are positioned on the surface of that nanocarrier. Alternatively, the synthetic nanocarrier can be prepared by another route, and subsequently functionalized with alkyne or azide groups. The component is prepared with the presence of either an alkyne (if the polymer contains an azide) or an azide (if the polymer contains an alkyne) group. The component is then allowed to react with the nanocarrier via the 1,3-dipolar cycloaddition reaction with or without a catalyst which covalently couples the component to the particle through the 1,4-disubstituted 1,2,3-triazole linker.

A thioether linker is made by the formation of a sulfur-carbon (thioether) bond in the form, for instance, of R1-S-R2. Thioether can be made by either alkylation of a thiol/mercaptan (—SH) group on one component with an alkylating group such as halide or epoxide on a second component such as the nanocarrier. Thioether linkers can also be formed by Michael addition of a thiol/mercaptan group on one component to an electron-deficient alkene group on a second component such as a polymer containing a maleimide group or vinyl sulfone group as the Michael acceptor. In another way, thioether linkers can be prepared by the radical thiol-ene reaction of a thiol/mercaptan group on one component with an alkene group on a second component such as a polymer or nanocarrier.

A hydrazone linker is made by the reaction of a hydrazide group on one component with an aldehyde/ketone group on the second component such as the nanocarrier.

A hydrazide linker is formed by the reaction of a hydrazine group on one component with a carboxylic acid group on the second component such as the nanocarrier. Such reaction is generally performed using chemistry similar to the formation of amide bond where the carboxylic acid is activated with an activating reagent.

An imine or oxime linker is formed by the reaction of an amine or N-alkoxyamine (or aminooxy) group on one component with an aldehyde or ketone group on the second component such as the nanocarrier.

An urea or thiourea linker is prepared by the reaction of an amine group on one component with an isocyanate or thioisocyanate group on the second component such as the nanocarrier.

An amidine linker is prepared by the reaction of an amine group on one component with an imidoester group on the second component such as the nanocarrier.

An amine linker is made by the alkylation reaction of an amine group on one component with an alkylating group such as halide, epoxide, or sulfonate ester group on the second component such as the nanocarrier. Alternatively, an amine linker can also be made by reductive amination of an amine group on one component with an aldehyde or ketone group on the second component such as the nanocarrier with a suitable reducing reagent such as sodium cyanoborohydride or sodium triacetoxyborohydride.

A sulfonamide linker is made by the reaction of an amine group on one component with a sulfonyl halide (such as sulfonyl chloride) group on the second component such as the nanocarrier.

A sulfone linker is made by Michael addition of a nucleophile to a vinyl sulfone. Either the vinyl sulfone or the nucleophile may be on the surface of the nanocarrier or attached to a component.

The component can also be conjugated to the nanocarrier via non-covalent conjugation methods. For examples, a negative charged component can be conjugated to a positive charged nanocarrier through electrostatic adsorption. A component containing a metal ligand can also be conjugated to a nanocarrier containing a metal complex via a metal-ligand complex.

In embodiments, the component can be attached to a polymer, for example polylactic acid-block-polyethylene glycol, prior to the assembly of the synthetic nanocarrier or the synthetic nanocarrier can be formed with reactive or activatable groups on its surface. In the latter case, the component may be prepared with a group which is compatible with the attachment chemistry that is presented by the synthetic nanocarriers' surface. In other embodiments, a component can be attached to VLPs or liposomes using a suitable linker. A linker is a compound or reagent that capable of coupling two molecules together. In an embodiment, the linker can be a homobifuntional or heterobifunctional reagent as described in Hermanson 2008. For example, an VLP or liposome synthetic nanocarrier containing a carboxylic group on the surface can be treated with a homobifunctional linker, adipic dihydrazide (ADH), in the presence of EDC to form the corresponding synthetic nanocarrier with the ADH linker. The resulting ADH linked synthetic nanocarrier is then conjugated with a component containing an acid group via the other end of the ADH linker on NC to produce the corresponding VLP or liposome peptide conjugate.

For detailed descriptions of available conjugation methods, see Hermanson G T "Bioconjugate Techniques", 2nd Edition Published by Academic Press, Inc., 2008. In addition to covalent attachment the component can be coupled by adsorption to a pre-formed synthetic nanocarrier or it can be coupled by encapsulation during the formation of the synthetic nanocarrier.

In some embodiments, a component, such as an antigen or adjuvant, may be isolated. Isolated refers to the element being separated from its native environment and present in sufficient quantities to permit its identification or use. This means, for example, the element may be (i) selectively produced by expression cloning or (ii) purified as by chromatography or electrophoresis. Isolated elements may be, but need not be, substantially pure. Because an isolated element may be admixed with a pharmaceutically acceptable excipient in a pharmaceutical preparation, the element may comprise only a small percentage by weight of the preparation. The element is nonetheless isolated in that it has been separated from the substances with which it may be associated in living systems, i.e., isolated from other lipids or proteins. Any of the elements provided herein may be isolated. Any of the antigens provided herein can be included in the compositions in isolated form.

D. Methods of Using and Making Synthetic Nanocarrier Compositions

Synthetic nanocarriers may be prepared using a wide variety of methods known in the art. For example, synthetic nanocarriers can be formed by methods as nanoprecipitation, flow focusing fluidic channels, spray drying, single and double emulsion solvent evaporation, solvent extraction, phase separation, milling, microemulsion procedures, microfabrication, nanofabrication, sacrificial layers, simple and complex coacervation, and other methods well known to those of ordinary skill in the art. Alternatively or additionally, aqueous and organic solvent syntheses for monodisperse semiconductor, conductive, magnetic, organic, and other nanomaterials have been described (Pellegrino et al., 2005, Small, 1:48; Murray et al., 2000, Ann. Rev. Mat. Sci., 30:545; and Trindade et al., 2001, Chem. Mat., 13:3843). Additional methods have been described in the literature (see, e.g., Doubrow, Ed., "Microcapsules and Nanoparticles in Medicine and Pharmacy," CRC Press, Boca Raton, 1992;

Mathiowitz et al., 1987, J. Control. Release, 5:13; Mathiowitz et al., 1987, Reactive Polymers, 6: 275; and Mathiowitz et al., 1988, J. Appl. Polymer Sci., 35:755; U.S. Pat. Nos. 5,578,325 and 6,007,845; P. Paolicelli et al., "Surface-modified PLGA-based Nanoparticles that can Efficiently Associate and Deliver Virus-like Particles" Nanomedicine. 5(6):843-853 (2010)).

Various materials may be encapsulated into synthetic nanocarriers as desirable using a variety of methods including but not limited to C. Astete et al., "Synthesis and characterization of PLGA nanoparticles" J. Biomater. Sci. Polymer Edn, Vol. 17, No. 3, pp. 247-289 (2006); K. Avgoustakis "Pegylated Poly(Lactide) and Poly(Lactide-Co-Glycolide) Nanoparticles: Preparation, Properties and Possible Applications in Drug Delivery" Current Drug Delivery 1:321-333 (2004); C. Reis et al., "Nanoencapsulation I. Methods for preparation of drug-loaded polymeric nanoparticles" Nanomedicine 2:8-21 (2006); P. Paolicelli et al., "Surface-modified PLGA-based Nanoparticles that can Efficiently Associate and Deliver Virus-like Particles" Nanomedicine. 5(6):843-853 (2010). Other methods suitable for encapsulating materials into synthetic nanocarriers may be used, including without limitation methods disclosed in U.S. Pat. No. 6,632,671 to Unger Oct. 14, 2003.

In certain embodiments, synthetic nanocarriers are prepared by a nanoprecipitation process or spray drying. Conditions used in preparing synthetic nanocarriers may be altered to yield particles of a desired size or property (e.g., hydrophobicity, hydrophilicity, external morphology, "stickiness," shape, etc.). The method of preparing the synthetic nanocarriers and the conditions (e.g., solvent, temperature, concentration, air flow rate, etc.) used may depend on the materials to be coupled to the synthetic nanocarriers and/or the composition of the polymer matrix.

If particles prepared by any of the above methods have a size range outside of the desired range, particles can be sized, for example, using a sieve.

Elements of the synthetic nanocarriers may be coupled to the overall synthetic nanocarrier, e.g., by one or more covalent bonds, or may be coupled by means of one or more linkers. Additional methods of functionalizing synthetic nanocarriers may be adapted from Published US Patent Application 2006/0002852 to Saltzman et al., Published US Patent Application 2009/0028910 to DeSimone et al., or Published International Patent Application WO/2008/127532 A1 to Murthy et al.

Alternatively or additionally, synthetic nanocarriers can be coupled to elements directly or indirectly via non-covalent interactions. In non-covalent embodiments, the non-covalent coupling is mediated by non-covalent interactions including but not limited to charge interactions, affinity interactions, metal coordination, physical adsorption, host-guest interactions, hydrophobic interactions, TT stacking interactions, hydrogen bonding interactions, van der Waals interactions, magnetic interactions, electrostatic interactions, dipole-dipole interactions, and/or combinations thereof. Such couplings may be arranged to be on an external surface or an internal surface of an synthetic nanocarrier. In embodiments, encapsulation and/or absorption is a form of coupling.

In embodiments, the synthetic nanocarriers can be combined with adjuvants by admixing in the same vehicle or delivery system. Such adjuvants may include, but are not limited to mineral salts, such as alum, alum combined with monphosphoryl lipid (MPL) A of Enterobacteria, such as Escherihia coli, Salmonella minnesota, Salmonella typhimurium, or Shigella flexneri or specifically with MPL® (AS04), MPL A of above-mentioned bacteria separately, saponins, such as QS-21, Quil-A, ISCOMs, ISCOMATRIX™, emulsions such as MF59™, Montanide® ISA 51 and ISA 720, AS02 (QS21+squalene+MPL®), liposomes and liposomal formulations such as AS01, synthesized or specifically prepared microparticles and microcarriers such as bacteria-derived outer membrane vesicles (OMV) of N. gonorrheae, Chlamydia trachomatis and others, or chitosan particles, depot-forming agents, such as Pluronic® block co-polymers, specifically modified or prepared peptides, such as muramyl dipeptide, aminoalkyl glucosaminide 4-phosphates, such as RC529, or proteins, such as bacterial toxoids or toxin fragments. The doses of such other adjuvants can be determined using conventional dose ranging studies.

In embodiments, the synthetic nanocarriers can be combined with an antigen different, similar or identical to those coupled to a nanocarrier (with or without adjuvant, utilizing or not utilizing another delivery vehicle) administered separately at a different time-point and/or at a different body location and/or by a different immunization route or with another antigen and/or adjuvant-carrying synthetic nanocarrier administered separately at a different time-point and/or at a different body location and/or by a different immunization route.

Populations of synthetic nanocarriers may be combined to form pharmaceutical dosage forms according to the present invention using traditional pharmaceutical mixing methods. These include liquid-liquid mixing in which two or more suspensions, each containing one or more subsets of nanocarriers, are directly combined or are brought together via one or more vessels containing diluent. As synthetic nanocarriers may also be produced or stored in a powder form, dry powder-powder mixing could be performed as could the re-suspension of two or more powders in a common media. Depending on the properties of the nanocarriers and their interaction potentials, there may be advantages conferred to one or another route of mixing.

Typical compositions that comprise synthetic nanocarriers may comprise inorganic or organic buffers (e.g., sodium or potassium salts of phosphate, carbonate, acetate, or citrate) and pH adjustment agents (e.g., hydrochloric acid, sodium or potassium hydroxide, salts of citrate or acetate, amino acids and their salts) antioxidants (e.g., ascorbic acid, alpha-tocopherol), surfactants (e.g., polysorbate 20, polysorbate 80, polyoxyethylene9-10 nonyl phenol, sodium desoxycholate), solution and/or cryo/lyo stabilizers (e.g., sucrose, lactose, mannitol, trehalose), osmotic adjustment agents (e.g., salts or sugars), antibacterial agents (e.g., benzoic acid, phenol, gentamicin), antifoaming agents (e.g., polydimethylsilozone), preservatives (e.g., thimerosal, 2-phenoxyethanol, EDTA), polymeric stabilizers and viscosity-adjustment agents (e.g., polyvinylpyrrolidone, poloxamer 488, carboxymethylcellulose) and co-solvents (e.g., glycerol, polyethylene glycol, ethanol).

Compositions according to the invention comprise synthetic nanocarriers in combination with pharmaceutically acceptable excipients. The compositions may be made using conventional pharmaceutical manufacturing and compounding techniques to arrive at useful dosage forms. Techniques suitable for use in practicing the present invention may be found in Handbook of Industrial Mixing: Science and Practice, Edited by Edward L. Paul, Victor A. Atiemo-Obeng, and Suzanne M. Kresta, 2004 John Wiley & Sons, Inc.; and Pharmaceutics: The Science of Dosage Form Design, 2nd Ed. Edited by M. E. Auten, 2001, Churchill Livingstone. In an embodiment, synthetic nanocarriers are suspended in sterile saline solution for injection together with a preservative.

It is to be understood that the compositions of synthetic nanocarriers can be made in any suitable manner, and the invention is in no way limited to the use of compositions that can be produced using the methods described herein. Selection of an appropriate method may require attention to the properties of the particular elements being associated.

In some embodiments, synthetic nanocarriers are manufactured under sterile conditions or are terminally sterilized. This can ensure that resulting composition are sterile and non-infectious, thus improving safety when compared to non-sterile compositions. This provides a valuable safety measure, especially when subjects receiving synthetic nanocarriers have immune defects, are suffering from infection, and/or are susceptible to infection. In some embodiments, synthetic nanocarriers may be lyophilized and stored in suspension or as lyophilized powder depending on the formulation strategy for extended periods without losing activity.

The compositions of the invention can be administered by a variety of routes, including or not limited to subcutaneous, intranasal, oral, intravenous, intraperitoneal, intramuscular, transmucosal, transmucosal, sublingual, rectal, ophthalmic, pulmonary, intradermal, transdermal, transcutaneous or intradermal or by a combination of these routes. Routes of administration also include administration by inhalation or pulmonary aerosol. Techniques for preparing aerosol delivery systems are well known to those of skill in the art (see, for example, Sciarra and Cutie, "Aerosols," in *Remington's Pharmaceutical Sciences,* 18th edition, 1990, pp. 1694-1712; incorporated by reference).

Doses of dosage forms contain varying amounts of populations of synthetic nanocarriers and varying amounts of the proteins and/or adjuvants and/or additional antigens, according to the invention. The amount of synthetic nanocarriers and/or proteins and/or adjuvants and/or additional antigens present in the dosage forms can be varied according to the nature of the elements present, the therapeutic benefit to be accomplished, and other such parameters. In embodiments, dose ranging studies can be conducted to establish optimal therapeutic amount of the population of synthetic nanocarriers and the amount of proteins and/or adjuvants and/or additional antigens to be present in the dosage form. In embodiments, the synthetic nanocarriers and the proteins and/or adjuvants and/or additional antigens are present in the dosage form in an amount effective to generate an immune response to the proteins and/or additional antigens upon administration to a subject. It may be possible to determine amounts effective to generate an immune response using conventional dose ranging studies and techniques in subjects. Dosage forms may be administered at a variety of frequencies. In a preferred embodiment, at least one administration of the dosage form is sufficient to generate a pharmacologically relevant response. In more preferred embodiment, at least two administrations, at least three administrations, or at least four administrations, of the dosage form are utilized to ensure a pharmacologically relevant response.

The compositions and methods described herein can be used to induce, enhance, suppress, modulate, direct, or redirect an immune response. The compositions and methods described herein can be used in the diagnosis, prophylaxis and/or treatment of conditions such as cancers, infectious diseases, metabolic diseases, degenerative diseases, non-autoimmune diseases, HIV, malaria, hepatitis B or any of the other disorders and/or conditions provided herein.

Examples of infectious disease include, but are not limited to, viral infectious diseases, such as AIDS, Chickenpox (Varicella), Common cold, Cytomegalovirus Infection, Colorado tick fever, Dengue fever, Ebola hemorrhagic fever, Hand, foot and mouth disease, Hepatitis, Herpes simplex, Herpes zoster, HPV, Influenza (Flu), Lassa fever, Measles, Marburg hemorrhagic fever, Infectious mononucleosis, Mumps, Norovirus, Poliomyelitis, Progressive multifocal leukencephalopathy, Rabies, Rubella, SARS, Smallpox (Variola), Viral encephalitis, Viral gastroenteritis, Viral meningitis, Viral pneumonia, West Nile disease and Yellow fever; bacterial infectious diseases, such as Anthrax, Bacterial Meningitis, Botulism, Brucellosis, Campylobacteriosis, Cat Scratch Disease, Cholera, Diphtheria, Epidemic Typhus, Gonorrhea, Impetigo, Legionellosis, Leprosy (Hansen's Disease), Leptospirosis, Listeriosis, Lyme disease, Melioidosis, Rheumatic Fever, MRSA infection, Nocardiosis, Pertussis (Whooping Cough), Plague, Pneumococcal pneumonia, Psittacosis, Q fever, Rocky Mountain Spotted Fever (RMSF), Salmonellosis, Scarlet Fever, Shigellosis, Syphilis, Tetanus, Trachoma, Tuberculosis, Tularemia, Typhoid Fever, Typhus and Urinary Tract Infections; parasitic infectious diseases, such as African trypanosomiasis, Amebiasis, *Ascariasis*, Babesiosis, Chagas Disease, Clonorchiasis, Cryptosporidiosis, Cysticercosis, Diphyllobothriasis, Dracunculiasis, Echinococcosis, Enterobiasis, Fascioliasis, Fasciolopsiasis, Filariasis, Free-living amebic infection, Giardiasis, Gnathostomiasis, Hymenolepiasis, Isosporiasis, Kala-azar, Leishmaniasis, Malaria, Metagonimiasis, Myiasis, Onchocerciasis, Pediculosis, Pinworm Infection, Scabies, Schistosomiasis, Taeniasis, Toxocariasis, Toxoplasmosis, Trichinellosis, Trichinosis, Trichuriasis, Trichomoniasis and Trypanosomiasis; fungal infectious disease, such as Aspergillosis, Blastomycosis, Candidiasis, Coccidioidomycosis, Cryptococcosis, Histoplasmosis, Tinea pedis (Athlete's Foot) and Tinea cruris; prion infectious diseases, such as Alpers' disease, Fatal Familial Insomnia, Gerstmann-Straiussler-Scheinker syndrome, Kuru and Variant Creutzfeldt-Jakob disease.

Examples of cancers include, but are not limited to breast cancer; biliary tract cancer; bladder cancer; brain cancer including glioblastomas and medulloblastomas; cervical cancer; choriocarcinoma; colon cancer; endometrial cancer; esophageal cancer; gastric cancer; hematological neoplasms including acute lymphocytic and myelogenous leukemia, e.g., B Cell CLL; T-cell acute lymphoblastic leukemia/lymphoma; hairy cell leukemia; chronic myelogenous leukemia, multiple myeloma; AIDS-associated leukemias and adult T-cell leukemia/lymphoma; intraepithelial neoplasms including Bowen's disease and Paget's disease; liver cancer; lung cancer; lymphomas including Hodgkin's disease and lymphocytic lymphomas; neuroblastomas; oral cancer including squamous cell carcinoma; ovarian cancer including those arising from epithelial cells, stromal cells, germ cells and mesenchymal cells; pancreatic cancer; prostate cancer; rectal cancer; sarcomas including leiomyosarcoma, rhabdomyosarcoma, liposarcoma, fibrosarcoma, and osteosarcoma; skin cancer including melanoma, Merkel cell carcinoma, Kaposi's sarcoma, basal cell carcinoma, and squamous cell cancer; testicular cancer including germinal tumors such as seminoma, non-seminoma (teratomas, choriocarcinomas), stromal tumors, and germ cell tumors; thyroid cancer including thyroid adenocarcinoma and medullar carcinoma; and renal cancer including adenocarcinoma and Wilms tumor.

Examples of metabolic diseases include, but are not limited to, disorders of carbohydrate metabolism, amino acid metabolism, organic acid metabolism, fatty acid oxidation and mitochondrial metabolism, prophyrin metabolism, purine or pyrimidine metabolism, steroid metabolism, lysosomal mitochondrial function, peroxisomal function, lysosomal storage, urea cycle disorders (e.g., N-acetyl glutamate synthetase deficiency, carbamylphosphate synthase deficiency, ornithine carbamyl transferase deficiency, crginosuccinic aciduria, citrullinaemia, arginase deficiency), amino acid disorders (e.g., Non-ketotic hyperglycinaemia, tyrosinaemia (Type I), Maple syrup urine disease), organic acidemias (e.g. isovaleric acidemia, methylmalonic acidemia, propionic acidemia, glutaric aciduria type I, glutaric acidemia type I & II), mitochondrial disorders (e.g., carboxylase defects, mitochondrial myopathies, lactic acidosis (pyruvate dehydrogenase complex defects), congenital lactic acidosis, mitochondrial respiratory chain defects, cystinosis, Gaucher's disease, Fabry's disease, Pompe's disease, mucopolysaccharoidosis I, mucopolysaccharoidosis II, mucopolysaccharoidosis VI).

Examples of degenerative diseases include, but are not limited to, mesenchyme/mesoderm degenerative disease, muscle degenerative disease, endothelial degenerative disease, neurodegenerative disease, degenerative joint disease (e.g., osteoarthritis), major types of degenerative heart disease (e.g., coronary heart disease, congenital heart disease, rheumatic heart disease, angina pectoris), neurodegenerative disease (e.g., Alzheimer's disease, amyotrophic lateral sclerosis, Friedreich's ataxia, Huntington's disease, Lewy body disease, Parkinson's disease, spinal muscular atrophy), neuromuscular disorders (e.g., muscular dystrophy, duchenne muscular dystrophy, facioscapulohumeral muscular dystrophy, myotonic muscular dystrophy, congenital myopathy, familial cardiomyopathy, dilated cardiomyopathy, hypertrophic cardiomyopathy, restrictive cardiomyopathy, or coronary artery disease).

The proteins for coupling to the synthetic nanocarriers and/or the additional antigens provided herein can be antigens associated with any of the diseases or conditions provided herein. These include antigens associated with cancer, infections or infectious disease or degenerative or non-autoimmune disease. Antigens associated with HIV, malaria, leischmaniasis, a human filovirus infection, a togavirus infection, a alphavirus infection, an arenavirus infection, a bunyavirus infection, a flavivirus infection, a human papillomavirus infection, a human influenza A virus infection, a hepatitis B infection or a hepatitis C infection are also included.

Examples of cancer antigens include HER 2 (p185), CD20, CD33, GD3 ganglioside, GD2 ganglioside, carcinoembryonic antigen (CEA), CD22, milk mucin core protein, TAG-72, Lewis A antigen, ovarian associated antigens such as OV-TL3 and MOv18, high Mr melanoma antigens recognized by antibody 9.2.27, HMFG-2, SM-3, B72.3, PR5C5, PR4D2, and the like. Further examples include MAGE, MART-1/Melan-A, gp100, Dipeptidyl peptidase IV (DPPIV), adenosine deaminase-binding protein (ADAbp), FAP, cyclophilin b, Colorectal associated antigen (CRC)-C017-1A/GA733, Carcinoembryonic Antigen (CEA) and its immunogenic epitopes CAP-1 and CAP-2, etv6, aml1, prostatic acid phosphatase (PAP), Prostate Specific Antigen (PSA) and its immunogenic epitopes PSA-1, PSA-2, and PSA-3, prostate-specific membrane antigen (PSMA), T-cell receptor/CD3-zeta chain, MAGE-family of tumor antigens (e.g., MAGE-I or MAGE-II families) (e.g., MAGE-A1, MAGE-A2, MAGE-A3, MAGE-A4, MAGE-A5, MAGE-A6, MAGE-A7, MAGE-A8, MAGE-A9, MAGE-A10, MAGE-A11, MAGE-A12, MAGE-Xp2 (MAGE-B2), MAGE-Xp3 (MAGE-B3), MAGE-Xp4 (MAGE-B4), MAGE-C1, MAGE-C2, MAGE-C3, MAGE-C4, MAGE-C5), GAGE-family of tumor antigens (e.g., GAGE-1, GAGE-2, GAGE-3, GAGE-4, GAGE-5, GAGE-6, GAGE-7, GAGE-8, GAGE-9), BAGE, RAGE, LAGE-1, NAG, GnT-V, MUM-1, CDK4, tyrosinase, p53, MUC family, HER2/neu, p21ras, RCAS1, α-fetoprotein, E-cadherin, α-catenin, β-catenin and γ-catenin, p120ctn, gp100Pme1117, PRAME, NY-ESO-1, cdc27, adenomatous polyposis coli protein (APC), fodrin, Connexin 37, Ig-idiotype, p15, gp75, GM2 and GD2 gangliosides, viral products such as human papilloma virus proteins, Smad family of tumor antigens, Imp-1, P1A, EBV-encoded nuclear antigen (EBNA)-1, brain glycogen phosphorylase, SSX-1, SSX-2 (HOM-MEL-40), SSX-1, SSX-4, SSX-5, SCP-1 and CT-7, CD20 and c-erbB-2.

In another embodiment, antigens associated with infection or infectious disease are associated with any of the infectious agents provided herein. In one embodiment, the infectious agent is a virus of the Adenoviridae, Picornaviridae, Herpesviridae, Hepadnaviridae, Flaviviridae, Retroviridae, Orthomyxoviridae, Paramyxoviridae, Papillomaviridae, Rhabdoviridae, Togaviridae or Paroviridae family. In still another embodiment, the infectious agent is adenovirus, coxsackievirus, hepatitis A virus, poliovirus, Rhinovirus, Herpes simplex virus, Varicella-zoster virus, Epstein-barr virus, Human cytomegalovirus, Human herpesvirus, Hepatitis B virus, Hepatitis C virus, yellow fever virus, dengue virus, West Nile virus, HIV, Influenza virus, Measles virus, Mumps virus, Parainfluenza virus, Respiratory syncytial virus, Human metapneumovirus, Human papillomavirus, Rabies virus, Rubella virus, Human bocarivus or Parvovirus B 19. In yet another embodiment, the infectious agent is a bacteria of the *Bordetella, Borrelia, Brucella, Campylobacter, Chlamydia* and *Chlamydophila, Clostridium, Corynebacterium, Enterococcus, Escherichia, Francisella, Haemophilus, Helicobacter, Legionella, Leptospira, Listeria, Mycobacterium, Mycoplasma, Neisseria, Pseudomonas, Rickettsia, Salmonella, Shigella, Staphylococcus, Streptococcus, Treponema Vibrio* or *Yersinia* genus. In a further embodiment, the infectious agent is *Bordetella pertussis, Borrelia burgdorferi, Brucella abortus, Brucella canis, Brucella melitensis, Brucella suis, Campylobacter jejuni, Chlamydia pneumoniae, Chlamydia trachomatis, Chlamydophila psittaci, Clostridium botulinum, Clostridium difficile, Clostridium perfringens, Clostridium tetani, Corynebacterium diphtheriae, Enterococcus faecalis, Enterococcus faecium, Escherichia coli, Francisella tularensis, Haemophilus influenzae, Helicobacter pylori, Legionella pneumophila, Leptospira interrogans, Listeria monocytogenes, Mycobacterium leprae, Mycobacterium tuberculosis, Mycobacterium ulcerans, Mycoplasma pneumoniae, Neisseria gonorrhoeae, Neisseria meningitides, Pseudomonas aeruginosa, Rickettsia rickettsii, Salmonella typhi, Salmonella typhimurium, Shigella sonnei, Staphylococcus aureus, Staphylococcus epidermidis, Staphylococcus saprophyticus, Streptococcus agalactiae, Streptococcus pneumoniae, Streptococcus pyogenes, Treponema pallidum, Vibrio cholerae* or *Yersinia pestis*. In another embodiment, the infectious agent is a fungus of the *Candida, Aspergillus, Cryptococcus, Histoplasma, Pneumocystis* or *Stachybotrys* genus. In still another embodiment, the infectious agent is *C. albicans, Aspergillus fumigatus, Aspergillus flavus, Cryptococcus neoformans,*

*Cryptococcus laurentii, Cryptococcus albidus, Cryptococcus gattii, Histoplasma capsulatum, Pneumocystis jirovecii* or *Stachybotrys chartarum*.

In yet another embodiment, the antigen associated with infection or infectious disease is one that comprises VI, VII, E1A, E3-19K, 52K, VP1, surface antigen, 3A protein, capsid protein, nucleocapsid, surface projection, transmembrane proteins, UL6, UL18, UL35, UL38, UL19, early antigen, capsid antigen, Pp65, gB, p52, latent nuclear antigen-1, NS3, envelope protein, envelope protein E2 domain, gp120, p24, lipopeptides Gag (17-35), Gag (253-284), Nef (66-97), Nef (116-145), Pol (325-355), neuraminidase, nucleocapsid protein, matrix protein, phosphoprotein, fusion protein, hemagglutinin, hemagglutinin-neuraminidase, glycoprotein, E6, E7, envelope lipoprotein or non-structural protein (NS). In another embodiment, the antigen comprises pertussis toxin (PT), filamentous hemagglutinin (FHA), pertactin (PRN), fimbriae (FIM 2/3), VlsE; DbpA, OspA, Hia, PrpA, MltA, L7/L12, D15, 0187, VirJ, Mdh, AfuA, L7/L12, out membrane protein, LPS, antigen type A, antigen type B, antigen type C, antigen type D, antigen type E, FliC, FliD, Cwp84, alpha-toxin, theta-toxin, fructose 1,6-biphosphate-aldolase (FBA), glyceraldehydes-3-phosphate dehydrogenase (GPD), pyruvate:ferredoxin oxidoreductase (PFOR), elongation factor-G (EF-G), hypothetical protein (HP), T toxin, Toxoid antigen, capsular polysaccharide, Protein D, Mip, nucleoprotein (NP), RD1, PE35, PPE68, EsxA, EsxB, RD9, EsxV, Hsp70, lipopolysaccharide, surface antigen, Sp1, Sp2, Sp3, Glycerophosphodiester Phosphodiesterase, outer membrane protein, chaperone-usher protein, capsular protein (F1) or V protein. In yet another embodiment, the antigen is one that comprises capsular glycoprotein, Yps3P, Hsp60, Major surface protein, MsgC1, MsgC3, MsgC8, MsgC9 or SchS34.

EXAMPLES

Example 1

Synthetic Nanocarrier Formulation Lot #1

Materials

Ovalbumin protein, was purchased from Worthington Biochemical Corporation (730 Vassar Avenue, Lakewood, N.J. 08701. Product Code 3048.) PLGA-R848 of approximately 5,200 Da made from PLGA of 3:1 lactide to glycolide ratio and having 12.7% w/w conjugated R848 content was synthesized. PLA-PEG-Nicotine with a nicotine-terminated PEG block of approximately 5,000 Da and DL-PLA block of approximately 19,000 Da was synthesized. PLA with an inherent viscosity of 0.21 dL/g was purchased from SurModics Pharmaceuticals (756 Tom Martin Drive, Birmingham, Ala. 35211. Product Code 100 DL 2A.) Polyvinyl alcohol (Mw=11,000-31,000, 87-89% hydrolyzed) was purchased from J. T. Baker (Part Number U232-08).

Method

Solutions were prepared as follows:

Solution 1: Ovalbumin protein at 20 mg/mL in 10 mM phosphate buffer.

Solution 2: PLGA-R848 at 50 mg/mL, PLA-PEG-Nicotine at 25 mg/mL, PLA at 25 mg/ml in dichloromethane. The solution was prepared by separately dissolving each polymer as a 100 mg/mL in dichloromethane, then mixing the solutions by adding 2 parts PLGA-R848 solution to 1 part each PLA-PEG-Nicotine solution and PLA solution.

Solution 3: Polyvinyl alcohol 50 mg/mL in 100 mM in 100 mM phosphate buffer, pH 8.

Solution 4: 70 mM phosphate buffer, pH 8.

A primary (W1/O) emulsion was first created using Solution 1 & Solution 2. Solution 1 (0.2 mL) and Solution 2 (1.0 mL) were combined in a small glass pressure tube and sonicated at 50% amplitude for 40 seconds using a Branson Digital Sonifier 250. A secondary (W1/O/W2) emulsion was then formed by adding Solution 3 (2.0 mL) to the primary emulsion, and then sonicating at 30% amplitude for 40 seconds using the Branson Digital Sonifier 250. The secondary emulsion was added to an open 50 mL beaker containing 70 mM phosphate buffer solution (30 mL) and stirred at room temperature for 2 hours to allow the dichloromethane to evaporate and the nanocarriers to form in suspension. A portion of the suspended nanocarriers was washed by transferring the nanocarrier suspension to a centrifuge tube, spinning at 13,823 g for one hour, removing the supernatant, and re-suspending the pellet in phosphate buffered saline. This washing procedure was repeated and then the pellet was re-suspended in phosphate buffered saline to achieve a nanocarrier suspension having a nominal concentration of 10 mg/mL on a polymer basis. The suspension was stored frozen at −20° C. until use.

TABLE 1

| Nanocarrier Characterization | | | |
|---|---|---|---|
| Nanocarrier ID | Effective Diameter (nm) | R848 (% w/w) | Ovalbumin (% w/w) |
| 1 | 214 | 4.0 | 1.1 |

Example 2

Synthetic Nanocarrier Formulation Lot #2

Materials

Ovalbumin protein, was purchased from Worthington Biochemical Corporation (730 Vassar Avenue, Lakewood, N.J. 08701. Product Code 3048.) Ovalbumin peptide 323-339 amide acetate salt, was purchased from Bachem Americas Inc. (3132 Kashiwa Street, Torrance Calif. 90505. Product code 4065609.) PLGA-R848 of approximately 5,200 Da made from PLGA of 3:1 lactide to glycolide ratio and having 12.7% w/w conjugated R848 content was synthesized. PLA-PEG-Nicotine with a nicotine-terminated PEG block of approximately 5,000 Da and DL-PLA block of approximately 19,000 Da was synthesized. PLA with an inherent viscosity of 0.21 dL/g was purchased from SurModics Pharmaceuticals (756 Tom Martin Drive, Birmingham, Ala. 35211. Product Code 100 DL 2A.) Polyvinyl alcohol (Mw=11,000-31,000, 87-89% hydrolyzed) was purchased from J. T. Baker (Part Number U232-08).

Method

Solutions were prepared as follows:

Solution 1A: Ovalbumin protein at 40 mg/mL in 10 mM phosphate buffer.

Solution 1B: Ovalbumin peptide amide 323-339 @ 40 mg/mL in dilute hydrochloric acid aqueous solution.

Solution 2: PLGA-R848 at 50 mg/mL, PLA-PEG-Nicotine at 25 mg/mL, PLA at 25 mg/ml in dichloromethane. The solution was prepared by separately dissolving each polymer at 100 mg/mL in dichloromethane, then mixing the solutions by adding 2 parts PLGA-R848 solution to 1 part each PLA-PEG-Nicotine solution and PLA solution.

Solution 3: Polyvinyl alcohol @ 50 mg/mL in 100 mM in 100 mM phosphate buffer, pH 8.

Solution 4: 70 mM phosphate buffer, pH 8.

The first primary (W1/O) emulsion was created using Solution 1A & Solution 2. Solution 1A (0.2 mL) and Solution 2 (1.0 mL) were combined in a small glass pressure tube and sonicated at 50% amplitude for 40 seconds using a Branson Digital Sonifier 250. A second primary (W1/O) emulsion was created using Solution 1B & Solution 2. Solution 1B (0.2 mL) and Solution 2 (1.0 mL) were combined in a small glass pressure tube and sonicated at 50% amplitude for 40 seconds using a Branson Digital Sonifier 250. Approximately ½ of the second primary emulsion was removed from its pressure tube and discarded and then ½ of the first primary emulsion (0.500 mL), was added to the tube to create a 1:1 mixture of the two primary emulsions in a total volume of approximately 1 mL. A secondary (W1/O/W2) emulsion was then formed by adding Solution 3 (2.0 mL) to the primary emulsion, and then sonicating at 30% amplitude for 40 seconds using the Branson Digital Sonifier 250. The secondary emulsion was added to an open 50 mL beaker containing 70 mM phosphate buffer solution (30 mL) and stirred at room temperature for 2 hours to allow the dichloromethane to evaporate and the nanocarriers to form in suspension. A portion of the suspended nanocarriers was washed by transferring the nanocarrier suspension to a centrifuge tube, spinning at 13,823 g for one hour, removing the supernatant, and re-suspending the pellet in phosphate buffered saline. This washing procedure was repeated and then the pellet was re-suspended in phosphate buffered saline to achieve a nanocarrier suspension having a nominal concentration of 10 mg/mL on a polymer basis. The suspension was stored frozen at −20° C. until use.

TABLE 2

Nanocarrier Characterization

| Nanocarrier ID | Effective Diameter (nm) | R848 (% w/w) | Ovalbumin Protein (% w/w) | Ovalbumin Peptide (% w/w) |
|---|---|---|---|---|
| 2 | 234 | 3.9 | 0.3 | 2.3 |

Example 3

Synthetic Nanocarrier Formulation Lot #3

Materials

Ovalbumin protein, was purchased from Worthington Biochemical Corporation (730 Vassar Avenue, Lakewood, N.J. 08701. Product Code 3048.) PLGA-R848 of approximately 5,200 Da made from PLGA of 3:1 lactide to glycolide ratio and having 12.7% w/w conjugated R848 content was synthesized. PLA-PEG-OMe block co-polymer with a methyl ether terminated PEG block of 2,000 Da and DL-PLA block of approximately 19,000 Da was synthesized. PLA with an inherent viscosity of 0.21 dL/g was purchased from SurModics Pharmaceuticals (756 Tom Martin Drive, Birmingham, Ala. 35211. Product Code 100 DL 2A.) Polyvinyl alcohol (Mw=11,000-31,000, 87-89% hydrolyzed) was purchased from J. T. Baker (Part Number U232-08).

Method

Solutions were prepared as follows:

Solution 1: Ovalbumin protein at 20 mg/mL in 10 mM phosphate buffer.

Solution 2: PLGA-R848 at 50 mg/mL, PLA-PEG-OMe at 25 mg/mL, PLA at 25 mg/ml in dichloromethane. The solution was prepared by separately dissolving each polymer as a 100 mg/mL in dichloromethane, then mixing the solutions by adding 2 parts PLGA-R848 solution to 1 part each PLA-PEG-OMe solution and PLA solution.

Solution 3: Polyvinyl alcohol @ 50 mg/mL in 100 mM in 100 mM phosphate buffer, pH 8.

Solution 4: 70 mM phosphate buffer, pH 8.

A primary (W1/O) emulsion was first created using Solution 1 & Solution 2. Solution 1 (0.2 mL) and Solution 2 (1.0 mL) were combined in a small glass pressure tube and sonicated at 50% amplitude for 40 seconds using a Branson Digital Sonifier 250. A secondary (W1/O/W2) emulsion was then formed by adding Solution 3 (2.0 mL) to the primary emulsion, and then sonicating at 30% amplitude for 40 seconds using the Branson Digital Sonifier 250. The secondary emulsion was added to an open 50 mL beaker containing 70 mM phosphate buffer solution (30 mL) and stirred at room temperature for 2 hours to allow the dichloromethane to evaporate and the nanocarriers to form in suspension. A portion of the suspended nanocarriers was washed by transferring the nanocarrier suspension to a centrifuge tube, spinning at 13,823 g for one hour, removing the supernatant, and re-suspending the pellet in phosphate buffered saline. This washing procedure was repeated and then the pellet was re-suspended in phosphate buffered saline to achieve a nanocarrier suspension having a nominal concentration of 10 mg/mL on a polymer basis. The suspension was stored frozen at −20° C. until use.

TABLE 3

Nanocarrier Characterization

| Nanocarrier ID | Effective Diameter (nm) | R848 (% w/w) | Ovalbumin (% w/w) |
|---|---|---|---|
| 3 | 217 | 4.3 | 0.8 |

Example 4

Synthetic Nanocarrier Formulation Lot #4

Ovalbumin protein, was purchased from Worthington Biochemical Corporation (730 Vassar Avenue, Lakewood, N.J. 08701. Product Code 3048.) Ovalbumin peptide 323-339 amide acetate salt, was purchased from Bachem Americas Inc. (3132 Kashiwa Street, Torrance Calif. 90505. Product code 4065609.) PLGA-R848 of approximately 5,200 Da made from PLGA of 3:1 lactide to glycolide ratio and having 12.7% w/w conjugated R848 content was synthesized. PLA-PEG-OMe block co-polymer with a methyl ether terminated PEG block of 2,000 Da and DL-PLA block of approximately 19,000 Da was synthesized. PLA with an inherent viscosity of 0.21 dL/g was purchased from SurModics Pharmaceuticals (756 Tom Martin Drive, Birmingham, Ala. 35211. Product Code 100 DL 2A.) Polyvinyl alcohol (Mw=11,000-31,000, 87-89% hydrolyzed) was purchased from J. T. Baker (Part Number U232-08).

Method

Solutions were prepared as follows:

Solution 1A: Ovalbumin protein at 40 mg/mL in 10 mM phosphate buffer.

Solution 1B: Ovalbumin peptide amide 323-339 @ 40 mg/mL in dilute hydrochloric acid aqueous solution.

Solution 2: PLGA-R848 at 50 mg/mL, PLA-PEG-OMe at 25 mg/mL, PLA at 25 mg/ml in dichloromethane. The solution was prepared by separately dissolving each polymer as a 100 mg/mL in dichloromethane, then mixing the solutions by adding 2 parts PLGA-R848 solution to 1 part each PLA-PEG-OMe solution and PLA solution.

Solution 3: Polyvinyl alcohol @ 50 mg/mL in 100 mM in 100 mM phosphate buffer, pH 8.

Solution 4: 70 mM phosphate buffer, pH 8.

The first primary (W1/O) emulsion was created using Solution 1A & Solution 2. Solution 1A (0.2 mL) and Solution 2 (1.0 mL) were combined in a small glass pressure tube and sonicated at 50% amplitude for 40 seconds using a Branson Digital Sonifier 250. A second primary (W1/O) emulsion was created using Solution 1B & Solution 2. Solution 1B (0.2 mL) and Solution 2 (1.0 mL) were combined in a small glass pressure tube and sonicated at 50% amplitude for 40 seconds using a Branson Digital Sonifier 250. The two primary emulsions were combined, in part, by transferring 0.6 mL of each into a third glass pressure tube to create a 1:1 mixture of the two primary emulsions in a total volume of approximately 1.2 mL. A secondary (W1/O/W2) emulsion was then formed by adding Solution 3 (2.0 mL) to the primary emulsion, and then sonicating at 30% amplitude for 40 seconds using the Branson Digital Sonifier 250. The secondary emulsion was added to an open 50 mL beaker containing 70 mM phosphate buffer solution (30 mL) and stirred at room temperature for 2 hours to allow the dichloromethane to evaporate and the nanocarriers to form in suspension. A portion of the suspended nanocarriers was washed by transferring the nanocarrier suspension to a centrifuge tube, spinning at 13,823 g for one hour, removing the supernatant, and re-suspending the pellet in phosphate buffered saline. This washing procedure was repeated and then the pellet was re-suspended in phosphate buffered saline to achieve a nanocarrier suspension having a nominal concentration of 10 mg/mL on a polymer basis. The suspension was stored frozen at −20° C. until use.

TABLE 4

Nanocarrier Characterization

| Nanocarrier ID | Effective Diameter (nm) | R848 (% w/w) | Ovalbumin Protein (% w/w) | Ovalbumin Peptide (% w/w) |
|---|---|---|---|---|
| 4 | 213 | 3.8 | 0.3 | 0.8 |

Example 5

Synthetic Nanocarrier Formulation Lot #5

Materials

SIINFEKL (SEQ ID NO: 1) (ovalbumin peptide [257-264]), was purchased from Bachem Americas Inc. (3132 Kashiwa Street, Torrance Calif. 90505. Product code H-4866.) Ovalbumin peptide 323-339 amide acetate salt, was purchased from Bachem Americas Inc. (3132 Kashiwa Street, Torrance Calif. 90505. Product code 4065609.) PLGA-R848 of approximately 4,500 Da made from PLGA of 3:1 lactide to glycolide ratio and having 15% w/w conjugated R848 content was synthesized. PLA-PEG-Nicotine with a nicotine-terminated PEG block of approximately 5,000 Da and DL-PLA block of approximately 17,000 Da was synthesized. PLA with an inherent viscosity of 0.21 dL/g was purchased from SurModics Pharmaceuticals (756 Tom Martin Drive, Birmingham, Ala. 35211. Product Code 100 DL 2A.) Polyvinyl alcohol (Mw=11,000-31,000, 87-89% hydrolyzed) was purchased from J. T. Baker (Part Number U232-08).

Method

Solutions were prepared as follows:

Solution 1A: SIINFEKL (SEQ ID NO: 1) @ 200 mg/mL DMSO.

Solution 1B: Ovalbumin peptide amide 323-339 @ 20 mg/mL in dilute hydrochloric acid aqueous solution.

Solution 2: PLGA-R848 at 50 mg/mL, PLA-PEG-Nicotine at 25 mg/mL, PLA at 25 mg/ml in dichloromethane. The solution was prepared by separately dissolving each polymer as a 100 mg/mL in dichloromethane, then mixing the solutions by adding 2 parts PLGA-R848 solution to 1 part each PLA-PEG-Nicotine solution and PLA solution.

Solution 3: Polyvinyl alcohol @ 50 mg/mL in 100 mM in 100 mM phosphate buffer, pH 8.

Solution 4: 70 mM phosphate buffer, pH 8.

The first primary (S/O) emulsion was created using Solution 1A & Solution 2. Solution 1A (0.025 mL) and Solution 2 (1.0 mL) were combined in a small glass pressure tube and sonicated at 50% amplitude for 40 seconds using a Branson Digital Sonifier 250. A serial primary (W1/(S/O)) emulsion was created using Solution 1B and the first primary emulsion. Solution 1B (0.25 mL) was added to the small glass pressure tube containing the first primary emulsion and then sonicated at 50% amplitude for 40 seconds using a Branson Digital Sonifier 250. A secondary ((S+W1)/O/W2) emulsion was then formed by adding Solution 3 (2.0 mL) to the serial primary emulsion, and then sonicating at 30% amplitude for seconds using the Branson Digital Sonifier 250. The secondary emulsion was added to an open 50 mL beaker containing 70 mM phosphate buffer solution (30 mL) and stirred at room temperature for 2 hours to allow the dichloromethane to evaporate and the nanocarriers to form in suspension. A portion of the suspended nanocarriers was washed by transferring the nanocarrier suspension to a centrifuge tube, spinning at 13,823 g for one hour, removing the supernatant, and re-suspending the pellet in phosphate buffered saline. This washing procedure was repeated and then the pellet was re-suspended in phosphate buffered saline to achieve a nanocarrier suspension having a nominal concentration of 10 mg/mL on a polymer basis. The suspension was stored frozen at −20° C. until use.

TABLE 5

Nanocarrier Characterization

| Nanocarrier ID | Effective Diameter (nm) | R848 (% w/w) | SIINFEKL (SEQ ID NO: 1) peptide (% w/w) | Ovalbumin 323-339 peptide (% w/w) |
|---|---|---|---|---|
| 5 | 236 | 4.2 | 0.9 | 1.6 |

Example 6

Synthetic Nanocarrier Compositions Generate High Antibody Titers and Strong Antigen-Specific CTL Activity $3^{rd}$ and $4^{th}$ in vivo (C57BL/6 mice) immunization studies were performed. The above polymeric nanocarrier formulation (#3) delivering a TLR agonist (R848) and entrapped ovalbumin protein (OVA) was introduced and created high antibody titers (e.g., anti-OVA IgG titers of ~1e6) and strong antigen-specific CTL activity from local lymph and spleen cells.

Immunized mice were bled at dates indicated and antibodies to ovalbumin measured in standard ELISA using serial dilutions of test sera. Biotinylated goat anti-mouse Ig was used as a detection antibody (BD Biosciences, San Diego, Calif.). EC50 was determined based on titration curves. CTL activity was measured as follows. 4-5 days after the final injection (subcutaneous, s.c., or intranasal, i.n.) with the nanocarrier preparations or protein controls draining lymph nodes (LNs) were removed, treated with collagenase, homogenized, washed and incubated with 10-100 units/ml of IL-2 for 4-5 days. Then resulting cell populations were counted and used as effector cells in cytotoxicity assays. Syngeneic EL-4 cells pulsed with SIINFEKL (SEQ ID NO: 1) peptide or EG.7-OVA cells (stably transfected with ovalbumin) served as targets with intact EL-4 cells providing for background control. Cytoxicity at various effector:target ratios was measured over 24 hours (37° C.) using CytoTox-ONE™ Homogenuous Membrane Integrity Assay (Promega, Madison, Wis.) according to manufacturer's recommendations.

TABLE 6

Formulation of Nanocarrier

| Antigen | OVA Protein |
| --- | --- |
| TLR Agonist | PLGA-R848 (50%) |
| Matrix polymer 1 | PLA-PEG (25%) |
| Matrix Polymer 2 | 100 DL 2A (25%) |

TABLE 7

Experiment 1 Layout

| Gr. # | Immunized with | NC Lot# | R848 load (%) | Ova Protein load (%) | Ova peptide load (%) |
| --- | --- | --- | --- | --- | --- |
| 1 | NC (ovalbumin; no memory peptide) | 1 | 4.0 | 1.1 | N/A |
| 2 | NC (ovalbumin; +memory peptide) | 2 | 3.9 | 0.3 | 2.3 |
| 3 | NC (ovalbumin; no memory peptide) | 3 | 4.3 | 0.8 | N/A |
| 4 | NC (ovalbumin; +memory peptide) | 4 | 3.8 | 0.3 | 0.8 |
| 5 | Ovalbumin (100 μg) + 20 μg free CpG | N/A | N/A | 100 μg | N/A |
| 6 | Ovalbumin (100 μg) + 100 μg alum | N/A | N/A | 100 μg | N/A |

TABLE 8

Experiment 2 layout

| Gr. # | Immunized with | Route | NC Lot# | R848 load (%) | Ova Protein load (%) | Ova peptide load (%), type |
| --- | --- | --- | --- | --- | --- | --- |
| 1 | NC (SIINFEKL (SEQ ID NO: 1) + memory peptide) | S.c. | 5 | 4.2 | N/A | 1.6-peptide 0.9-SIINFEKL (SEQ ID NO: 1) |
| 2 | NC (ovalbumin; no memory peptide) | S.c | 3 | 4.3 | 0.8 | N/A |

TABLE 8-continued

Experiment 2 layout

| Gr. # | Immunized with | Route | NC Lot# | R848 load (%) | Ova Protein load (%) | Ova peptide load (%), type |
| --- | --- | --- | --- | --- | --- | --- |
| 3 | NC (SIINFEKL (SEQ ID NO: 1) + memory peptide) | I.n. | 5 | 4.2 | N/A | 1.6-peptide 0.9-SIINFEKL (SEQ ID NO: 1) |
| 4 | NC (ovalbumin; no memory peptide) | I.n. | 3 | 4.3 | 0.8 | N/A |

Example 7

Synthetic Nanocarrier Formulation Lot #6

Materials

Ovalbumin protein, was purchased from Worthington Biochemical Corporation (730 Vassar Avenue, Lakewood, N.J. 08701). Product Code LS003054. PLGA-R848, Poly-D/L-lactide-co-glycolide, 4-amino-2-(ethoxymethyl)-α,α-dimethyl-1H-imidazo[4,5-c]quinoline-1-ethanol amide of approximately 7,800 Da made from PLGA of 3:1 lactide to glycolide ratio and having 8.5% w/w conjugated resiquimod content was custom manufactured at Princeton Global Synthesis (300 George Patterson Drive #206, Bristol, Pa. 19007.) Lot number PGS 16-52. PLA with an inherent viscosity of 0.21 dL/g was purchased from SurModics Pharmaceuticals (756 Tom Martin Drive, Birmingham, Ala. 35211. Product Code 100 DL 2A.) PLA-PEG-OMe block co-polymer with a methyl ether terminated PEG block of approximately 5,000 Da and PLA block of approximately 21,000 Da by $^1$H-NMR (Mn of 21 kDa) was synthesized. EMPROVE® Polyvinyl Alcohol 5-88, USP (85-89% hydrolyzed, viscosity of 4.3-5.7 mPa·s) was purchased from EMD Chemicals Inc. (480 South Democrat Road Gibbstown, N.J. 08027. Part Number 1.41354). Phosphate-buffered saline 1× (PBS 1×). From Mediatech Inc. (9345 Discovery Blvd. Manassas, Va. 20109.) Product Code 21-040-CV.

Method

Solutions were prepared as follows:

Solution 1: Ovalbumin protein @ 20 mg/mL was prepared in PBS 1× at room temperature.

Solution 2: PLA was prepared by dissolving PLA at 100 mg per 1 mL of dichloromethane in the chemical fume hood.

Solution 3: PLA-PEG-OMe was prepared by dissolving PLA-PEG-OMe at 100 mg per 1 mL of dichloromethane in the chemical fume hood.

Solution 4: PLGA-R848 was prepared by dissolving PLGA-R848 at 100 mg per 1 mL of dichloromethane in the chemical fume hood.

Solution 5: Polyvinyl alcohol @ 50 mg/mL in 100 mM in 100 mM phosphate buffer, pH 8.

Solution 6: 70 mM phosphate buffer, pH 8.

This lot was prepared in duplicate, then combined after washing. A primary (W1/O) emulsion was first created by mixing Solutions 1 through 4. Solution 1 (0.2 mL), Solution 2 (0.50 mL), Solution 3 (0.25 mL) and Solution 4 (0.25 mL) were combined in a small glass pressure tube and sonicated at 50% amplitude for 40 seconds using a Branson Digital Sonifier 250. A secondary (W1/O/W2) emulsion was then formed by adding Solution 5 (2.0 mL) to the primary emulsion, vortexing to create a crude dispersion, and then sonicating at 30% amplitude for 60 seconds using the Branson Digital Sonifier 250. The secondary emulsion was added to an open 50 mL beaker containing Solution 6 (30 mL) and stirred at room temperature for 2 hours to allow the dichloromethane to evaporate and the nanocarriers to form in suspension. A portion of the suspended nanocarriers was washed by transferring the nanocarrier suspension to a centrifuge tube, spinning at 21,000 rcf for 45 minutes, removing the supernatant, and re-suspending the pellet in phosphate buffered saline. This washing procedure was repeated and then the pellet was re-suspended in PBS 1× to achieve a nanocarrier suspension having a nominal concentration of 10 mg/mL on a polymer basis. The suspension was stored frozen at −20 C until use.

TABLE 9

Nanocarrier Characterization

| Nanocarrier ID | Effective Diameter (nm) | TLR Agonist, % w/w | Antigen, % w/w |
|---|---|---|---|
| 6 | 252.1 | R848, 4.4 | OVA protein, 4.3 |

Example 8

Synthetic Nanocarrier Formulation Lot #7

Materials

Ovalbumin protein, was purchased from Worthington Biochemical Corporation (730 Vassar Avenue, Lakewood, N.J. 08701). Product Code LS003054. PLGA-R848, Poly-D/L-lactide-co-glycolide, 4-amino-2-(ethoxymethyl)-α,α-dimethyl-1H-imidazo[4,5-c]quinoline-1-ethanol amide of approximately 7,800 Da made from PLGA of 3:1 lactide to glycolide ratio and having 8.5% w/w conjugated resiquimod content was custom manufactured at Princeton Global Synthesis (300 George Patterson Drive #206, Bristol, Pa. 19007.) Lot number PGS 16-52. PLA with an inherent viscosity of 0.21 dL/g was purchased from SurModics Pharmaceuticals (756 Tom Martin Drive, Birmingham, Ala. 35211. Product Code 100 DL 2A.) PLA-PEG-OMe block co-polymer with a methyl ether terminated PEG block of approximately 5,000 Da and PLA block of approximately 21,000 Da by $^1$H-NMR (Mn of 21 kDa) was synthesized. EMPROVE® Polyvinyl Alcohol 5-88, USP (85-89% hydrolyzed, viscosity of 4.3-5.7 mPa·s) was purchased from EMD Chemicals Inc. (480 South Democrat Road Gibbstown, N.J. 08027. Part Number 1.41354). Phosphate-buffered saline 1× (PBS 1×). From Mediatech Inc. (9345 Discovery Blvd. Manassas, Va. 20109.) Product Code 21-040-CV.

Method

Solutions were prepared as follows:

Solution 1: Ovalbumin protein @ 5 mg/mL was prepared in PBS 1× at room temperature.

Solution 2: PLA was prepared by dissolving PLA at 100 mg per 1 mL of dichloromethane in the chemical fume hood.

Solution 3: PLA-PEG-OMe was prepared by dissolving PLA-PEG-OMe at 100 mg per 1 mL of dichloromethane in the chemical fume hood.

Solution 4: PLGA-R848 was prepared by dissolving PLGA-R848 at 100 mg per 1 mL of dichloromethane in the chemical fume hood.

Solution 5: Polyvinyl alcohol @ 50 mg/mL in 100 mM in 100 mM phosphate buffer, pH 8.

Solution 6: 70 mM phosphate buffer, pH 8.

This lot was prepared in duplicate, then combined after washing. A primary (W1/O) emulsion was first created by mixing Solutions 1 through 4. Solution 1 (0.2 mL), Solution 2 (0.50 mL), Solution 3 (0.25 mL) and Solution 4 (0.25 mL) were combined in a small glass pressure tube and sonicated at 50% amplitude for 40 seconds using a Branson Digital Sonifier 250. A secondary (W1/O/W2) emulsion was then formed by adding Solution 5 (2.0 mL) to the primary emulsion, vortexing to create a crude dispersion, and then sonicating at 30% amplitude for 60 seconds using the Branson Digital Sonifier 250. The secondary emulsion was added to an open 50 mL beaker containing Solution 6 (30 mL) and stirred at room temperature for 2 hours to allow the dichloromethane to evaporate and the nanocarriers to form in suspension. A portion of the suspended nanocarriers was washed by transferring the nanocarrier suspension to a centrifuge tube, spinning at 21,000 rcf for 45 minutes, removing the supernatant, and re-suspending the pellet in phosphate buffered saline. This washing procedure was repeated and then the pellet was re-suspended in PBS 1× to achieve a nanocarrier suspension having a nominal concentration of 10 mg/mL on a polymer basis. The suspension was stored frozen at −20 C until use.

TABLE 10

Nanocarrier Characterization

| Nanocarrier ID | Effective Diameter (nm) | TLR Agonist, % w/w | Antigen, % w/w |
|---|---|---|---|
| 7 | 240.6 | R848, 4.2 | OVA protein, 1.3 |

Example 9

Synthetic Nanocarrier Formulation Lot #8

Materials

Ovalbumin protein, was purchased from Worthington Biochemical Corporation (730 Vassar Avenue, Lakewood, N.J. 08701). Product Code LS003054. PLGA-R848, Poly-D/L-lactide-co-glycolide, 4-amino-2-(ethoxymethyl)-α,α-dimethyl-1H-imidazo[4,5-c]quinoline-1-ethanol amide of approximately 7,800 Da made from PLGA of 3:1 lactide to glycolide ratio and having 8.5% w/w conjugated resiquimod content was custom manufactured at Princeton Global Synthesis (300 George Patterson Drive #206, Bristol, Pa. 19007.) PLA with an inherent viscosity of 0.21 dL/g was purchased from SurModics Pharmaceuticals (756 Tom Martin Drive, Birmingham, Ala. 35211. Product Code 100 DL 2A.) PLA-PEG-OMe block co-polymer with a methyl ether terminated PEG block of approximately 5,000 Da and PLA block of approximately 21,000 Da by $^1$H-NMR (Mn of 21 kDa) was synthesized. EMPROVE® Polyvinyl Alcohol 5-88, USP (85-89% hydrolyzed, viscosity of 4.3-5.7 mPa·s) was purchased from EMD Chemicals Inc. (480 South Democrat Road Gibbstown, N.J. 08027. Part Number 1.41354). Phosphate-buffered saline 1× (PBS 1×). From Mediatech Inc. (9345 Discovery Blvd. Manassas, Va. 20109.) Product Code 21-040-CV.

Method

Solutions were prepared as follows:

Solution 1: Ovalbumin protein @ 20 mg/mL was prepared in PBS 1× at room temperature.

Solution 2: PLA was prepared by dissolving PLA at 100 mg per 1 mL of dichloromethane in the chemical fume hood.

Solution 3: PLA-PEG-OMe was prepared by dissolving PLA-PEG-OMe at 100 mg per 1 mL of dichloromethane in the chemical fume hood.

Solution 4: PLGA-R848 was prepared by dissolving PLGA-R848 at 100 mg per 1 mL of dichloromethane in the chemical fume hood.

Solution 5: Polyvinyl alcohol @ 50 mg/mL in 100 mM in 100 mM phosphate buffer, pH 8.

Solution 6: 70 mM phosphate buffer, pH 8.

This lot was prepared in duplicate, then combined after washing. A primary (W1/O) emulsion was first created by mixing Solutions 1 through 4. Solution 1 (0.2 mL), Solution 2 (0.50 mL), Solution 3 (0.25 mL) and Solution 4 (0.25 mL) were combined in a small glass pressure tube and sonicated at 50% amplitude for 40 seconds using a Branson Digital Sonifier 250. A secondary (W1/O/W2) emulsion was then formed by adding Solution 5 (2.0 mL) to the primary emulsion, vortexing to create a crude dispersion, and then sonicating at 30% amplitude for 60 seconds using the Branson Digital Sonifier 250. The secondary emulsion was added to an open 50 mL beaker containing Solution 6 (30 mL) and stirred at room temperature for 2 hours to allow the dichloromethane to evaporate and the nanocarriers to form in suspension. A portion of the suspended nanocarriers was washed by transferring the nanocarrier suspension to a centrifuge tube, spinning at 21,000 rcf for 45 minutes, removing the supernatant, and re-suspending the pellet in phosphate buffered saline. This washing procedure was repeated and then the pellet was re-suspended in PBS 1× to achieve a nanocarrier suspension having a nominal concentration of 10 mg/mL on a polymer basis. The suspension was stored frozen at −20 C until use.

TABLE 11

Nanocarrier Characterization

| Nanocarrier ID | Effective Diameter (nm) | TLR Agonist, % w/w | Antigen, % w/w |
|---|---|---|---|
| 8 | 238.6 | R848, 3.9 | OVA protein, 8.0 |

Example 10

Synthetic Nanocarrier Compositions Generate High Antibody Titers and Strong Antigen-Specific CTL Activity Synthetic nanocarriers delivering R848 and OVA was as successful as a positive comparator control consisting of high dose of PS-CpG plus a 6× higher dose of free OVA at generating a central (spleen) OVA-specific CTL response and also in creating as strong (or stronger) OVA-specific humoral response.

4-5 days after s.c. injection with nanocarrier preparations or controls draining lymph nodes (LNs) were removed, treated with collagenase, homogenized, washed and incubated with 10-100 units/ml of IL-2 for 4-5 days. Then resulting cell populations were counted and used as effector cells in cytotoxicity assay. Syngeneic EL-4 cells pulsed with SIINFEKL (SEQ ID NO: 1) peptide or EG.7-OVA cells (stably transfected with ovalbumin) served as targets with intact EL-4 cells providing for background control. Cytoxicity at various effector:target ratios was measured over 24 hours (37° C.) using CytoTox-ONE™ Homogenuous Membrane Integrity Assay (Promega, Madison, Wis.) according to manufacturer's recommendations.

TABLE 12

| Gr. # | Immunized w. | NC Lot | Adjuvant (µg) | OVA (µg) |
|---|---|---|---|---|
| 1 | NC-OVA-R848 | 6 | R848 (4.4) | 4.3 |
| 2 | NC-OVA-R848 | 7 | R848 (4.2) | 1.3 |
| 3 | NC-OVA-R848 | 8 | R848 (3.9) | 8.0 |
| 4 | OVA + CpG | N/A | CpG, 20 µg | 50 |

Example 11

Measure Development of Humoral and Cellular Immune Responses to Nanocarrier-encapsulated Antigen After a Single Injection of NC-OVA+NC-R848 Mix Materials—Lot #9

PLGA-R848 (S-205), Poly-D/L-lactide-co-glycolide, 4-amino-2-(ethoxymethyl)-α,α-dimethyl-1H-imidazo[4,5-c]quinoline-1-ethanol amide of approximately 7,800 Da made from PLGA of 3:1 lactide to glycolide ratio and having 8.5% w/w conjugated resiquimod content was custom manufactured at Princeton Global Synthesis (300 George Patterson Drive #206, Bristol, Pa. 19007.). PLA with an inherent viscosity of 0.19 dL/g was purchased from Sur-Modics Pharmaceuticals (756 Tom Martin Drive, Birmingham, Ala. 35211. Product Code 100 DL 2A). PLA-PEG-OMe block co-polymer with a methyl ether terminated PEG block of approximately 5,000 Da and PLA block of approximately 28,000 Da was purchased from SurModics Pharmaceuticals (Product Code 100 DL mPEG 5000 5CE). EMPROVE® Polyvinyl Alcohol 4-88, USP (85-89% hydrolyzed, viscosity of 3.4-4.6 mPa·s) was purchased from EMD Chemicals Inc. (480 South Democrat Road Gibbstown, N.J. 08027). Phosphate-buffered saline 1× (PBS 1×). From Mediatech Inc. (9345 Discovery Blvd. Manassas, Va. 20109.) Product Code 21-040-CV.

Method—Lot #9

Solutions were prepared as follows:

Solution 1: PLGA-R848 was prepared by weighing out PLGA-R848, PLA, and PLA-PEG-OMe powders in 2:1:1 weight ratio and then dissolving the mixed polymers in dichloromethane to achieve a total polymer concentration of 100 mg per 1 mL.

Solution 2: Polyvinyl alcohol @ 35 mg/mL in 100 mM phosphate buffer, pH 8.

An O/W emulsion was created by mixing Solutions 1 and 2, and then creating a coarse emulsion prior to a fine emulsion. Solution 1 (2 mL) was coarsely emulsified with Solution 2 (8 mL), using 10 passes through an 18 G emulsification needle. A fine emulsion was made by loading the coarse emulsion into a primed and ice-water-chilled high pressure homogenizer (Microfluidics LV1) and performing three passes at 5000 psi. The fine O/W emulsion was added to an open 100 mL beaker containing 1×PBS (60 mL) and stirred at room temperature for more than 2 hours to allow the dichloromethane to evaporate and the nanocarriers to form in suspension. A portion of the suspended nanocarriers was washed by transferring the nanocarrier suspension to a centrifuge tube, spinning at 75,600 rcf for 35 minutes, removing the supernatant, and re-suspending the pellet in phosphate buffered saline. This washing procedure was repeated and then the pellet was re-suspended in PBS 1× to achieve a nanocarrier suspension having a nominal concentration of 10 mg/mL on a polymer basis. The nanocarrier formation process was repeated another three times at 1× or 2× the same scale. The four suspensions were combined and then filtered through 0.22 micron PES syringe filter and then stored frozen at −20 C until use.

Materials—Lot #10

PLGA-R848 (S-205), Poly-D/L-lactide-co-glycolide, 4-amino-2-(ethoxymethyl)-α,α-dimethyl-1H-imidazo[4,5-c]quinoline-1-ethanol amide of approximately 7,800 Da made from PLGA of 3:1 lactide to glycolide ratio and having 8.5% w/w conjugated resiquimod content was custom manufactured at Princeton Global Synthesis (300 George Patterson Drive #206, Bristol, Pa. 19007.). PLA with an inherent viscosity of 0.19 dL/g was purchased from SurModics Pharmaceuticals (756 Tom Martin Drive, Birmingham, Ala. 35211. Product Code 100 DL 2A). PLA-PEG-OMe block co-polymer with a methyl ether terminated PEG block of approximately 5,000 Da and PLA block of approximately 28,000 Da was purchased from SurModics Pharmaceuticals (Product Code 100 DL mPEG 5000 5CE). EMPROVE® Polyvinyl Alcohol 4-88, USP (85-89% hydrolyzed, viscosity of 3.4-4.6 mPa·s) was purchased from EMD Chemicals Inc. (480 South Democrat Road Gibbstown, N.J. 08027). Phosphate-buffered saline 1× (PBS 1×). From Mediatech Inc. (9345 Discovery Blvd. Manassas, Va. 20109.) Product Code 21-040-CV.

Method—Lot #10

Solutions were prepared as follows:

Solution 1: PLGA-R848 was prepared by dissolving PLGA-R848 at 100 mg per 1 mL of dichloromethane in the chemical fume hood.

Solution 2: PLA was prepared by dissolving PLA at 100 mg per 1 mL of dichloromethane in the chemical fume hood.

Solution 3: PLA-PEG-OMe was prepared by dissolving PLA-PEG-OMe at 100 mg per 1 mL of dichloromethane in the chemical fume hood.

Solution 4: Polyvinyl alcohol @ 50 mg/mL in 100 mM phosphate buffer, pH 8.

A primary (O/W) emulsion was created by mixing Solutions 1 through 4 and creating a coarse emulsion prior to a fine emulsion. Solution 1 (1 mL), Solution 2 (0.5 mL), and Solution 3 (0.5 mL) were combined first and then coarsely emulsified with Solution 4 (8 mL), by stirring together at 350 rpm in a 50 mL beaker for two minutes and by repeat pipetting. A fine emulsion, was made by loading the coarse emulsion into a primed high pressure homogenizer (Microfluidics LV1) and performing three passes at 5000 psi. The fine O/W emulsion was added to an open 50 mL beaker containing 1×PBS (30 mL) and stirred at room temperature for more than 2 hours to allow the dichloromethane to evaporate and the nanocarriers to form in suspension. A portion of the suspended nanocarriers was washed by transferring the nanocarrier suspension to a centrifuge tube, spinning at 75,600 rcf for 35 minutes, removing the supernatant, and re-suspending the pellet in phosphate buffered saline. This washing procedure was repeated and then the pellet was re-suspended in PBS 1× to achieve a nanocarrier suspension having a nominal concentration of 10 mg/mL on a polymer basis. Nanocarrier suspension was then filtered through a 0.22 micron PES syringe filter and then stored frozen at −20 C until use.

Materials—Lot #11

Ovalbumin protein, was purchased from Worthington Biochemical Corporation (730 Vassar Avenue, Lakewood, N.J. 08701). Product Code LS003054. PLGA with 75% lactide and 25% glycolide content and an inherent viscosity of 0.24 dL/g was purchased from SurModics Pharmaceuticals (756 Tom Martin Drive, Birmingham, Ala. 35211. Product Code 7525 DLG 2.5A). PLA with an inherent viscosity of 0.2 dL/g was purchased from SurModics Pharmaceuticals (Product Code 100 DL 2A). PLA-PEG-OMe block co-polymer with a methyl ether terminated PEG block of approximately 5,000 Da and PLA block of approximately 21,000 Da was synthesized. EMPROVE® Polyvinyl Alcohol 4-88, USP (85-89% hydrolyzed, viscosity of 3.4-4.6 mPa·s) was purchased from EMD Chemicals Inc. (480 South Democrat Road Gibbstown, N.J. 08027). Phosphate-buffered saline IX (PBS IX). From Mediatech Inc. (9345 Discovery Blvd. Manassas, Va. 20109.) Product Code 21-040-CV.

Method—Lot #11

Solutions were prepared as follows:

Solution 1: Ovalbumin protein @ 50 mg/mL was prepared in PBS 1× at room temperature.

Solution 2: PLGA, PLA, and PLA-PEG-OMe were weighed out in 2:1:1 weight ratio and dissolved in dichloromethane in the chemical fume hood to achieve a final total polymer concentration of 100 mg per 1 mL.

Solution 3: Polyvinyl alcohol @ 50 mg/mL in 100 mM phosphate buffer, pH 8.

Solution 4: 70 mM phosphate buffer, pH 8.

A primary (W1/O) emulsion was first created by mixing Solutions 1 and 2. Solution 1 (66 mL) and Solution 2 (264 mL) were combined and formed into a coarse emulsion using an overhead mixer in a 1 L beaker. The coarse emulsion was transferred to a custom-made temperature-controlled homogenization vessel and homogenized using a high-shear rotor stator. A coarse secondary (W1/O/W2) emulsion was then formed by transferring 2 of the primary emulsion into a beaker containing 330 mL of Solution 3 and mixing with an overhead mixer. The coarse secondary emulsion was then returned to a custom homogenization vessel and homogenized to a fine emulsion using high shear. The secondary emulsion was then added to a purged 6 L vessel containing Solution 4 (3.2 L) and shaken overnight at room temperature to evaporate and the nanocarriers to form in suspension. Portions (30 mL each) of the suspended nanocarriers were washed by transferring the nanocarrier suspension to a centrifuge tube, spinning at 75,600 rcf for 35 minutes, removing the supernatant, and re-suspending the pellet in phosphate buffered saline. This washing procedure was repeated and then the pellet was re-suspended in PBS 1× to achieve the target nanocarrier concentration. The suspension was filtered and stored frozen at −20 C until use.

C57BL/6 female mice (2-3/group) were immunized once by a mix of 100 g NC-OVA and 100 g of NC-R848 containing 4.3 g R848 and 6.2 g of OVA (per each mouse). At days 4, 7, 10 and 14 after nanocarrier inoculation mice were bled and their antibody (IgG) titer against OVA determined by ELISA. Additionally, at the same time-points mice were injected (i.v.) by syngeneic splenocytes pulsed by a peptide representing a dominant CTL epitope of OVA (SIINFEKL (SEQ ID NO: 1)) and differentially labeled by CSFE. The next day, splenocytes from immunized mice were taken and analyzed by FACS and specific cytotoxicity in each animal determined compared to basic cytotoxicity level in PBS-injected (naïve) animals (%=100×[1−RRnaive/RRimm]).

A single immunization with NC-OVA+NC-R848 leads to rapid induction of cellular and humoral immune responses with the former being detected as early as four days after injection and then persisting for at least ten days with a peak at day 7, and the latter being detected at seven days after injection and reaching a significant level at 10 days after inoculation.

Example 12

Synthetic Nanocarriers Delivering CpG and OVA

Materials—Lot #12

PO-1826 DNA oligonucleotide with phosphodiester backbone having nucleotide sequence 5'-TCC ATG ACG TTC CTG ACG TT-3' (SEQ ID NO:2) with a sodium counter-ion was purchased from Oligo Factory (120 Jeffrey Avenue, Holliston, Mass. 01746.) PLGA having 54% lactide and 46% glycolide content and an inherent viscosity of 0.24 dL/g was purchased from SurModics Pharmaceuticals (756 Tom Martin Drive, Birmingham, Ala. 35211. Product Code 5050 DLG 2.5A). PLGA-PEG-OMe block co-polymer with a methyl ether terminated PEG block of approximately 2,000 Da and 75% lactide/25% glycolide PLGA block of approximately 88,000 Da was purchased from SurModics Pharmaceuticals (Product Code 7525 DLG PEG 2000 7E-P). EMPROVE® Polyvinyl Alcohol 4-88, USP (85-89% hydrolyzed, viscosity of 3.4-4.6 mPa·s) was purchased from EMD Chemicals Inc. (480 South Democrat Road Gibbstown, N.J. 08027). Phosphate-buffered saline 1× (PBS 1×). From Mediatech Inc. (9345 Discovery Blvd. Manassas, Va. 20109.) Product Code 21-040-CV.

Method—Lot #12

Solutions were prepared as follows:

Solution 1: PO-1826 was prepared by dissolving at 40 mg per 1 mL of an aqueous solution containing 250 mg Na cholate per 1 mL endotoxin-free water.

Solution 2: PLGA was prepared by dissolving PLA at 100 mg per 1 mL of dichloromethane in the chemical fume hood.

Solution 3: PLGA-PEG-OMe was prepared by dissolving PLGA-PEG-OMe at 100 mg per 1 mL of dichloromethane in the chemical fume hood.

Solution 4: Polyvinyl alcohol @ 50 mg/mL in 100 mM phosphate buffer, pH 8.

Solution 5: 70 mM phosphate buffer, pH 8.

A primary (W/O) emulsion was created by mixing Solutions 1 through 3 and creating a coarse emulsion prior to a fine emulsion. Solution 1 (0.2 mL), Solution 2 (0.5 mL), and Solution 3 (0.5 mL) were combined in a small glass pressure tube, coarsely emulsified by repeat pipetting, and sonicated at 50% amplitude for 40 seconds over an ice bath using a Branson Digital Sonifier 250. A secondary (W1/O/W2) emulsion was then formed by adding Solution 4 (3.0 mL) to the primary emulsion, vortexing to create a crude dispersion, and then sonicating at 30% amplitude for 60 seconds over an ice bath using the Branson Digital Sonifier 250. The fine W1/O/W2 emulsion was added to an open 50 mL beaker containing 70 mM phosphate buffer (30 mL) and stirred at room temperature for 2 hours to allow the dichloromethane to evaporate and the nanocarriers to form in suspension. A portion of the suspended nanocarriers was washed by transferring the nanocarrier suspension to a centrifuge tube, spinning at 21,000 rcf for 90 minutes, removing the supernatant, and re-suspending the pellet in phosphate buffered saline. This washing procedure was repeated and then the pellet was re-suspended in PBS 1× to achieve a nanocarrier suspension having a nominal concentration of 10 mg/mL on a polymer basis. Nanocarrier suspension was then filtered through 0.22 micron PES syringe filters, stored refrigerated until the concentration was determined, and then concentration adjusted and stored frozen at −20 C until use.

Materials—Lot #13

Ovalbumin protein, was purchased from Worthington Biochemical Corporation (730 Vassar Avenue, Lakewood, N.J. 08701). Product Code LS003054. PLGA with 75% lactide and 25% glycolide content and an inherent viscosity of 0.2 dL/g was purchased from SurModics Pharmaceuticals (756 Tom Martin Drive, Birmingham, Ala. 35211. Product Code 7525 DLG 2A). PLA-PEG-OMe block co-polymer with a methyl ether terminated PEG block of approximately 5,000 Da and PLA block of approximately 21,000 Da by $^1$H-NMR (Mn of 21 kDa) was synthesized. EMPROVE® Polyvinyl Alcohol 4-88, USP (85-89% hydrolyzed, viscosity of 3.4-4.6 mPa·s) was purchased from EMD Chemicals Inc. (480 South Democrat Road Gibbstown, N.J. 08027). Phosphate-buffered saline IX (PBS IX). From Mediatech Inc. (9345 Discovery Blvd. Manassas, Va. 20109.) Product Code 21-040-CV.

Method—Lot #13

Solutions were prepared as follows:

Solution 1: Ovalbumin protein @ 50 mg/mL was prepared in PBS 1× at room temperature.

Solution 2: PLGA was prepared by dissolving PLGA at 100 mg per 1 mL of dichloromethane in the chemical fume hood.

Solution 3: PLA-PEG-OMe was prepared by dissolving PLA-PEG-OMe at 100 mg per 1 mL of dichloromethane in the chemical fume hood.

Solution 4: Polyvinyl alcohol @ 50 mg/mL in 100 mM phosphate buffer, pH 8.

Solution 5: 70 mM phosphate buffer, pH 8.

A primary (W1/O) emulsion was first created by mixing Solutions 1 through 3. Solution 1 (0.2 mL), Solution 2 (0.75 mL), and Solution 3 (0.25 mL) were combined in a small glass pressure tube and sonicated at 50% amplitude for 40 seconds over an ice bath using a Branson Digital Sonifier 250. A secondary (W1/O/W2) emulsion was then formed by adding Solution 4 (3.0 mL) to the primary emulsion, vortexing to create a crude dispersion, and then sonicating at 30% amplitude for 60 seconds over an ice bath using the Branson Digital Sonifier 250. The secondary emulsion was added to an open 50 mL beaker containing Solution 5 (30 mL) and stirred at room temperature for 2 hours to allow the dichloromethane to evaporate and the nanocarriers to form in suspension. A portion of the suspended nanocarriers was washed by transferring the nanocarrier suspension to a centrifuge tube, spinning at 21,000 rcf for 130 minutes, removing the supernatant, and re-suspending the pellet in phosphate buffered saline. This washing procedure was repeated and then the pellet was re-suspended in PBS 1× to achieve a nanocarrier suspension having a nominal concentration of 10 mg/mL on a polymer basis. The suspension was stored frozen at −20 C until use.

Materials—Lot #14

Ovalbumin protein, was purchased from Worthington Biochemical Corporation (730 Vassar Avenue, Lakewood, N.J. 08701. Product Code LS003054). PLGA with 76% lactide and 24% glycolide content and an inherent viscosity of 0.69 dL/g was purchased from SurModics Pharmaceuticals (756 Tom Martin Drive, Birmingham, Ala. 35211. Product Code 7525 DLG 7A). PLA with an inherent viscosity of 0.22 dL/g was purchased from SurModics Pharmaceuticals (Product Code 100 DL 2A). PLA-PEG-OMe block co-polymer with a methyl ether terminated PEG block of approximately 5,000 Da and PLA block of approximately 21,000 Da was synthesized. EMPROVE® Polyvinyl Alcohol 4-88, USP (85-89% hydrolyzed, viscosity of 3.4-4.6 mPa·s) was purchased from EMD Chemicals Inc. (480 South Democrat Road Gibbstown, N.J. 08027). Phosphate-buffered saline 1× (PBS 1×) was purchased from Mediatech Inc. (9345 Discovery Blvd. Manassas, Va. 20109.) Product Code 21-040-CV.

Method—Lot #14

Solutions were prepared as follows:

Solution 1: Ovalbumin protein @ 50 mg/mL was prepared in PBS 1× at room temperature.

Solution 2: PLGA was prepared by dissolving PLGA at 100 mg per 1 mL of dichloromethane in the chemical fume hood.

Solution 3: PLA was prepared by dissolving PLGA at 100 mg per 1 mL of dichloromethane in the chemical fume hood.

Solution 4: PLA-PEG-OMe was prepared by dissolving PLA-PEG-OMe at 100 mg per 1 mL of dichloromethane in the chemical fume hood.

Solution 5: Polyvinyl alcohol @ 50 mg/mL in 100 mM phosphate buffer, pH 8.

Solution 6: 70 mM phosphate buffer, pH 8.

A primary (W1/O) emulsion was first created by mixing Solutions 1 through 4. Solution 1 (0.2 mL), Solution 2 (0.5 mL), Solution 3 (0.25 mL) and Solution 4 (0.25 mL) were combined in a small glass pressure tube and sonicated at 50% amplitude for 40 seconds over an ice bath using a Branson Digital Sonifier 250. A secondary (W1/O/W2) emulsion was then formed by adding Solution 5 (3.0 mL) to the primary emulsion, vortexing to create a crude dispersion, and then sonicating at 30% amplitude for 60 seconds over an ice bath using the Branson Digital Sonifier 250. The secondary emulsion was added to an open 50 mL beaker containing Solution 6 (30 mL) and stirred at room temperature for 2 hours to allow the dichloromethane to evaporate and the nanocarriers to form in suspension. A portion of the suspended nanocarriers was washed by transferring the nanocarrier suspension to a centrifuge tube, spinning at 25,600 rcf for 45 minutes, removing the supernatant, and re-suspending the pellet in phosphate buffered saline. This washing procedure was repeated and then the pellet was re-suspended in PBS 1× to achieve a nanocarrier suspension having a nominal concentration of 10 mg/mL on a polymer basis. The suspension was stored frozen at −20 C until use.

Materials—Lot #15

PO-1826 DNA oligonucleotide with phosphodiester backbone having nucleotide sequence 5'-TCC ATG ACG TTC CTG ACG TT-3' (SEQ ID NO:2) with a sodium counter-ion was purchased from Oligo Factory (120 Jeffrey Avenue, Holliston, Mass. 01746.) PLGA having 54% lactide and 46% glycolide content and an inherent viscosity of 0.24 dL/g was purchased from SurModics Pharmaceuticals (756 Tom Martin Drive, Birmingham, Ala. 35211. Product Code 5050 DLG 2.5A). PLA-PEG-OMe block co-polymer with a methyl ether terminated PEG block of approximately 5,000 Da and PLA block of approximately 21,000 Da was synthesized. EMPROVE® Polyvinyl Alcohol 4-88, USP (85-89% hydrolyzed, viscosity of 3.4-4.6 mPa·s) was purchased from EMD Chemicals Inc. (480 South Democrat Road Gibbstown, N.J. 08027). Na cholate was purchased from Sigma Aldrich LLC. (3050 Spruce St. St. Louis, Mo. 6310. Product Code C6445-100G.) Phosphate-buffered saline 1× (PBS 1×) was purchased from Mediatech Inc. (9345 Discovery Blvd. Manassas, Va. 20109. Product Code 21-040-CV.)

Method—Lot #15

Solutions were prepared as follows:

Solution 1: PO-1826 was prepared by dissolving at 40 mg per 1 mL of an aqueous solution containing 150 mg KCl per 1 mL of endotoxin-free water.

Solution 2: Na Cholate was prepared by dissolving dry powder at 200 mg per 1 mL 1×PBS at room temperature.

Solution 3: PLGA was prepared by dissolving PLGA at 100 mg per 1 mL of dichloromethane in the chemical fume hood.

Solution 4: PLGA-PEG-OMe was prepared by dissolving PLGA-PEG-OMe at 100 mg per 1 mL of dichloromethane in the chemical fume hood.

Solution 5: Polyvinyl alcohol @ 50 mg/mL in 100 mM phosphate buffer, pH 8.

Solution 6: 70 mM phosphate buffer, pH 8.

A primary (W/O) emulsion was created by mixing Solutions 1 through 4 and creating a coarse emulsion prior to a fine emulsion. Solution 1 (0.25 mL), Solution 2 (0.25 mL), Solution 3 (0.5 mL), and Solution 4 (0.5 mL) were combined in a small glass pressure tube, coarsely emulsified by repeat pipetting, and sonicated at 50% amplitude for 40 seconds over an ice bath using a Branson Digital Sonifier 250. A secondary (W1/O/W2) emulsion was then formed by adding Solution 5 (3.0 mL) to the primary emulsion, vortexing to create a coarse dispersion, and then sonicating at 30% amplitude for 60 seconds over an ice bath using the Branson Digital Sonifier 250. The fine W1/O/W2 emulsion was added to an open 50 mL beaker containing 70 mM phosphate buffer (30 mL) and stirred at room temperature for 2 hours to allow the dichloromethane to evaporate and the nanocarriers to form in suspension. A portion of the suspended nanocarriers was washed by transferring the nanocarrier suspension to a centrifuge tube, spinning at 21,000 rcf for 90 minutes, removing the supernatant, and re-suspending the pellet in phosphate buffered saline. This washing procedure was repeated and then the pellet was re-suspended in PBS 1× to achieve a nanocarrier suspension having a nominal concentration of 10 mg/mL on a polymer basis. Nanocarrier suspension was then stored refrigerated until the concentration was determined, and then concentration adjusted and stored frozen at −20 C until use.

Materials—Lot #16

PO-1826 DNA oligonucleotide with phosphodiester backbone having nucleotide sequence 5'-TCC ATG ACG TTC CTG ACG TT-3' (SEQ ID NO:2) with a sodium counter-ion was purchased from Oligo Factory (120 Jeffrey Avenue, Holliston, Mass. 01746.) PLGA having 54% lactide and 46% glycolide content and an inherent viscosity of 0.24 dL/g was purchased from SurModics Pharmaceuticals (756 Tom Martin Drive, Birmingham, Ala. 35211. Product Code 5050 DLG 2.5A). PLA-PEG-OMe block co-polymer with a methyl ether terminated PEG block of approximately 5,000 Da and PLA block of approximately 21,000 Da was synthesized. EMPROVE® Polyvinyl Alcohol 4-88, USP (85-89% hydrolyzed, viscosity of 3.4-4.6 mPa·s) was purchased from EMD Chemicals Inc. (480 South Democrat Road Gibbstown, N.J. 08027). Phosphate-buffered saline 1× (PBS 1×) was purchased from Mediatech Inc. (9345 Discovery Blvd. Manassas, Va. 20109. Product Code 21-040-CV.)

Method—Lot #16

Solutions were prepared as follows:

Solution 1: PO-1826 was prepared by dissolving at 40 mg per 1 mL of an aqueous solution containing 150 mg KCl per 1 mL of endotoxin-free water.

Solution 2: Polyvinyl alcohol @ 100 mg/mL in 100 mM phosphate buffer, pH 8.

Solution 3: PLGA was prepared by dissolving PLGA at 100 mg per 1 mL of dichloromethane in the chemical fume hood.

Solution 4: PLGA-PEG-OMe was prepared by dissolving PLGA-PEG-OMe at 100 mg per 1 mL of dichloromethane in the chemical fume hood.

Solution 5: Polyvinyl alcohol @ 100 mg/mL in 100 mM phosphate buffer, pH 8.

Solution 6: 70 mM phosphate buffer, pH 8.

A primary (W/O) emulsion was created by mixing Solutions 1 through 4 and creating a coarse emulsion prior to a fine emulsion. Solution 1 (0.25 mL), Solution 2 (0.25 mL), Solution 3 (0.5 mL), and Solution 4 (0.5 mL) were combined in a small glass pressure tube, coarsely emulsified by repeat pipetting, and sonicated at 50% amplitude for 40 seconds over an ice bath using a Branson Digital Sonifier 250. A secondary (W1/O/W2) emulsion was then formed by adding Solution 5 (3.0 mL) to the primary emulsion, vortexing to create a coarse dispersion, and then sonicating at 30% amplitude for 60 seconds over an ice bath using the Branson Digital Sonifier 250. The fine W1/O/W2 emulsion was added to an open 50 mL beaker containing 70 mM phosphate buffer (30 mL) and stirred at room temperature for 2 hours to allow the dichloromethane to evaporate and the nanocarriers to form in suspension. A portion of the suspended nanocarriers was washed by transferring the nanocarrier suspension to a centrifuge tube, spinning at 21,000 rcf for 90 minutes, removing the supernatant, and re-suspending the pellet in phosphate buffered saline. This washing procedure was repeated and then the pellet was re-suspended in PBS 1× to achieve a nanocarrier suspension having a nominal concentration of 10 mg/mL on a polymer basis. Nanocarrier suspension was then stored refrigerated until the concentration was determined, and then concentration adjusted and stored frozen at −20 C until use.

Synthetic nanocarriers delivering CpG and OVA were superior in rapid antibody induction capacity than free high-dose CpG and OVA (both free CpG and free OVA used in 5× higher dose) and as successful or superior in induction of local and systemic antigen-specific CTLs as the same high dose of free CpG and free OVA.

Groups of three animals (C57BL/6 mice, females) were immunized (prime-boost, days 0 and 10; hind limb, s.c.) by three combinations of nanocarrier-incorporated CpG (ODN 1826) and OVA in parallel with immunization with 5-fold excess of free CpG and OVA. Three different formulations of NC-CpG were used with the same formulation of NC-OVA (see Table 13 for details). At 4 days after the second immunization animals were sacrificed and their serum, draining (popliteal) lymph nodes (LNs) and spleens were taken. Sera from immunized mice were used to determine antibody titer against ovalbumin, which was measured in standard ELISA with serial dilutions of test sera. Biotinylated goat anti-mouse Ig was used as a detection antibody (BD Biosciences, San Diego, Calif.). EC50 was determined based on titration curves. All NC-CpG formulations combined with NC-OVA induced more than 30-fold higher early antibody response against OVA than 5-fold higher doses of free CpG and OVA.

In parallel, the induction of OVA-specific CTLs was assessed ex vivo (without in vitro expansion) in draining LNs (locally) or spleens (systemically) via FACS analysis. Briefly, both tissues were treated with collagenase, homogenized, washed, cells counted using Trypan exclusion (Countess, Invitrogen, CA, USA) and labeled with antibodies or MHC class I-restricted pentamers coupled with fluorescent dyes capable of recognizing surface CD8 (T cell marker), CD19 (B cell marker) and T cell receptor (TCR) specific to MHC Class-1-restricted immunodominant OVA-derived peptide SIINFEKL (SEQ ID NO: 1).

Then differential cell populations were analyzed by FACS with those cells exhibiting CD8 expression (CD8$^+$), no CD19 expression (CD19) and bound to MHC Class I-complexed SIINFEKL (SEQ ID NO: 1) (SIINFEKL$^+$ (SEQ ID NO: 1)) considered representing a major species of OVA-specific CTLs. At least one of NC-CpG formulations used has equal or higher capacity to produce short-term CTLs locally and systemically when coupled with NC-OVA than 5-fold higher amounts of free CpG and OVA. Of note, different NC-CpG formulations have been especially beneficial for induction either of local or of systemic CTL response against nanocarrier-incorporated ovalbumin antigen.

Furthermore, purified splenocytes from immunized animals were also expanded in vitro (100 u/mL IL-2) by being stimulated with mitomycin-treated EG.7-OVA cells (syngeneic cells stably transfected with ovalbumin), which should result in preferential expansion of OVA-specific CD8$^+$ cells. At 11 days of in vitro incubation expanded cultures were labeled as described above and analyzed by FACS. All NC-CpG formulations tested resulted in induction of Ag-specific CTLs with a higher expansion potential than those induced by 5× doses of free CpG and OVA. Of note, one CpG formulation (NC-CpG) had especially strong potential for CTL expansion and another (NC-CpG) has exceeded systemic CTL induction levels by free high-dose CpG and OVA both when analyzed ex vivo and upon in vitro expansion.

TABLE 13

Experimental layout for testing of humoral and cellular immune response induced by nanocarrier-incorporated CpG and OVA vs. free CpG and OVA.

| Gr. # | Immunized w. | NC Lot | CpG (μg) | OVA (μg) | Regimen |
|---|---|---|---|---|---|
| 1 | NC-OVA + NC-CpG (1) | #12/#13 | 4.0 | 10 | 0/10 d |
| 2 | NC-OVA + NC-CpG (2) | #14/#15 | 4.0 | 10 | Same |
| 3 | NC-OVA + NC-CpG (3) | #14/#16 | 4.0 | 10 | Same |
| 4 | OVA + CpG (free) | N/A | 20 | 50 | Same |

What is claimed is:

1. A method consisting essentially of:
identifying a human subject in need of a humoral and cytotoxic T lymphocyte (CTL) immune response to a first protein, and
administering to the human subject a composition comprising one or more antigens that are associated with a disease, disorder or condition, wherein at least one antigen is the first protein coupled to a population of synthetic nanocarriers;
wherein the first protein comprises at least one humoral epitope and at least one MHC Class I-restricted epitope that are not the same epitope, wherein the population of synthetic nanocarriers does not comprise a saponin-cholesterol adjuvant, and wherein the mean of a particle size distribution obtained using dynamic light scattering of the population of synthetic nanocarriers is a maximum dimension of from 20 nm to 250 nm, and
administering to the human subject a single adjuvant.

2. A method, consisting essentially of:
administering to a human subject a composition comprising one or more antigens that are associated with a disease, disorder or condition, wherein at least one antigen is a first protein coupled to a population of synthetic nanocarriers;
wherein the first protein comprises at least one humoral epitope and at least one MHC Class I-restricted epitope that are not the same epitope, wherein the population of synthetic nanocarriers does not comprise a saponin-cholesterol adjuvant, wherein the mean of a particle size distribution obtained using dynamic light scattering of the population of synthetic nanocarriers is a maximum dimension of from 20 nm to 250 nm, and wherein the composition is administered according to a vaccination regimen that achieves immunity via both the humoral and cytotoxic T lymphocyte arms of the immune system, and
administering to the human subject a single adjuvant.

3. A method, consisting essentially of:
administering to a human subject a composition comprising one or more antigens that are associated with a disease, disorder or condition, wherein at least one antigen is a first protein coupled to a population of synthetic nanocarriers;
wherein the first protein comprises at least one humoral epitope and at least one MHC Class I-restricted epitope that are not the same epitope, wherein the population of synthetic nanocarriers does not comprise a saponin-cholesterol adjuvant, wherein the mean of a particle size distribution obtained using dynamic light scattering of the population of synthetic nanocarriers is a maximum dimension of from 20 nm to 250 nm, and wherein the composition is administered according to a protocol that was previously shown to result in a humoral and CTL immune response specific to the first protein in one or more test subjects, and
administering to the human subject a single adjuvant.

4. The method of any one of claims 1-3, wherein the composition is administered in an amount effective to generate a humoral and CTL immune response to the first protein.

5. The method of any one of claims 1-3, wherein the composition further comprises the single adjuvant.

6. The method of any one of claims 1-3, wherein the adjuvant is a stimulator or agonist of pattern recognition receptors, mineral salt, alum, MPL® (AS04), AS15, saponin, QS-21, Quil-A, ISCOMs, ISCOMATRIX™, MF59™, Montanide® ISA 51, Montanide® ISA 720, AS02, a liposome or liposomal formulation, AS01, synthesized or specifically prepared microparticles and microcarriers, bacteria-derived outer membrane vesicle of *N. gonorrhoeae* or *Chlamydia trachomatis*, chitosan particles, depot-forming agent, Pluronic® block co-polymer, specifically modified or prepared peptide, muramyl dipeptide, aminoalkyl glucosaminide 4-phosphate, RC529, bacterial toxoid, toxin fragment, agonist of Toll-Like Receptors 2, 3, 4, 5, 7, 8, or 9; adenine derivative; immunostimulatory DNA; immunostimulatory RNA; imidazoquinoline amine, imidazopyridine amine, 6,7-fused cycloalkylimidazopyridine amine, 1,2-bridged imidazoquinoline amine; imiquimod; resiquimod; agonist for DC surface molecule CD40; type I interferon; poly I:C; bacterial lipopolysaccharide (LPS); VSV-G; HMGB-1; flagellin; immunostimulatory DNA molecule comprising CpGs; proinflammatory stimuli released from necrotic cells; urate crystals; activated component of the complement cascade; activated component of immune complexes; complement receptor agonist; cytokine; or cytokine receptor agonist.

7. The method of claim 6, wherein the adjuvant comprises an agonist of Toll-Like Receptor 2, 3, 4, 7, 8 or 9.

8. The method of any one of claims 1-3, wherein the single adjuvant is coupled to the synthetic nanocarriers of the population of synthetic nanocarriers.

9. The method of any one of claims 1-3, wherein the adjuvant is coupled to another population of synthetic nanocarriers, and the other population of synthetic nanocarriers is administered to the subject.

10. The method of any one of claims 1-3, wherein the adjuvant is not coupled to a synthetic nanocarrier.

11. The method of any one of claims 1-3, wherein the synthetic nanocarriers comprise a polymeric nanoparticle, a metallic nanoparticle, a dendrimer, a buckyball, a nanowire, a virus-like particle or a peptide or protein particle.

12. The method of any one of claims 1-3, wherein the first protein and/or one or more additional antigens are antigens associated with cancer, an infection or infectious disease, a non-autoimmune or degenerative disease, HIV, malaria, leischmania, human filovirus, togavirus, alphavirus, arenavirus, bunyavirus, flavivirus, human papillomavirus, human influenza A virus, hepatitis B or hepatitis C.

13. The method of any one of claims 1-3, wherein the subject has or is at risk of having cancer, an infection or infectious disease or a non-autoimmune or degenerative disease.

14. The method of any one of claims 1-3, wherein, when the synthetic nanocarriers have a minimum dimension of equal to or less than 100 nm, the synthetic nanocarriers do not comprise a surface with hydroxyl groups that substantially activate complement.

15. The method of any one of claims 1-3, wherein the synthetic nanocarriers comprise one or more polymers.

16. The method of claim 15, wherein the one or more polymers comprise a polyester, polyamino acid, polycarbonate, polyacetal, polyketal, polysaccharide, polyethyloxazoline or polyethyleneimine.

17. The method of claim 16, wherein the one or more polymers comprise a polyester which comprises a poly (lactic acid), poly(glycolic acid), poly(lactic-co-glycolic acid) or polycaprolactone.

18. The method of claim 17, wherein the one or more polymers is coupled to a polyether.

19. The method of claim 18, wherein the polyether comprises polyethylene glycol.

* * * * *